US006479509B1

(12) United States Patent
Carroll

(10) Patent No.: US 6,479,509 B1
(45) Date of Patent: Nov. 12, 2002

(54) METHOD OF PROMOTING SMOKING CESSATION

(75) Inventor: Frank I. Carroll, Research Triangle Park, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 09/575,800

(22) Filed: May 22, 2000

(51) Int. Cl.$^7$ ............................................ A61K 31/44

(52) U.S. Cl. ...................................... 514/304; 514/813

(58) Field of Search ................................. 514/304, 813

(56) References Cited

U.S. PATENT DOCUMENTS

| | | | |
|---|---|---|---|
| 3,813,404 | A | 5/1974 | Clark et al. |
| 5,128,118 | A | 7/1992 | Carroll et al. |
| 5,186,921 | A | 2/1993 | Kung et al. |
| 5,316,759 | A | 5/1994 | Rose et al. |
| 5,374,636 | A | 12/1994 | Moldt et al. |
| 5,380,848 | A | 1/1995 | Kuhar et al. |
| 5,413,779 | A | 5/1995 | Kuhar et al. |
| 5,444,070 | A | 8/1995 | Moldt et al. |
| 5,496,953 | A | 3/1996 | Kuhar et al. |
| 5,554,626 | A | 9/1996 | Moldt et al. |
| 5,736,123 | A | 4/1998 | Carroll |
| 6,013,242 | A | 1/2000 | Davies et al. |
| 6,123,917 | A | * 9/2000 | Carroll ........................ 424/1.85 |
| 6,329,520 | B1 | * 12/2001 | Carroll et al. ............... 544/127 |
| 6,358,492 | B1 | * 3/2002 | Kuhar et al. ................ 424/1.85 |

FOREIGN PATENT DOCUMENTS

| | | |
|---|---|---|
| WO | WO 92/02260 | 2/1992 |
| WO | WO 97/16451 | 5/1997 |

OTHER PUBLICATIONS

G. K. Lloyd et al., "Neuronal Nicotinic Acetylcholine Receptors as Novel Drug Targets", *The Journal of Pharmacology and Experimental Therapeutics*, Perspectives in Pharmacology, Oct. 5, 1999, vol. 292, No. 2, pp. 461–467.
J. E. Rose et al., "Concurrent Agonist–Antagonist Administration for the Analysis and Treatment of Drug Dependence", *Pharmacology Biochemistry & Behavior*, Rapid Communication, 1991, vol. 41, pp. 219–226.
M. I. Damaj et al., "Pharmacological Characterization of Nicotine's Interaction with Cocaine and Cocaine Analogs", *The Journal of Pharmacology and Experimental Therapeutics*, Jan. 28, 1999, vol. 289, No. 3, pp. 1229–1236.
N. Lerner–Marmarosh et al., "Antagonism of Nicotine's Action by Cocaine Analogs", *Life Sciences*, Pharmacology Letters, Accelerated Communication, Oct. 25, 1994, vol. 56, No. 3, pp. 67–70.

C. G. V. Sharples et al., "UB–165: A Novel Nicotinic Agonist with Subtype Selectivity Implicates the α4β2 Subtype in the Modulation of Dopamine Release from Rat Striatal Synaptosomes", *The Journal of Neuroscience*, Apr. 15, 2000, vol. 20, No. 8, pp. 2783–2791.
A. H. Lewin et al., "Positive Identification and Quantitation of Isomeric Cocaines by High–Performance Liquid Chromatography", *Journal of Chromatography*, Jan. 17, 1980, vol. 193, pp. 371–380.
A. Chang et al., "Synthesis and Transporter Binding Properties of 2,3–Diphenyltropane Stereosiomers, Comparison to 3β–Phenyltropane–2β–Carboxylic Acid Esters", *Journal of Medicinal Chemistry*, 1997, vol. 40, No. 8, pp. 1247–1251.
F. I. Carroll et al., "Syntheses and Conformational Analyses of Isomeric Cocaines: A Proton and Carbon–13 Nuclear Magnetic Resonance Study", *The Journal of Organic Chemistry*, 1982, vol. 47, No. 13, pp. 13–19.
A. H. Lewin et al., "A Practical Synthesis of (+)–Cocaine", *Journal of Heterocyclic Chemistry*, 1987, vol. 24, No. 19, pp. 19–21.
F. I. Carroll et al., "Cocaine Receptor–Design of Ligands", *Drugs of Abuse: Chemistry, Pharmacology, Immunology, and AIDS*, NIDA Monograph 96, 1990, pp. 112–121.
T. M. Naseree et al., "Synthesis of [$^3$H]WIN 35,065–2; A New Radioligand for Cocaine Receptors", *Journal of Labelled Compounds and Radiopharmaceuticals*, 1989, vol. XXVIII, No. 9, pp. 1011–1016.
M. C. Ritz et al., "[$^3$H]WIN 35,065–2: A Ligand for Cocaine Receptors in Striatum", *Journal of Neurochemistry*, 1990, vol. 55, pp. 1556–1562.
J. W. Boja et al., "New, Potent Cocaine Analogs: Ligand Binding and Transport Studies in Rat Striatum", *European Journal of Pharmacology*, 1990, vol. 184, pp. 329–332.
M. J. Kuhar et al., "Imaging Neurotransmitter Uptake Sites in Brain", *Soc. Neurosci.*, 1990, 16, 746.
F. I. Carroll et al., "Important Compounds in the Cocaine Class: A Synthesis Overview", *Emerging Technologies and New Directions in Drug Abuse Research*, NIDA Research Monograph No. 112, 1991, pp. 284–299.
F. I. Carroll et al., "Synthesis and Receptor Binding of Cocaine Analogs", *Problems of Drug Dependence 1990*, NIDA Research Monograph 105, 1991, pp. 147–153.
F. I. Carroll et al., "Synthesis and Ligand Binding of Cocaine Isomers at the Cocaine Receptor", *Journal of Medicinal Chemistry*, 1991, vol. 34, pp. 883–886.
J. W. Boja et al., "[$^{125}$I]RTI–55: A Potent Ligand for Dopamine Transporters", *European Journal of Pharmacology*, 1991, vol. 194, pp. 133–134.

(List continued on next page.)

*Primary Examiner*—Zohreh Fay
*Assistant Examiner*—C. Delacroix-Muirheid
(74) *Attorney, Agent, or Firm*—Oblon, Spivak, McClelland, Maier & Neustadt, P.C.

(57) ABSTRACT

A method of training a smoker to cease smoking by administering tropane compounds is provided.

24 Claims, 7 Drawing Sheets

OTHER PUBLICATIONS

J. W. Boja et al., "Isothiocyanate Derivatives of Cocaine: Irreversible Inhibition of Ligand Binding at the Dopamine Transporter", *Molecular Pharmacology*, Nov. 28, 1990, vol. 39, pp. 339–345.

J. J. Woodward et al., "Cocaethylene Inhibits Dopamine Uptake and Produces Cocaine–Like Actions in Drug Discrimination Studies", *European Journal of Pharmacology*, 1991, vol. 197, pp. 235–236.

F. I. Carroll et al., "Synthesis, Ligand Binding, QSAR, and COMFA Study of 3β–(p–Substituted Phenyl–Tropane–2β–Carboxylic Acid Methyl Esters", *Journal of Medicinal Chemistry*, 1991, vol. 34, No. 9, pp. 2719–2725.

R. L. Balster et al., "Potent Substituted–3β–Phenyl Tropane Analogs of Cocaine Have Cocaine–Like Discriminative Stimulus Effects", *Drug and Alcohol Dependence*, 1991, vol. 29, pp. 145–151.

F. I. Carroll et al., "[$^{123}$I]3β–(4–Iodophenyl) Tropan–2β–Carboxylic Acid Methyl Ester (RTI–55), A Unique Cocaine Receptor Ligand for Imaging the Dopamine and Serotonin Transporters in Vivo", *Medicinal Chemistry Research*, 1991, vol. 1, pp. 289–294.

R. B. Rothman et al., "Preliminary Evidence That GBR12909 is Less Effective Oat Elecating Mesolimbic Dopamine Function Than Cocaine", *Problems of Drug Dependence*, Proceedings of the 53$^{rd}$ Annual Scientific Meeting, Committee on Problems of Drug Dependence, Inc., 1991, p. 338.

P. Abraham et al., "N–Modified Analogues of Cocaine: Synthesis and Inhibition of Binding to the Cocaine Receptor", *Journal of Medicinal Chemistry*, 1992, vol. 35, No. 1, pp. 141–144.

A. H. Lewin et al., "2β–Substituted Analogues of Cocaine. Synthesis and Inhibition of Binding to the Cocaine Receptor", *Journal of Medicinal chemistry*, 1992, vol. 35, No. 1, pp. 135–140.

F. I. Carroll et al., "Cocaine Receptor: Biochemical Characterization and Structure–Activity Relationships of Cocaine Analogues at the Dopamine Transporter", *Journal of Medicinal Chemistry*, 1992, vol. 35, No. 6, pp. 969–981.

F. I. Carroll et al., "Synthesis and Ligand Binding of 3β–(3–Substituted Phenyl)–and 3β–(3,4–Disubstituted Phenyl–Tropane–2β–Carboxylic Acid Methyl Esters", *Medicinal Chemistry Research*, 1992, vol. 1, pp. 382–387.

F. I. Carroll et al., "Probes for the Cocaine Receptor, Potentially Irreversibly Ligands for the Dopamine Transporter", *Journal of Medicinal Chemistry*, 1992, vol. 35, No. 10, pp. 1813–1817.

E. K. Shaya et al., "In Vivo Imaging of Dopamine Reuptake Sites in the Primate Brain Using Single Photon Emission Computed Tomography (SPECT) and Iodine–123 Labeled RTI–55", *Synapse*, 1992, vol. 10, pp. 169–172.

E. J. Cline et al., "Behavioral Effects of Novel Cocaine Analogs: A Comparison with In Vivo Receptor Binding Potency", *The Journal of Pharmacology and Experimental Therapeutics*, Dec. 2, 1991, vol. 260, No. 3, pp. 1174–1179.

A. Patel et al., "A Cocaine Analog and a GBR Analog Label the Same Protein in Rat Striatal Membranes", *Brain Research*, 1992, vol. 576, pp. 173–174.

J. W. Boja et al., "High Potency Cocaine Analogs: Neurochemical, Imaging, and Behavioral Studies", *Annals New York Academy of sciences*, pp. 282–291.

J. W. Boja et al., "High Affinity Binding of [$^{125}$I ]RTI–55 to Dopamine and Serotonin Transporters in Rat Brain", *Synapse*, 1992, vol. 12, pp. 27–36.

U. Scheffel et al., "[$^{123/125}$I]RTI–55, An In Vivo Label for the Serotonin Transporter", *Synapse*, 1992, vol. 11, pp. 34–39.

E. J. Cline et al., "Stimulus Generalization from Cocaine to Analogs with High In Vitro Affinity for Dopamine Uptake Sites", *Behavioral Pharmacology*, 1992, vol. 3, pp. 113–116.

M. C. Ritz et al., "Isopropyl and Phenyl Esters of 3β–(4–Substituted Phenyl)Tropan–2β–Carboxylic Acids, Potent and Selective Compounds for the Dopamine Transporter", *Journal of Medicinal Chemistry*, Communications to the Editor, 1992, vol. 35, No. 13, pp. 2497–2500.

J. F. Casale et al., "Base–Catalyzed C–2 Exchange and Epimerization of Cocaine Analogs: Methyl 3β–Substituted 8–Methyl–8–Azabicyclo[3.2.1]Octane–2–Carboxylates", *The Journal of Organic Chemistry*, 1992, vol. 57, No. 18, pp. 4906–4912.

E. J. Cline et al., "In Vivo Binding of [$^{125}$I]RTI–55 to Dopamine Transporters: Pharmacology and Regional Distribution with Autoradiography", *Synapse*, 1992, vol. 12, pp. 37–46.

U. Scheffel et al., "Dopamine Transporter Imaging with Novel Selective Cocaine Analogs", *NeuroReport*, Membrane and Cellular Biophysics and Biochemistry, Nov. 1992, vol. 3, No. 11, pp. 969–972.

J. W. Boja et al., "Selective Dopamine Transporter Inhibition by Cocaine Analogs", *NeuroReport*, Molecular Neuroscience, Nov. 1992, vol. 3, No. 11, pp. 984–986.

R. B. Rothman et al., "Cocaine and GBR12909 Produce Equivalent Motoric Responses at Different Occupancy of the Dopamine Transporter", *Pharmacology Biochemistry and Behavior, 1992*, 1992, vol. 43, pp. 1135–1142.

W. Rostène et al., "Dopamine Transport: Pharmacological Distinction Between the Synaptic Membrane and the Vesicular Transporter in Rat Striatum", *European Journal of Pharmacology*, 1992, vol. 218, pp. 175–177.

F. I. Carroll et al., "Pharmacophore Development of (–)–Cocaine Analogs for the Dopamine, Serotonin, and Norepinephrine Uptake Sites Using QSAR and COMFA Approach", Supported in part by the National Institute on Drug Abuse, grant No. DA05477.

F. I. Carroll et al., "Cocaine Receptor: A Structure–Activity Relationship Study", In *Medications Development: Drug Discovery, Databases and Computer–Aided Drug Design*, NIDA Research Monograph No. 134, 1993, pp. 229–237.

F. I. Carroll et al., "3β–(Substituted Phenyl–Tropan– 2–Carboxylic Acid Ester Analogues of Cocaine", *Drug Design for Neuroscience*, New York, 1993, pp. 149–166.

F. I. Carroll et al., "Synthesis and Cocaine Receptor Affinities of 3–Phenyl–2–(3'–Methyl–1,2,4–Oxadiazole–5'–YL) Tropane Isomers", *Journal Chem. Society, Chemical Communication*, The Royal Society of Chemistry, 1993, Issue 1, pp. 44–46.

K. Y. Little et al., "[$^{125}$I]RTI–55 Binding to Cocaine–Sensitive Dopaminergic and Serotonergic Uptake Sites in the Human Brain", *Journal of Neurochemistry*, 1993, vol. 61, No. 6, pp. 1996–2006.

F. I. Carroll et al., "3–Aryl–2–(3'–Substituted–1', 2', 4'–Oxadiazol–5'–YL)Tropane Analogues of Cocaine" Affinities at the Cocaine Binding Site at the Dopamine, Serotonin, and Norepinephrine Transporters, *Journal of Medicinal Chemistry*, 1993, vol. 36, No. 20, pp. 2886–2890.

J. R. Lever et al., "Radiosynthesis of a Photoaffinity Probe for the Cocaine Receptor of the Dopamine Transporter: 3β–(p–Chlorophenyl)Tropan–2β–Carboxylic Acid m–([$^{125}$I]–IODO)–p–Azidophenehyl Ester ([$^{125}$II]–RTI–82)", Journal of Labelled Compounds and Radiopharmaceuticals, 1993, vol. XXXIII, No. 12, pp. 1131–1137.

K. Y. Little et al., "Cocaine Use Increases [$^3$H] WIN 35428 Binding Sites in Human Striatum", Brain Research, 1993, vol. 638, pp. 17–25.

F. I. Carroll et al., "Hallucinogenic Agents: Drugs of Abuse as Neurochemical Tools", Problems of Drug Dependence, NIDA Research Monograph 140, Proceedings of the 55$^{th}$ Annual Scientific Meeting, College of Problems of Drug Dependence, Inc., 1993, pp. 94–98.

R. B. Rothman et al.,. "Studies of the Biogenic Amine Transporters. II. A Brief Study on the Use of [$^3$H] DA–Uptake–Inhibition to Transporter–Binding–Inhibition Ratios for the In Vitro Evaluation of Putative Cocaine Antagonists", Life Sciences, 1993, vol. 53, Vo. 17, pp. PL–267–PL–272.

M. J. Kuhar et al., "A Cocaine Receptor: Properties and Significance", Biological Bassi of Substance Abuse, Cell Biology, 1993, pp. 71–80.

F. I. Carroll et al., "3β–(4'–Chlorophenyl)Tropan–2β–Carboxamides and Cocaine Amide Analogues: New High Affinity and Selective Compounds for the Dopamine Transporter" Medicinal Chemistry Research, 1993, vol. 3, pp. 468–472.

C. M. Dersch et al., "Studies of the Biogenic Amine Transporters. 1. Dopamine Reuptake Blockers Inhibit [$^3$H]Mazindol Binding to the Dopamine Transporter by a Competitive Mechanism: Preliminary Evidence for Different Binding Domains", Neurochemical Research, 1994, vol. 19, No. 2, pp. 201–208.

J. W. Boja et al., "Secondary Amine Analogues of 3β–(4'–Substituted Phenyl)Tropane–2β–Carboxylic Acid Esters and N–Norcocaine Exhibit Enhanced Affinity for Serotonin and Norepinephrine Transporters", Journal of Medicinal Chemistry, 1994, vol. 37, No. 8, pp. 1220–1223.

F. I. Carroll et al., "Chemical Approaches to the Treatment of Cocaine Abuse", Pharmaceutical News, Technical Review, 1994, vol. 1, No. 2, pp. 11–17.

H. C. Akunne et al., "Studies of the Biogenic Amine Transporter. III. Demonstration of Two Binding Sites for [$^3$H]BTCP in Rat Caudate Membranes", The Journal of Pharmacology and Experimental Therapeutics, 1992, vol. 268, No. 3, pp. 1462–1475.

F. I. Carroll et al., "Synthesis, Ligand Binding, and QSAR (COmfa and Classical) Study of 3β–(3'–Substituted Phenyl)–, and 3β–4'–Substituted Phenyl)–,and 3β–(3', 4'–Disubstituted Phenyl)Tropane–2β–Carboxylic Acid Methyl Esters", Journal of Medicinal Chemistry, 1994, vol. 37, No. 18, pp. 2865–2873.

R. B. Rothman et al., "Studies of the Biogenic Amine Transporters. IV. Demonstration of Multiplicity of Binding Sites in Rat Caudate Membranes for the Cocaine Analog [$^{125}$I]RTI–55", The Journal of Pharmacology and Experimental Therapeutics, 1994, vol. 270, No. 1, pp. 296–309.

D. Matecka et al., "Synthesis and Absolute Configuration of Chiral Piperazines Related to GBR 12909 as Dopamine Reuptake Inhibitors", Medicinal Chemistry Research, 1994, vol. 5, pp. 43–53.

F. I. Carroll et al., "Cocaine and 3β–(4'–Substituted Phenyl)Tropane–2β–Carboxylic Acid Ester and Amide Analogues. New High–Affinity and Selective Compounds for the Dopamine Transporter", Journal of Medicinal Chemistry, 1995, vol. 38, No. 2, pp. 279–388.

M. L. Silverthorn et al., "Studies of the Biogenic Amine Transporter. V. Demonstration of Two Binding Sites for the Cocaine Analog [$^{125}$I]RTI–55 Associated with the 5–HT Transporter in Rat Brain Membranes", The Journal of Pharmacology and Experimental Therapeutics, 1995, vol. 273, No. 1, pp. 213–222.

F. I. Carroll et al., "Development of Imaging Agents for the Dopamine Transporter", Medicinal Research Reviews, 1995, vol. 15, No. 5, pp. 419–444.

N. Lerner–Marmarosh et al., "Antagonism of Nicotine's Action by Cocaine Analogs", Life Sciences, Pharmacology Letters, Accelerated Communication, 1995, vol. 56, No. 3, pp. 67–70.

K. I. Keverline et al., "Synthesis if the 2β,3α– and 2β,3β–Isomers of 3–(p–Substituted Phenyl)Tropane–2–Carboxylic Acid Methyl Esters", Tetrahedron Letters, 1995, vol. 36, No. 18, pp. 3099–3102.

M. Stathis et al., "Rate of Binding of Various Inhibitors at the Dopamine Transporter In Vivo", Psychopharmacology, 1995, vol. 119, pp. 376–384.

N. D. Volkow et al, "Long–Lasting Inhibition of In Vivo Cocaine Binding T Dopamine Transporters by 3β–(4–Iodonphenyl)Tropane–2–Carboxylic Acid Methyl Ester:RTI–55 or βCIT", Synapse, 1995, vol. 19, pp. 206–211.

R. B. Rothman et al., "Studies of the Biogenic Amine Transporters. VI. Characterization of a Novel Cocaine Binding Site, Identified with [$^{125}$I]RTI–55, in Membranes Prepared from Whole Rat Brain Minus Caudate" The Journal of Pharmacology and Experimental Therapeutics, 1995, vol. 274, No. 1, pp. 385–395.

J. W. Boja et al., "Selective Labeling of the Dopamine Transporter by the High Affinity Ligand 3β–(4–[$^{125}$I] Iodophenyl)Tropane–2β–Carboxylic Acid Isopropyl Ester", Molecular Pharmacology, 1995, vol. 47, pp. 779–786.

J. K. Staley et al., "MAPPING Dopamine Transporters in the Human Brain with Novel Selective Cocaine Analog [$^{125}$I] RTI–121", Synapse, 1995, vol. 21, pp. 364–372.

Pravin Kotian et al., "Synthesis and Ligand Binding Study of 3β–(4'–Substituted Phenyl)–3β–(Heterocyclic)Tropanes", J. Med. Chem., vol. 38, pp. 3451–3453, 1995.

Karley Y. Little et al., Characterization and Localization of [$^{125}$I]RTI–121 Binding Sites in Human Striatum and Medial Temporal Lobe[1,2], The Journal of Pharmacology and Experimental Therapeutics, vol. 274, No. 3, pp. 1473–1483, 1995.

John L. Musachio et al., "3β–(P–Trimethylsilyl-phenyl)Tropane–2β–Carboxylic Acid Methyl Ester: A New Precursor for the Preparation of [$^{123}$I]RTI–55", Appl. Radiat. Isot., vol. 47, No. 1, pp. 79–81, 1996.

S. John Gatley et al., "Displacement of RTI–55 from the Dopamine Transporter by Cocaine", European Journal of Pharmacology, vol. 296, pp. 145–151, 1996.

John R. Lever et al., Synthesis and In Vivo Studies of a Selective Ligand for the Dopamine Transporter: 3β–(4–[$^{125}$I]Iodophenyl) Tropan–2β–Carboxylic Acid Isopropyl Ester ([$^{125}$I]RTI–121), Nuclear Medicine & Biology, vol. 23, pp. 277–284, 1996.

Pravin Kotian et al., "Synthesis, Ligand Binding, and Quantitative Structure–Activity Relationship Study of 3β–(4'–Substituted Phenyl)–2β–Heterocyclic Tropanes: Evidence for an Electrostatic Interaction at the 2β–Position", J. Med. Chem., vol. 39, pp. 2753–2763, 1996.

Susan P. Hume et al., "Evaluation of [$^{11}$C]RTI–121 as a Selective Radioligand for Pet Studies of the Dopamine Transporter", Nuclear Medicine & Biology, vol. 23, pp. 377–384, 1996.

Bruce E. Blough et al., "Synthesis and Transporter Binding Properties of 3β-(4'-Alkyl-, 4'-Alkenyl-, and 4'-Alkynylphenyl)Nortropane-2β-Carboxylic Acid Methyl Esters: Serotonin Transporter Selective Analogs", J. Med. Chem., vol. 39, pp. 4027–4035, 1996.

Christopher R. Holmquist et al., "3α-(4'-Substituted Phenyl)Tropane-2β-Carboxylic Acid Methyl Esters: Novel Ligands with High Affinity and Selectivity at the Dopamine Transporter", J. Med. Chem., vol. 39, pp. 4139–4141, 1996.

Karley, Y. Little et al., "Lack of Dopamine Receptor Agonists Effect on Striatal Dopamine Transporter Binding Sites", Brain Research, vol. 742, pp. 313–316, 1996.

Annette E. Fleckenstein et al., "Recovery of Dopamine Transporter Binding A Function After Intrastriatal Administration of the Irreversible Inhibitor RTI–76 (3β-(3p-Chlorophenyl)Tropan-2β-Carboxylic Acid P-Isothiocyanatophenylethyl Ester Hydrochloride)[1]", The Journal of Pharmacology and Experimental Therapeutics, vol. 279, pp. 200–206, 1996.

G.I. Elmer et al., "Cocaine Cross–Sensitization to Dopamine Uptake Inhibitors: Unique Effects of GBR12909", Pharmacology Biochemistry and Behavior, vol. 53, No. 4, pp. 911–918, 1996.

Annette E. Fleckenstein et al., "Highly Potent Cocaine Analogs Cause Long–Lasting Increases in Locomotor Activity", European Journal of Pharmacology, vol. 311, pp. 109–114, 1996.

Michael J. Kuhar et al., "Imaging Transporters for Dopamine and Other Neurotransmitters in Brain", Neurotransmitter Transporter: Structure, Function, and Regulation, Ed: M.E.A. Reith Humana Press, Inc., Totowa, NJ., pp. 297–313, 1997.

F. Ivy Carroll et al., "Dopamine Transporter Uptake Blockers", Neurotransmitter Transporter: Structure, Function, and Regulation, Ed: M.E.A. Reith Humana Press, Inc., Totowa, NJ., pp. 263–295.

Yougen Zhan et al., "TRI–352: A 3α Analogue of TRI–55 as an In Vivo Dopamine Transporter Binding Ligand", Synapse, vol. 25, pp. 389–392, 1997.

Karley Y. Little et al., "Serotonin Transporter Binding Sites and mRNA Levels in Depressed Persons Committing Suicide", Society of Biological Psychiatry, vol. 41, pp. 1156–1164, 1997.

Mohan Thiruvazhi et al., "Synthesis of the Isomers of (1R)-3-Phenylthio)Tropane-2-Carboxylic Acid Methyl Ester. A New Class of Ligands for the Dopamine Transporter", Chem. Commun., pp. 555–556, 1997.

Bruce E. Blough et al., "3β-(4-Ethyl-3-Iodophenyl)Nortropane-2β-Carboxylic Acid Methyl Ester as a High-Affinity Selective Ligand for the Serotonin Transporter", Journal of Medicinal Chemistry, vol. 40, No. 24, pp. 3861–3864, 1997.

Ursula Scheffel et al., "N–Substituted Phenyltropanes as In Vivo Binding Ligands for Rapid Imaging Studies of the Dopamine Transporter", Synapse, vol. 25, pp. 345–349, 1997.

Richard B. Rothman et al., "Studies of the Biogenic Amine Transporters. VII. Characterization of a Novel Cocaine Binding Site Identified with [$^{125}$I]RTI–55 in Membranes Prepared from Human, Monkey and Guinea Pig Caudate", Synapse, vol. 28, pp. 322–338, 1998.

Steven I. Dworkin et al., "RTI–113 Administration Reduces Cocaine Self–Administration at High Occupancy of Dopamine Transporter", Synapse, vol. 30, pp. 49–55, 1998.

Kathryn I. Keverline–Frantz et al.,"Synthesis and Ligand Binding of Tropane Ring Analogues of Paroxetine", Journal of Medicinal Chemistry, vol. 41, No. 2, pp. 247–257, 1998.

J.W. Boja et al., "Multiple Binding Sites for [$^{125}$i]RTI–121 and Other Cocaine Analogs in Rat Frontal Cerebral Cortex", Synapse, vol. 30, pp. 9–17, 1998.

C.D. Cook et al., Separation of the Locomotor Stimulant and Discriminative Stimulus Effects of Cocaine by its C–2 Phenyl Ester Analog, RTI–15, Drug and Alcohol Dependencies, vol. 50, pp. 123–128, 1998.

F. Ivy Carroll et al., "3–β–Substituted Tropanes—An SAR Analysis", Med. Chem Res., vol. 8:1/2, pp. 59–65, 1998.

Karley Y. Little et al., "Striatal [$^{125}$]RTI–55 Binding Sites in Cocaine–Abusing Humans", Prog. Neuro–Physchopharmacol. & Psychiat., vol. 22, pp. 455–466, 1998.

Songchun Jiang et al. "Synthesis and Transporter Binding Properties of (R)–2β,3β– and (R)2α–3α–Diaryltropanes", Biorganic & Medicinal Chemistry Letters, vol. 8, pp. 3689–3692, 1998.

Maarten E. A. Reith et al., "[17] Inhibition of [$^3$H]Dopamine Translocation and [$^3$H]Cocaine, Analog Binding: A Potential Screening Device for Cocaine Antagonists", Methods in Enzymology, vol. 296, pp. 248–259, 1998.

F. Ivy Carroll et al., "Pharmacotherapies for Treatment of Cocaine Abuse: Preclinical Aspects", Journal of Medicinal Chemistry, Vo. 41, No. 15, pp. 2721–2736, 1999.

Sari Izenwasser et al., "Continuous Infusion of Selective Dopamine Uptake Inhibitors or Cocaine Produces Time–Dependent Changes in Rat Locomotor Activity", Behavioral Brain Research, vol. 99, pp. 201–208, 1999.

Desong Zhong et al., "Synthesis of 3β-(4-[$^{125}$I]Iodophenyl)Tropane–2–β–Pyrrolidine Carboxamide ([$^{125}$I] RTI–229)", Journal of Labeled Compounds and Radiopharmaceuticals, vol. 42, pp. 281–286, 1999.

Michael J. Kuhar et al., "Studies of Selected PhenylTropanes at Monoamine Transporters", Drug and Alcohol Dependencies, vol. 56, pp. 9–15, 1999.

Aleksandra Vicentic et al., "Serotonin Transporter Production and Degradation Rates: Studies with RTI–76", Brain Research, vol. 841, pp. 1–10, 1999.

Desong Zhong et al., "Synthesis of $^{125}$I–3β-(4–Ethyl–3–Iodophenyl)Nortropane–2β–Carboxylic Acid Methyl Ester ([$^{125}$I]EINT)", Journal of Labelled Compounds and Radiopharmaceuticals, vol. 43, pp. 137–146, 2000.

Leonard L. Howell et al., "Comparative Behavioral Pharmacology of Cocaine and the Selective Dopamine Uptake Inhibitor RTI–113 in the Squirrel Monkey", The Journal of Pharmacology and Experimental Therapeutics, Vo. 292, No. 2, pp. 521–529, 2000.

* cited by examiner

Comparison of cocaine and its analogs for blockade of antinociception induced by nicotine. Antagonists were administered i.p. 10 min before nicotine (2.5 mg/kg) was administered s.c., and mice were tested 5 min after nicotine injection in tail-flick test. Each point represents mean ± S.E. of 8 to 12 mice.

Nicotine (mg/kg)

Dose-response relationship of nicotine-induced antinociception and its antagonism by cocaine. Cocaine (5 mg/kg) was administered i.p. 10 min before nicotine, and mice were tested 5 min after nicotine injection in tail-flick test. Each point represents mean ± S.E. of 8 to 12 mice.

Correlation between dopamine (A), norepinephrine (B), and serotonin (C) transporter binding potencies ($IC_{50}$ expressed as nM) and nicotinic antagonistic potency ($AD_{50}$ values expressed as µmol/kg) for cocaine analogs in tail-flick test.

Blockade of nicotine-induced motor impairment by cocaine. Cocaine was administered i.p. 10 min before nicotine and mice were tested 20 min after nicotine (2.5 mg/kg) injection. Effect of vehicle (–□–) is also represented in graph. Each point represents mean ± S.E. of 8 to 12 mice. Statistically different from nicotine (alone) at $P < .05$.

FIGURE 5

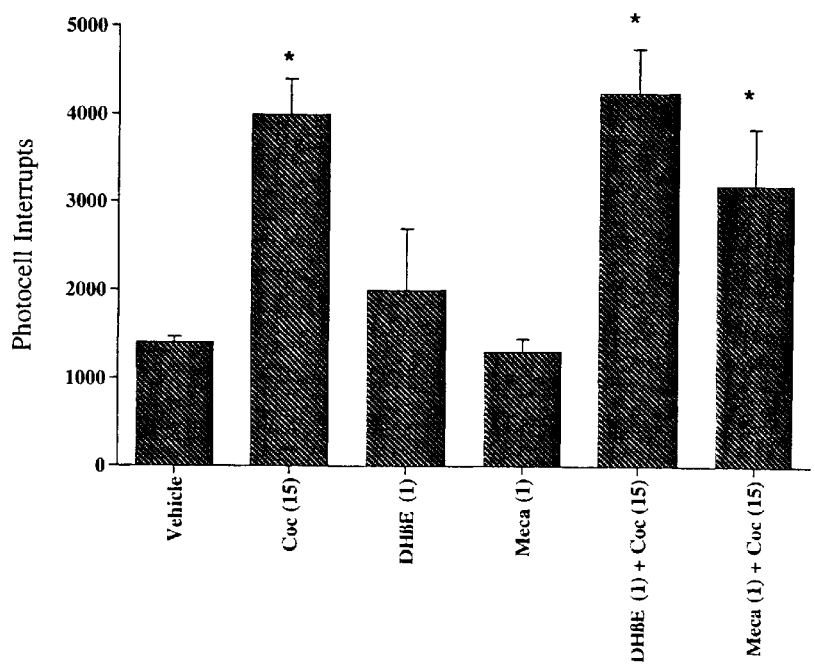

Failure of nicotinic antgonists DH$\beta$E and mecamylamine in blocking cocaine-induced increase in locomotor activity in mice. antagonists were administered s.c. 10 min before cocaine (15 mg/kg) i.p. injection. Ten minutes later, mice were placed into activity cages for 30 min. Each point represents mean ± S.E. of 8 to 12 mice. Coc, = cocaine; Meca = mecamylamine. *Statistically different from vehicle at $P < .05$.

Lack of blockade of nicotine-induced antinociception by cocaine-methiodide after i.p. administration in mice using tail-flick test. Cocaine-methiodide (at 10 and 25 mg/kg) was administered 10 min before nicotine and mice were tested 5 min after nicotine (2.5 mg/kg) injection. Each point represents mean ± S.E. of 8 to 12 mice. Coc-I, cocaine-methiodide; Nic, nicotine.

Effect of different concentrations of cocaine on current activated by 1 μM nicotine (A) applied in $\alpha_4\beta_2$-expressing oocytes and 10 μM nicotine (B) applied in $\alpha_3\beta_2$-expressing oocytes. Nicotine or cocaine was applied as a 10-s pulse and changes in current from baseline values was measured for a total of 1 min. Oocytes were held at −70 mV.

METHOD OF PROMOTING SMOKING CESSATION

BACKGROUND OF THE INVENTION

1. Field of the Invention

The present invention relates to methods and reagents for promoting smoking cessation. The present invention relates to methods and reagents for preventing smoking addiction. The present invention also relates to methods and reagents for treating nicotine addiction.

2. Background of the Invention

Smoking addiction is a complex phenomenon believed to involve cognition enhancement, psychological conditioning, stress adaptation, reinforcing properties and relief from withdrawal. Consequently, providing therapeutic treatment for smoking addiction is an extremely difficult challenge.

Tobacco products, including cigarettes, cigars, pipes and smokeless tobacco, can cause a variety of well-recognized health problems. From a public health perspective, it is desirable to stop consuming tobacco products, especially in the form of smoking. However, some individuals cannot quit smoking tobacco products, in spite of focused attempts to succeed. One major factor in the difficulty of quitting smoking is the presence of nicotine in tobacco.

Nicotine can produce a myriad of behavioral effects and is unquestionably one of the most popular and powerful reinforcing agents. In addition, smoking, arguably the vehicle of choice for nicotine delivery, may cause a variety of well-recognized health problems. For these reasons it has sometimes been desirable to cease consumption of nicotine. However, for some, the termination of nicotine consumption can not be accomplished, in spite of focused attempts to succeed.

One method for assisting smoking cessation is to reduce consumption over time. For complex reasons, this method is not always entirely successful. One method for assisting smoking cessation is to provide an alternate delivery vehicle for nictone. Such delivery vehicles include oral preparations such as gums, and transdermal vehicles such as skin patches.

Another method for assisting smoking cessation is to replace the nicotine signal from tobacco with a substitute reinforcer. Bupropion is used to promote smoking cessation and it may act as a substitute reinforcer.

Nicotine antagonists have been considered as an approach to smoking cessation. A nicotine antagonist would block the reinforcing signal from nicotine that creates and maintains the addiction to smoking. Over time, the smoker would dissociate the physical and psychological aspects of smoking. For example, mecamylamine has been used to promote smoking cessation, although it is generally ineffective alone. Another approach is to administer an antagonist, e.g., mecamylamine, together with nicotine replacement therapy. Compounds which act as nicotine substitutes and block nicotine's effects would be preferred smoking cessation reagents.

Lerner-Mamarosh et al. *Life Sci.* 56:67–70 (1995) describe antagonism of nicotine's action by 3-phenyl-substituted tropane analogs of cocaine. The study demonstrated that the phenyltropanes blocked nicotine-induced seizures in mice. The authors also found that the analogs could compete with mecamylamine, an indirect nicotine antagonist, in vitro. However, the results of this study do not suggest that the phenyltropane compounds could be used to treat nicotine addiction and provide a method of smoking cessation.

The phenyltropane analogs were well-known to inhibit the reuptake of dopamine, serotonin and norepinephrine. Lerner-Mamarosh et al. demonstrated that the anti-seizure activity of the phenyltropanes correlated with the ability of the analogs to inhibit the dopamine transporter. Therefore, it was highly likely that the anti-seizure activity was an indirect effect of the phenyltropanes on dopamine.

Lerner-Mamarosh et al. also found that the analogs could compete with mecamylamine, an indirect nicotine antagonist, in vitro. Therefore, the authors speculated that the anti-seizure activity could be due to the interaction of the phenyltropanes with a nicotinic acetylcholine receptor. Even if this speculation were true, this finding would not suggest that the phenyltropane compounds would be useful for smoking cessation. There are a large number (at least 1000) of different nicotinic acetylcholine receptors (nAChRs). The nAChRs are composed of various alpha(2–9) and beta(1–4) subunit combinations. Even now very little is known concerning the specific receptor involved in any particular pharmacological response. Some data suggest that nicotine-induced seizures appear to be mediated by the alpha-7 nicotinic receptors. Other data suggest that this class of receptors does not mediate nicotine reinforcement. Nicotine reinforcement is central to nicotine addiction. Therefore, these experiments do not suggest that these compounds would block nicotine and be useful smoking cessation reagents.

In spite of the known methods for treating smoking addiction, there remains a lack of generally effective means of treating and/or preventing smoking addiction. Accordingly, there remains a strong need for methods of treating smoking addiction.

SUMMARY OF THE INVENTION

It is an object of the present invention to provide methods and reagents for smoking cessation.

It is another object of the present invention to provide methods and reagents for treating nicotine addiction.

It is another object of the present invention to provide methods and reagents for preventing smoking addiction.

The objects of the invention, and others, are accomplished with a method of training a smoker to quit smoking, comprising administering to a smoker in need thereof an effective amount of a tropane compound represented by the formula:

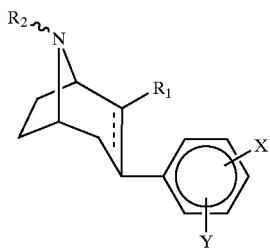

wherein
$R_1$ is $CO_2R_3$, $CONR_4R_5$, $R_6$, $CH_2R_6$,

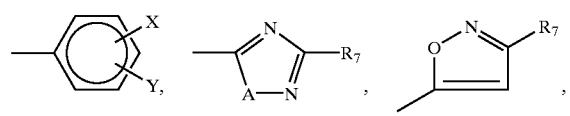

-continued

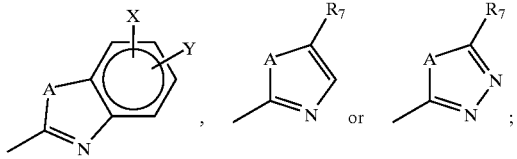

$R_3$ is H, $C_{1-6}$alkyl, $C_{3-8}$cycloalkyl or

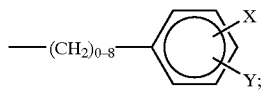

$R_4$ and $R_5$ are each independently, H, $C_{1-6}$alkyl, $C_{2-6}$alkene, $C_{2-6}$alkyne, $CH_2$-CO—phenyl, phenyl, phenyl substituted with 1–3 of $C_{1-6}$ alkyl, $C_{2-6}$alkene, $C_{2-6}$alkyne or $C_{1-6}$ alkoxy, hydroxy, $CH_2OH$, $C_{1-6}$alkoxy, phenoxy, amino, amino substituted with 1 or 2 $C_{1-6}$ alkyl, $C_{2-6}$alkene, $C_{2-6}$alkyne, $C_{1-6}$alkoxy, $C_{1-8}$acyl, phenyl, or phenoxy, or $R_4$ and $R_5$ may combine to form, together with the nitrogen atom to which they are bonded, a cyclic structure selected from the group consisting of a pyrrolidinyl group, morpholinyl group, piperidinyl group and a group represented by the formula

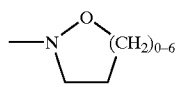

$R_6$ is OH, H, $C_{1-6}$alkyl, $C_{3-8}$cycloalkyl, $C_{1-6}$alkoxy, Cl, Br, I, CN, $NH_2$, $NHC_{1-6}$alkyl, $N(C_{1-6}$alkyl$)_2$, OCO—$C_{1-6}$alkyl, OCO—$C_{1-3}$alkylaryl, $CO_2$—$C_{1-6}$alkyl, $CO_2$—$C_{1-3}$alkylaryl or substituted phenoxy;

$R_7$ is H, $C_{1-6}$alkyl, $C_{3-8}$cycloalkyl, $C_{1-6}$alkoxy, $C_{2-6}$alkynyl, halogen, amino or;

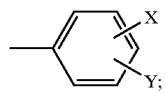

A is S, O or NH;
$R_2$ is H, $C_{1-5}$alkyl, halogenated $C_{1-6}$alkyl, $C_{2-6}$alkenyl or $(CH_2)_nCO_2R_x$ where n is integer of 1 to 8 and $R_x$ is $C_{1-6}$alkyl;
each X is, independently, H, $C_{1-6}$alkyl, $C_{3-8}$cycloalkyl, $C_{1-6}$alkoxy, $C_{2-6}$alkynyl, phenyl, $C_{1-6}$-phenyl, halogen, amino, or acylamido, $CR_z$=$CR_zR_z$, $CR_zR_z$—CH=$CR_zR_z$, C=—$CR_z$, C(=$R_zR_z$)$R_z$;
each $R_z$ is, independently, H, $C_{1-6}$alkyl, phenyl, substituted phenyl, $CH_2OH$, $C_{1-6}$-phenyl;
each Y is, independently, H, I, Br, Cl, F, CN, $CF_3$, $NO_2$, $N_3$, $OR_8$, $CO_2NH_2$, $CO_2R_8$, $C_{1-6}$alkyl, $NR_9R_{10}$, $NHCOR_{11}$ or $NHCO_2R_{12}$;
$R_8$ is H or $C_{1-6}$alkyl; and
$R_9$, $R_{10}$ $R_{11}$ and $R_{12}$ are each, independently, H or $C_{1-6}$alkyl,
or X and Y, taken together with the phenyl group to which they are bonded, form a 2-naphthyl group,
the dotted line between $C_2$ and $C_3$ represents a single or double bond,
or a pharmaceutically acceptable salt thereof.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 5: Failure of nicotine antagonists DHβE and mecamylamine in blocking cocaine-induced increase in locomotor activity in mice, antagonists were administered s.c. 10 min before cocaine (15 mg/kg) i.p. injection. Ten minutes later, mice were placed into activity cages for 30 min. Each point represents mean ±S.E. of 8 to 12 mice. Coc, =cocaine; Meca=mecamylamine. *Statistically different from vehicle at P<0.5.

DETAILED DESCRIPTION OF THE INVENTION

Figure 1:
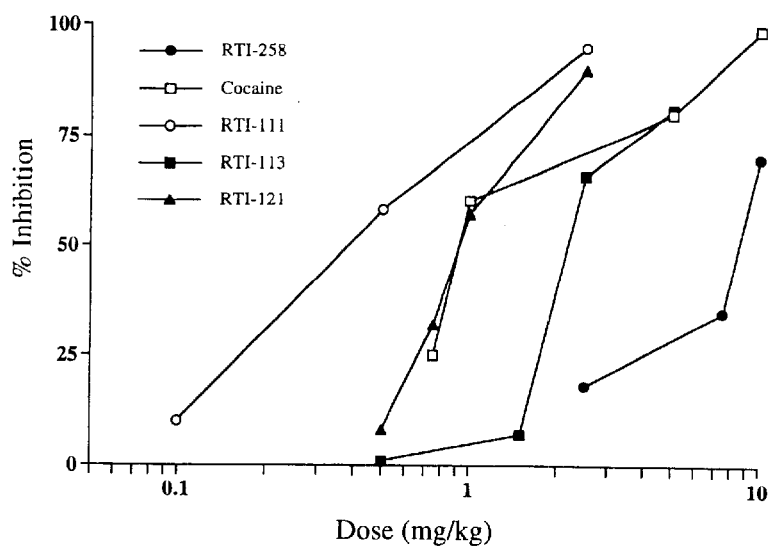
FIG. 1: Comparison of cocaine and its analogs for blockade of antinociception induced by nicotine. Antagonists were administered i.p. 10 min before nicotine (2.5 mg/kg) was administered s.c, and mice were tested 5 min after nicotine injection in tail-flick test. Each point represents mean ±S.E. of 8 to 12 mice.
Figure 2:
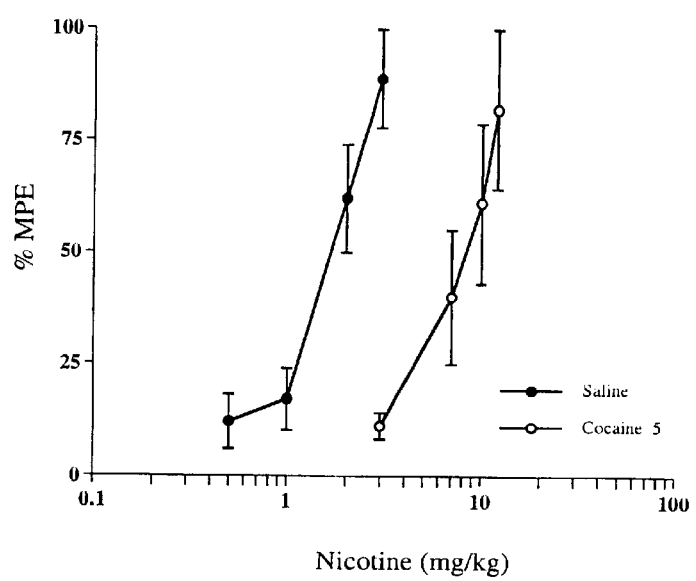
FIG. 2: Dose-response relationship of nicotine-induced antinociception and its antagonism by cocaine. Cocaine (5 mg/kg) was administered i.p. 10 min before nicotine, and mice were tested 5 min after nicotine injection in tail-flick test. Each point represents mean ±S.E. of 8 to 12 mice.

The present invention is based, in part, on the recognition that phenyltropanes can be used to antagonize/block nicotine reinforcement. As one skilled in the art will readily appreciate, the act of smoking involves both physiological responses, e.g., nicotine-induced biochemical signals in the brain, and sensory and psychological signals, e.g., smell, taste, the ritualization of smoking. Over time, the reinforcing activity of nicotine becomes closely linked to the sensory and psychological responses associated with smoking. As a result, the design of methods of assisting smokers to cease smoking preferably allows nicotine reinforcement to be dissociated from the sensory and psychological aspects of smoking.

The present invention is based on the recognition that the phenyltropane compounds function as nicotine antagonists, but that this nicotine antagonism (antinociception) does not correlate with affinity for the dopamine, serotonin or norepinephrine transporters. In addition, this nicotine antagonism is highly relevant to smoking cessation. Not wishing to be bound by any particular theory, the experiments presented in the following Examples appear to suggest that the phenyltropanes interact with the $\alpha_4\beta_2$ nicotinic receptor subtype. The phenyltropanes blocked nicotine-induced antinociception, which is mediated by the $\alpha_4\beta_2$ nicotinic receptor subtype (Damaj et al., J. Pharmacol. Exp. Ther. 284: 1058–1065). It is recognized that the that the $\alpha_4\beta_2$ receptors are responsible for increased dopamine release in response to nicotine (see Sharples et al., J. Neuroscience 23:2783–2791, 2000). In addition, it is recognized that dopamine mediates nicotine reinforcement. Accordingly, antinociception can be used as a surrogate for nicotine reinforcement.

Without being limited to any theory, it is believed that the phenyltropane compounds of the present invention are useful in training a smoker to cease smoking. In the method of the present invention, the phenyltropanes satisfy the smoker's craving for nicotine, but also decouple the physiological effects from the act of smoking. Thus, the phenyltropanes of the present invention may have function as a nicotine substitute (nicotine agonist) and/or may block reinforcement (nicotine antagonist). As a result, the smoker is able to reduce the amount of smoking, and may be able to quit smoking altogether.

The description above emphasizes the use of the phenyltropane compounds in relation to treating smoking addiction. The phenyltropane compounds may also be used to treat addiction to smokeless tobacco, e.g., chewing tobacco.

The method of the present invention comprises administering a tropane compound of amount of a tropane compound represented by the formula:

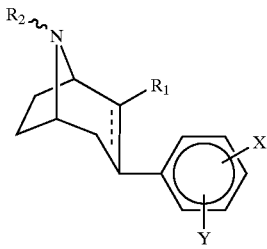

wherein
$R_1$ is $CO_2R_3$, $CONR_4R_5$, $R_6$, $CH_2R_6$,

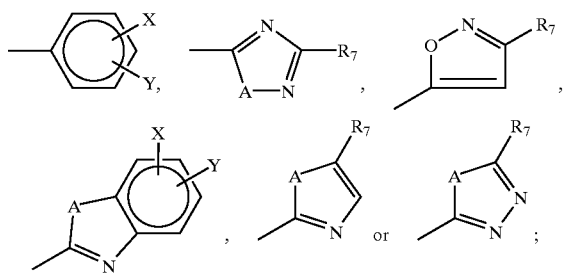

$R_3$ is H, $C_{1-6}$alkyl, $C_{3-8}$cycloalkyl or

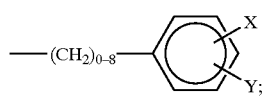

$R_4$ and $R_5$ are each independently, H, $C_{1-6}$alkyl, $C_{2-6}$alkene, $C_{2-6}$alkyne, $CH_2$—CO-phenyl, phenyl, phenyl substituted with 1–3 of $C_{1-6}$alkyl, $C_{2-6}$alkene, $C_{2-6}$alkyne or $C_{1-6}$ alkoxy, hydroxy, $CH_2OH$, $C_{1-6}$alkoxy, phenoxy, amino, amino substituted with 1 or 2 $C_{1-6}$alkyl, $C_{2-6}$alkene, $C_{2-6}$alkyne, $C_{1-6}$alkoxy, $C_{1-8}$acyl, phenyl, or phenoxy, or $R_4$ and $R_5$ may combine to form, together with the nitrogen atom to which they are bonded, a cyclic structure selected from the group consisting of a pyrrolidinyl group, morpholinyl group, piperidinyl group and a group represented by the formula

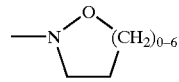

$R_6$ is OH, H, $C_{1-6}$alkyl, $C_{3-8}$cycloalkyl, $C_{1-6}$alkoxy, Cl, Br, I, CN, $NH_2$, $NHC_{1-6}$alkyl, $N(C_{1-6}$alkyl$)_2$, OCO—$C_{1-6}$alkyl, OCO—$C_{1-3}$alkylaryl, $CO_2$—$C_{1-6}$alkyl, $CO_2$—$C_{1-3}$alkylaryl, or substituted phenoxy;
$R_7$ is H, $C_{1-6}$alkyl, $C_{3-8}$cycloalkyl, $C_{1-6}$alkoxy, $C_{2-6}$alkynyl, halogen, amino or;

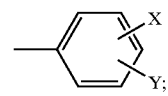

A is S, O or NH;
$R_2$ is H, $C_{1-5}$alkyl, halogenated $C_{1-6}$alkyl, $C_{2-6}$alkenyl or $(CH_2)_nCO_2R_x$, where n is an integer of 1 to 8 and R is $C_{1-6}$alkyl;
each X is, independently, H, $C_{1-6}$alkyl, $C_{3-8}$cycloalkyl, $C_{1-6}$alkoxy, $C_{2-6}$alkynyl, phenyl, $C_{1-6}$-phenyl, halogen, amino, or acylamido, $CR_z=CR_zR_z$, $CR_zR_z$—$CH=CR_zR_z$, $C\equiv CR_z$, $C(=R_zR_z)R_z$;
each $R_z$ is, independently, H, $C_{1-6}$alkyl, phenyl, substituted phenyl, $CH_2OH$, $C_{1-6}$-phenyl;
each Y is, independently, H, I, Br, Cl, F, CN, $CF_3$, $NO_2$, $N_3$, $OR_8$, $CO_2NH_2$, $CO_2R_8$, $C_{1-6}$alkyl, $NR_9R_{10}$ $NHCOR_{11}$ or $NHCO_2R_{12}$;
$R_8$ is H or $C_{1-6}$alkyl; and
$R_9$, $R_{10}$, $R_{11}$ and $R_{12}$ are each, independently, H or $C_{1-6}$alkyl,
or X and Y, taken together with the phenyl group to which they are bonded, form a 2-naphthyl group,
the dotted line between $C_2$ and $C_3$ represents a single or double bond,
or a pharmaceutically acceptable salt thereof.

In a preferred embodiment, the compound used in the present method bears a group $R_2$ of H. Compounds where $R_2$ is H may exhibit higher activity in treating nicotine addiction.

In another preferred embodiment, the compounds bear an $R_1$ group of $CO_2R_3$ or $CONHR_4R_5$, an $R_2$ group of H or $C_{1-5}$alkyl, an X group of H, $C_{1-6}$alkyl, halogen or amino, a Y group of H, $C_{1-6}$alkyl or halogen. In this embodiment, $R_3$ is preferably H $C_{1-6}$alkyl $C_{3-8}$ cycloalkyl, or phenyl; $R_4$ and $R_5$ are each independently, H or $C_{1-6}$alkyl or combine to form the cyclic structure described above; and the halogen is I, Br or Cl. Especially preferred alkyl groups have 1 to 4 carbon atoms.

When a single bond connects the $C_2$ and $C_3$ positions of the tropane ring, the $R_1$ group and the phenyl substituent at the 3-position may have $\alpha$ or $\beta$ stereochmistry. Preferably, the phenyl substituent has 3$\beta$ stereochmeistry. In one particularly preferred embodiment, the $R_1$ group and the phenyl substituent at the 3-position are on the same face of the ring (cis). In another particularly preferred embodiment, the $R_1$ group at $C_2$ and the group and phenyl group at $C_3$ are on the same face of the ring, where the phenyl substituent has 3β stereochmeistry.

Compounds that may also be used in the present invention are those represented by the formula described above in which the phenyl group at the 3-position is linked to the tropane ring by one of —$CH_2$—, —S—, —CO—O— or O—CO— moiety. Compounds that may also be used in the present invention are those represented by the formula described above in which the phenyl group at the 3-position is replaced with a pyridine group, e.g., a 2-, 3- or 4-pyridyl group. The pyridyl group may be substituted by X and Y in the same manner as the phenyl group in the formula above.

The compounds are illustrated with the group $R_2$ of undefined stereochemistry, such that the $R_2$ group may be on the opposite or same side of the bridging nitrogen as the $C_2$ and $C_3$ substitutions.

The compound depicted as above is shown as a single enantiomeric compound, however, both enantiomers are within the scope of the present invention, such as a racemic mixture. Moreover, it is within the specific scope of the present invention to administer compounds which are enantiomerically enriched in a single enantiomer. Within the context of the present invention enrichment in a single enantiomer may comprise an enantiomeric excess (e.e.) of $\geq 55\%$, even more preferably $\geq 70\%$, even more preferably $\geq 80\%$, even more preferably $\geq 90\%$, even more preferably $\geq 95\%$, even more preferably $\geq 98\%$.

An enantiomerically enriched composition may be prepared by conventional methods known to those of ordinary skill in the art, such as by using an enantiomerically enriched starting material or by resolution of a racemic mixture or a mixture of a lower enantiomeric purity. Resolution may be conducted by conventional methods known to those of skill in the art, such as by chiral chromatography, formation of diasteriomeric derivatives followed by separation, or enantioselective crystallization.

As described above, it is within the context of the present invention to administer a composition enriched in a single entantiomer. In one embodiment of the present invention, the composition is enriched in the (+) enantiomer. In another embodiment of the present invention, the composition is enriched in the (−) enantiomer. Administration of a composition enriched in a single enantiomer offers the advantage of maximizing the effect of treating nicotine addiction, while minimizing unwanted activities.

Preparation of Tropane Compounds

The compounds used in the method of the present invention may be prepared by conventional methods known to those of ordinary skill in the art. For examples of compounds that may be used in the present invention, and methods of preparation thereof, see U.S. Pat. Nos. 5,128,118; 5,380,848; 5,413,779; 5,496,953; 5,736,123; WO 92/02260; U.S. patent application Ser. No. 09/083,043, filed May 22, 1998; U.S. patent application Ser. No. 08/706,263, filed Sep. 4, 1996; U.S. patent application Ser. No. 08/506,541, filed Jul. 24, 1995, the relevant portions of which, which describe specific compounds and the preparation thereof, are hereby incorporated by reference. Examples of compounds that may be used in the present invention are shown below.

The compounds may be used in the form of a pharmaceutically acceptable salt via protonation of the amine with a suitable acid. The acid may be an inorganic acid or an organic acid. Suitable acids include, for example, hydrochloric, hydroiodic, hydrobromic, sulfuric, phosphoric, citric, acetic and formic acids.

Non-limiting examples of compounds which may be used in the present invention:

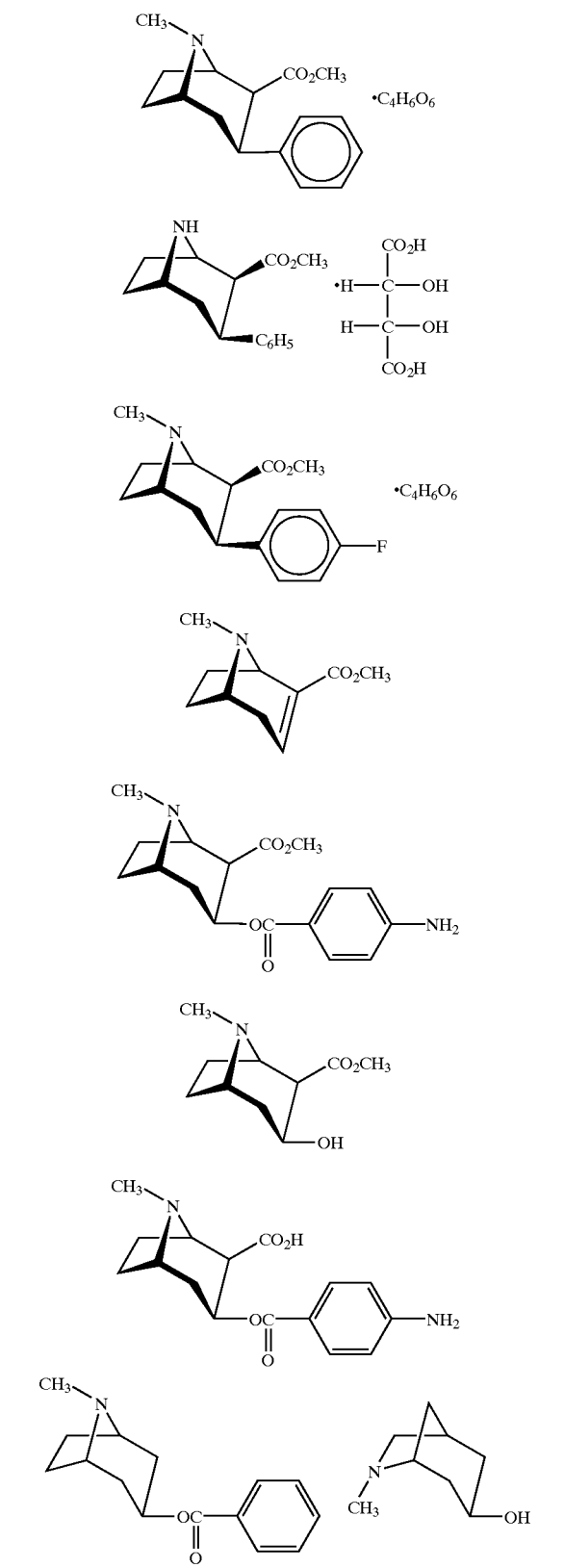

-continued
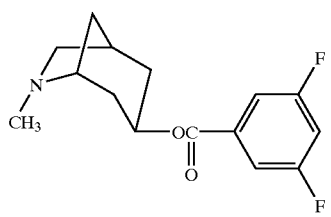
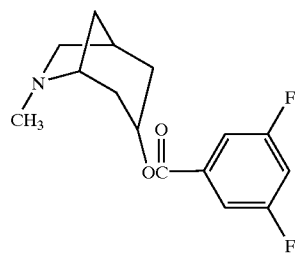
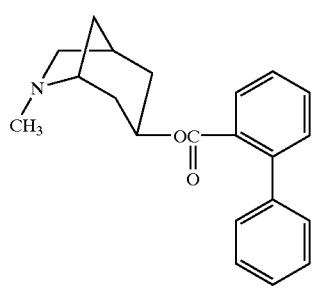
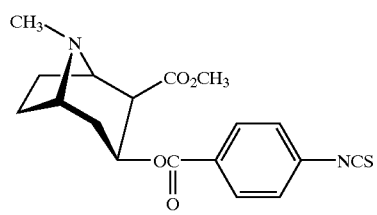
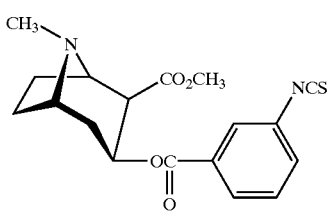
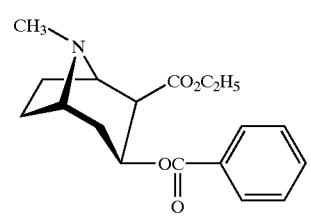
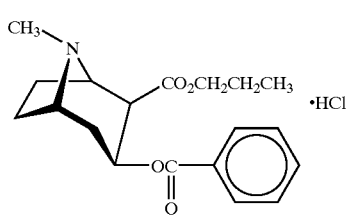
-continued
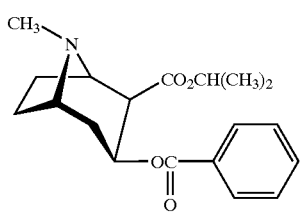
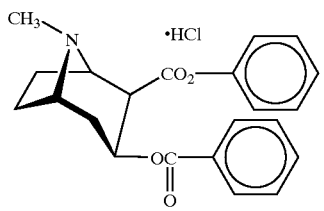
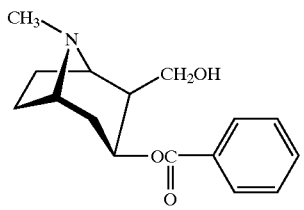
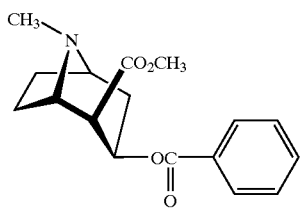
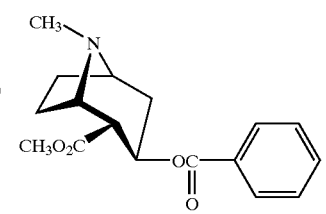
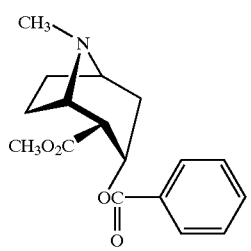
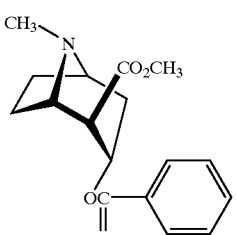
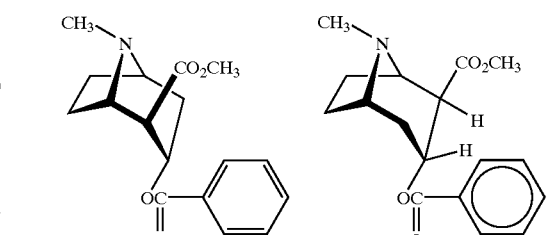
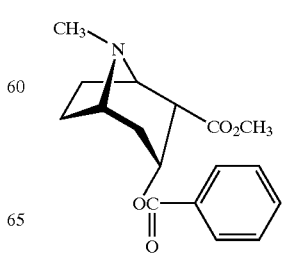
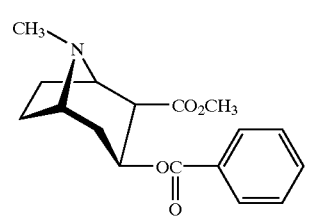

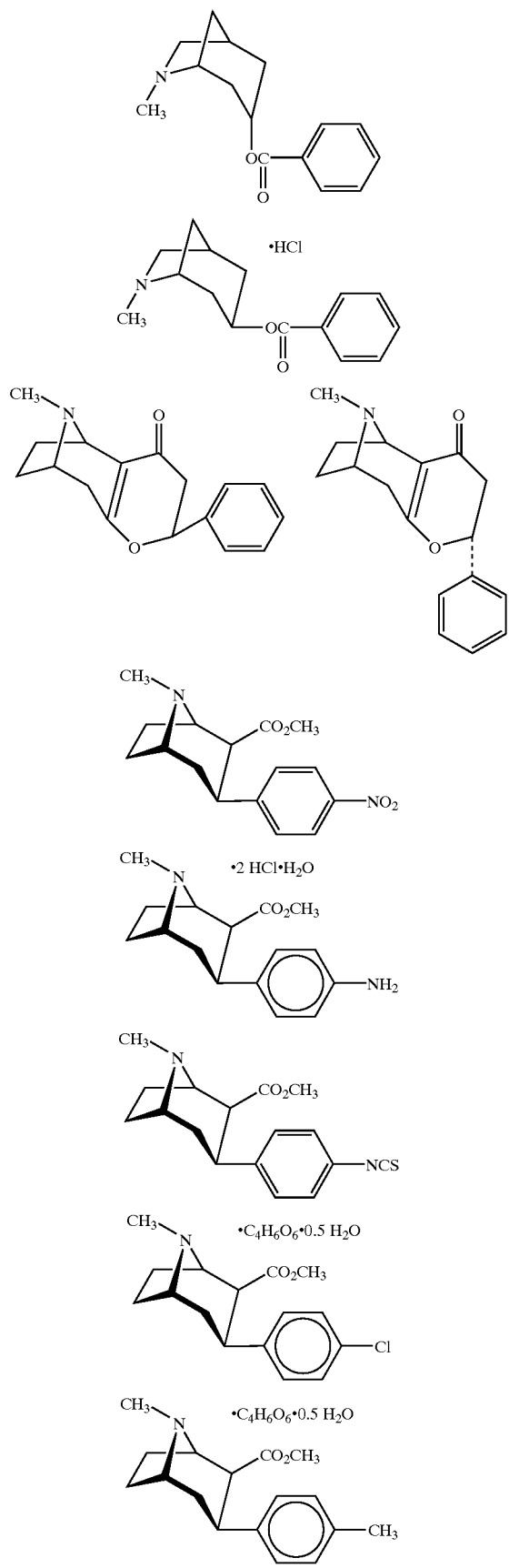
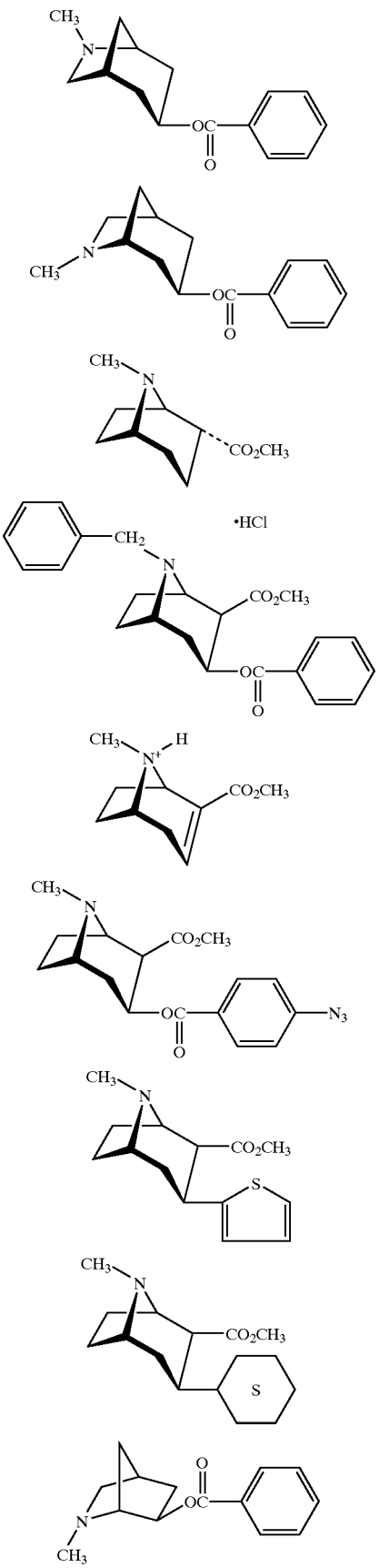

-continued
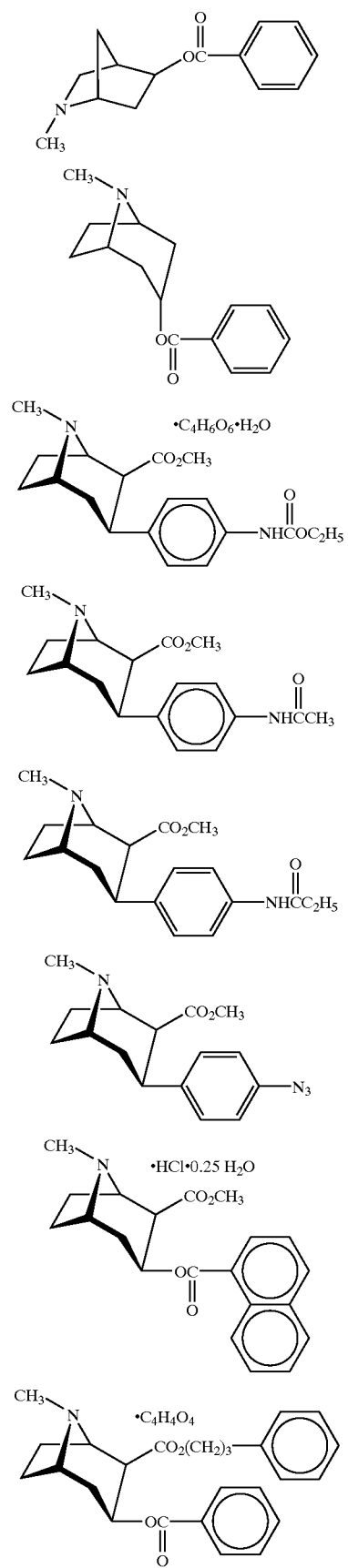
-continued
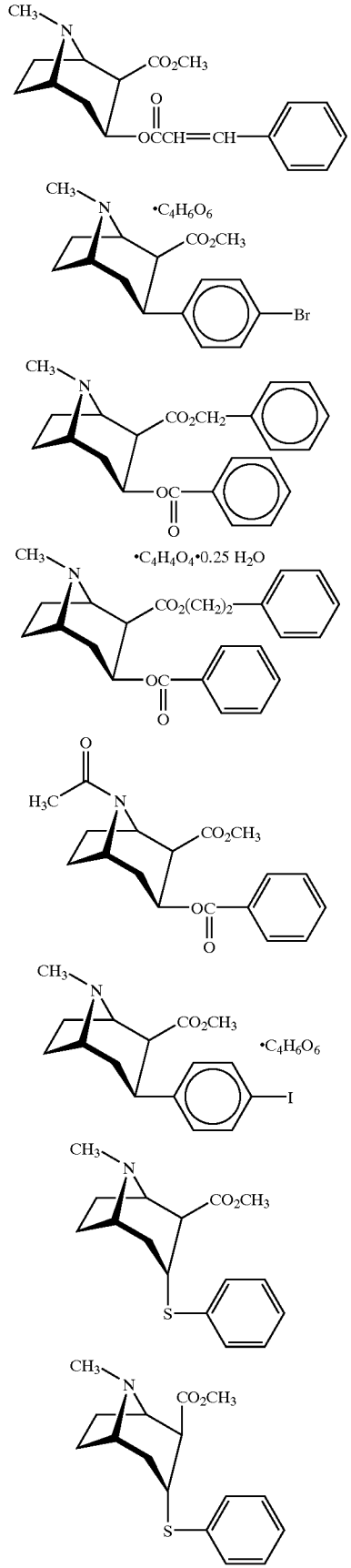

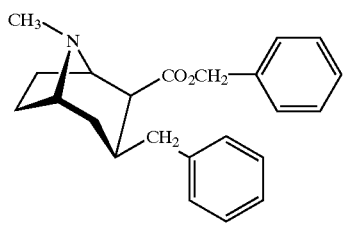
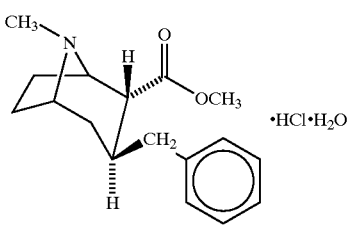
·HCl·H₂O
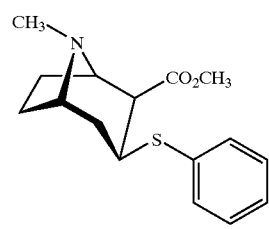
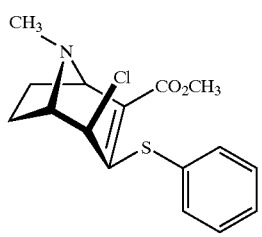
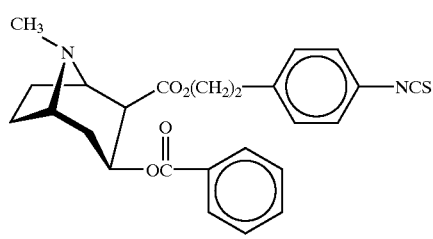
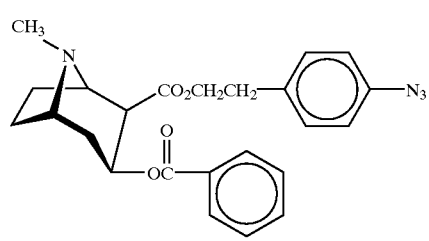
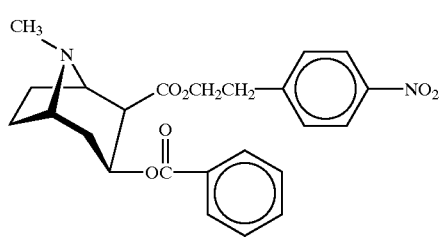
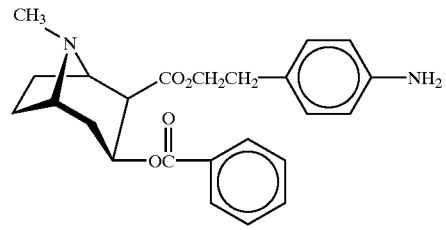
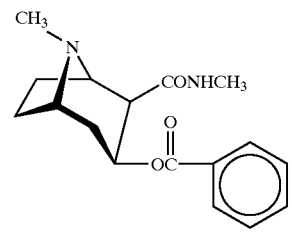
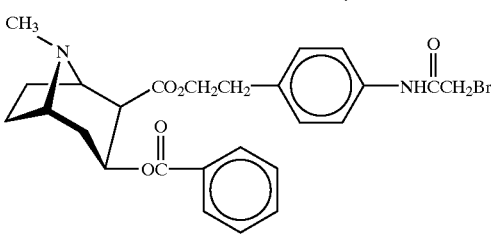
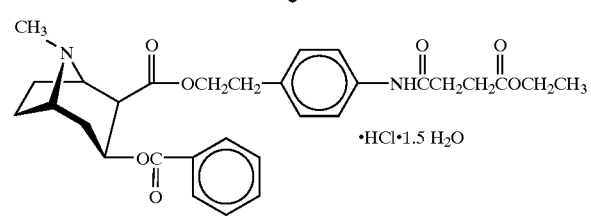
·HCl·1.5 H₂O
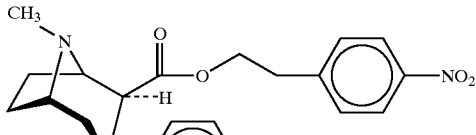
·HCl·0.75 H₂O
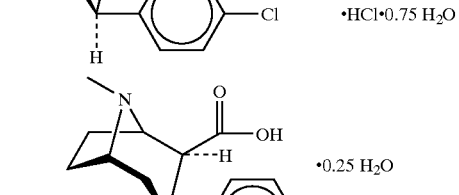
·0.25 H₂O
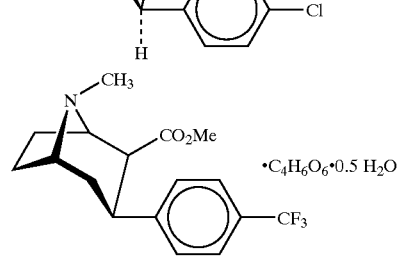
·C₄H₆O₆·0.5 H₂O
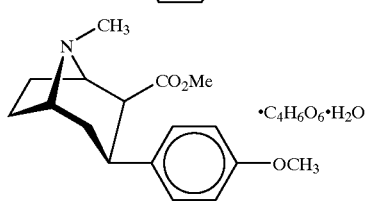
·C₄H₆O₆·H₂O

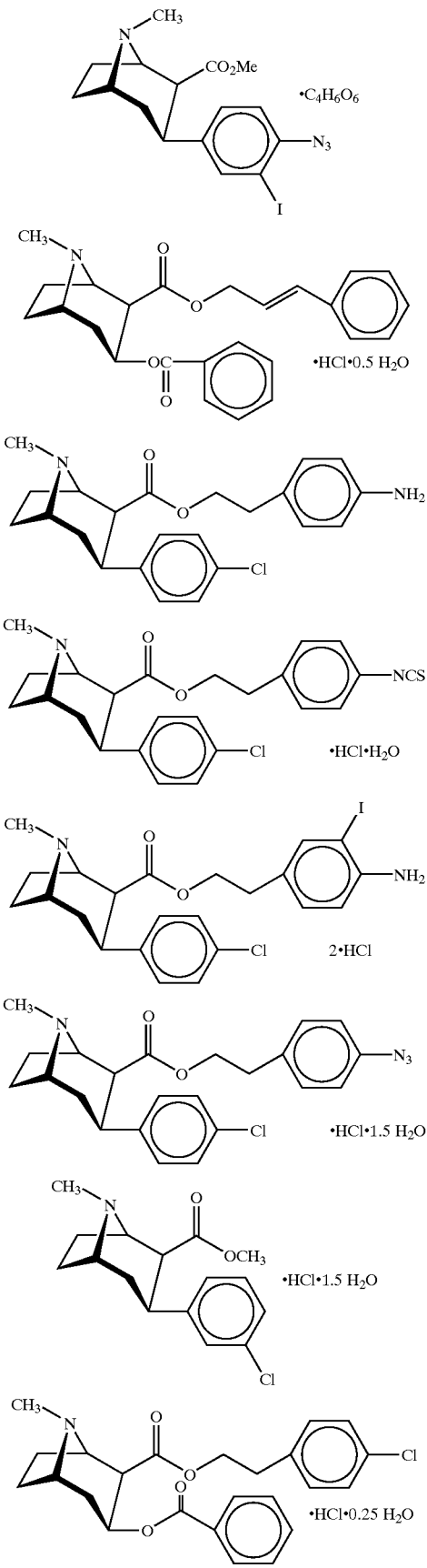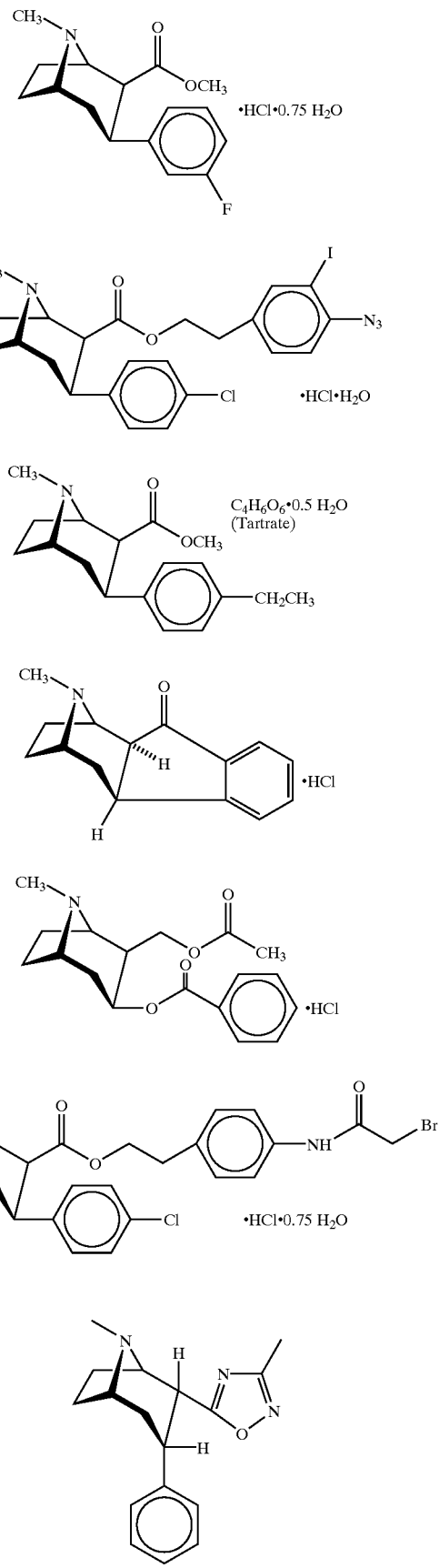

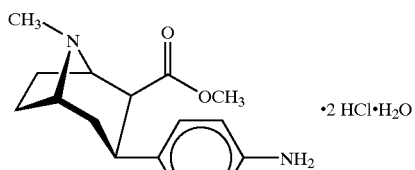 •2 HCl•H₂O
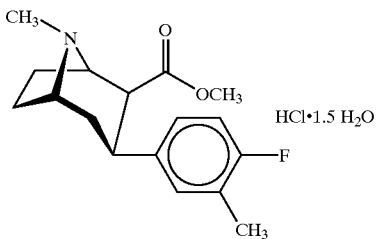 HCl•1.5 H₂O
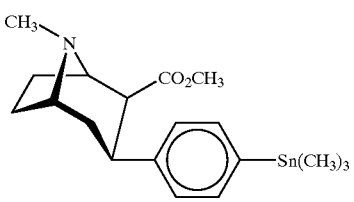
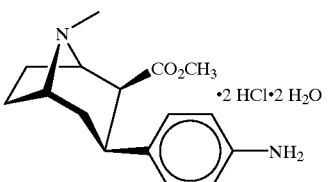 •2 HCl•2 H₂O
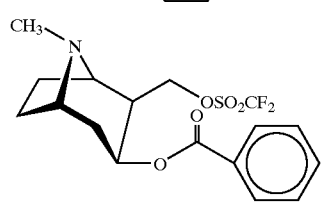
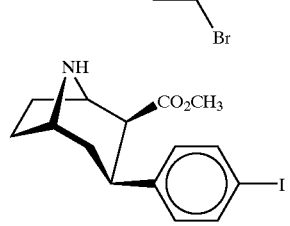
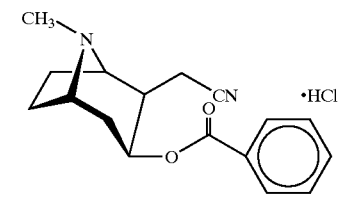 •HCl
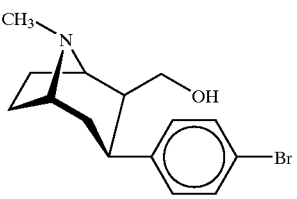
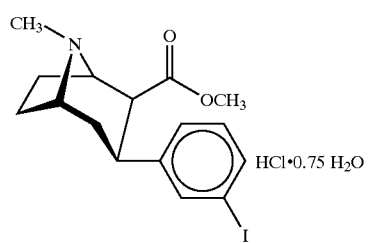 HCl•0.75 H₂O
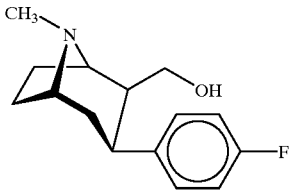
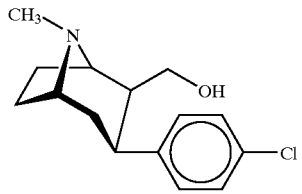
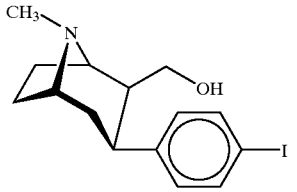
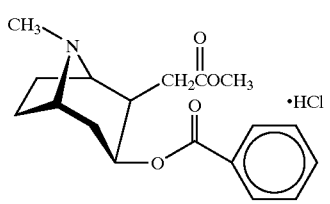 •HCl
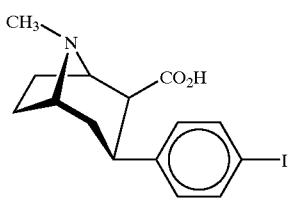
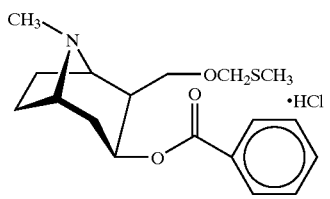 •HCl
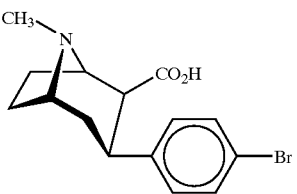

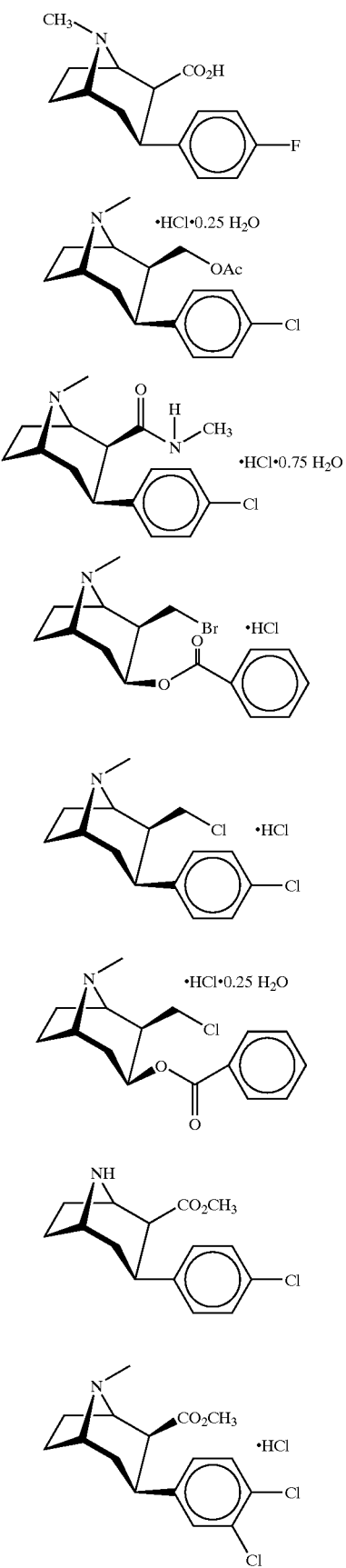
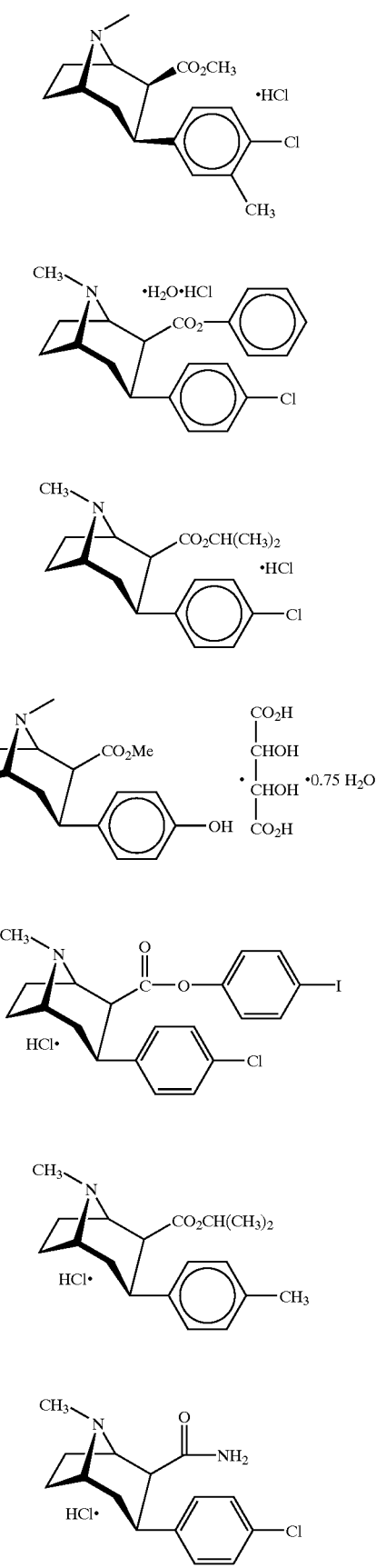

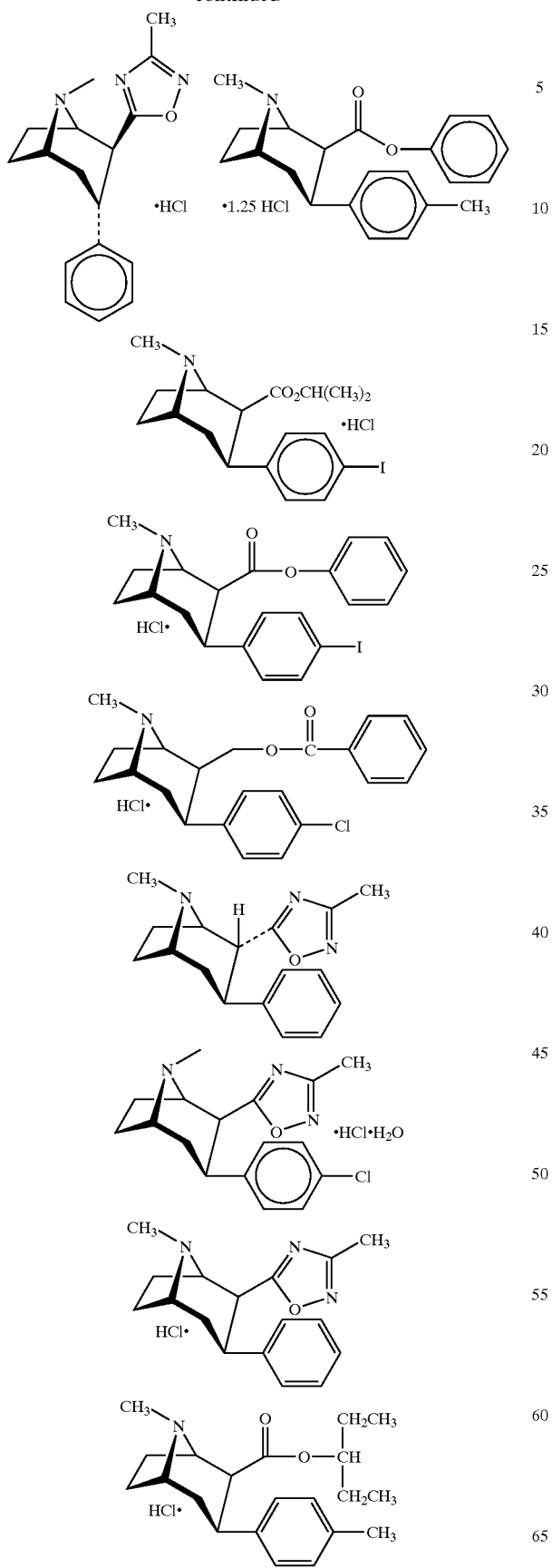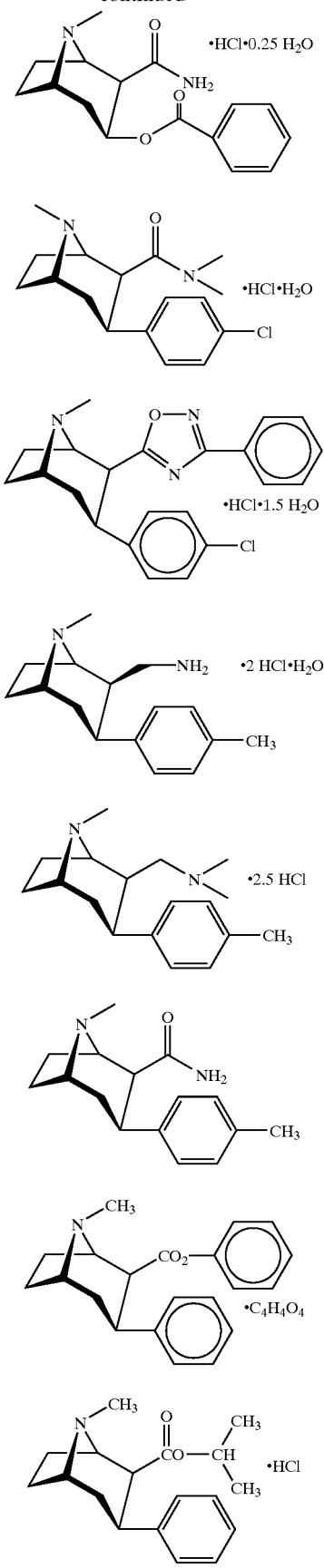

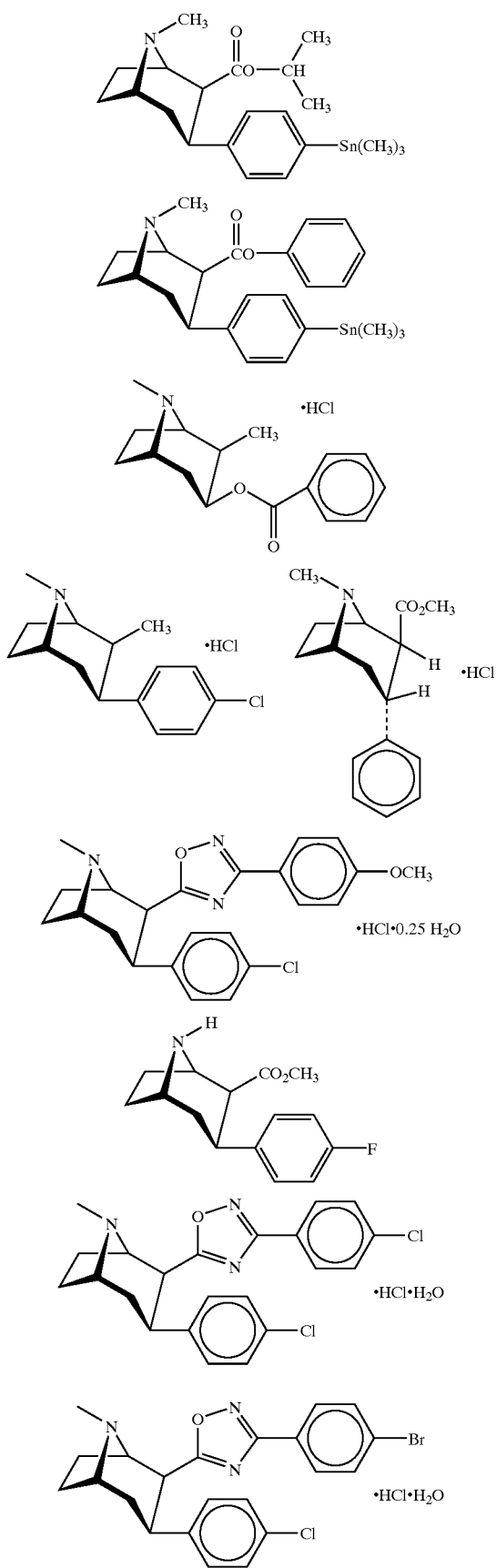
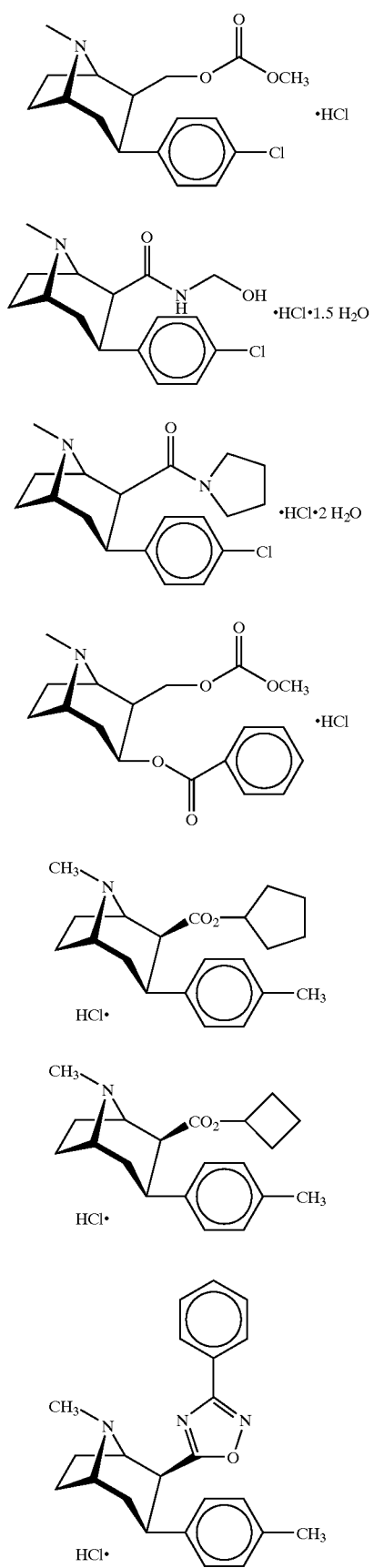

-continued
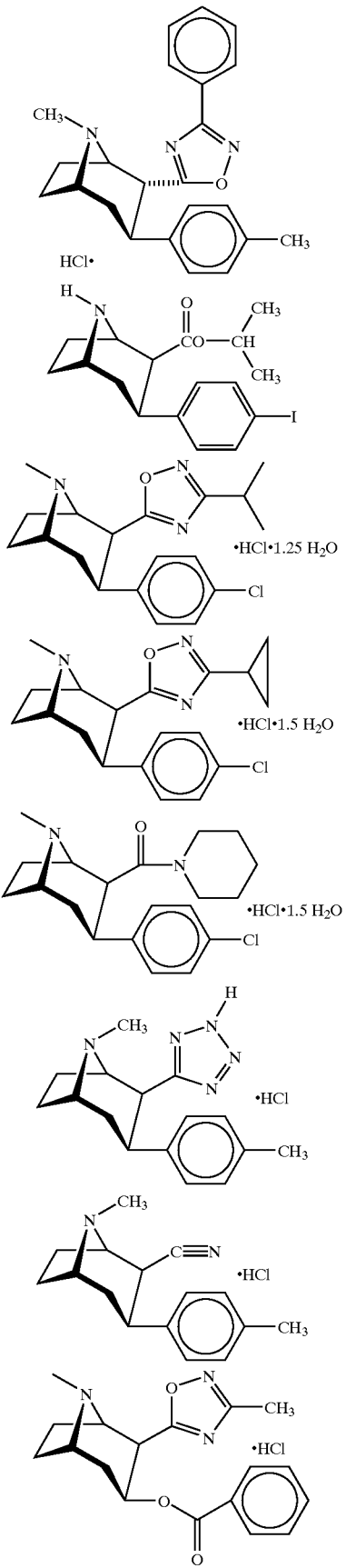
-continued
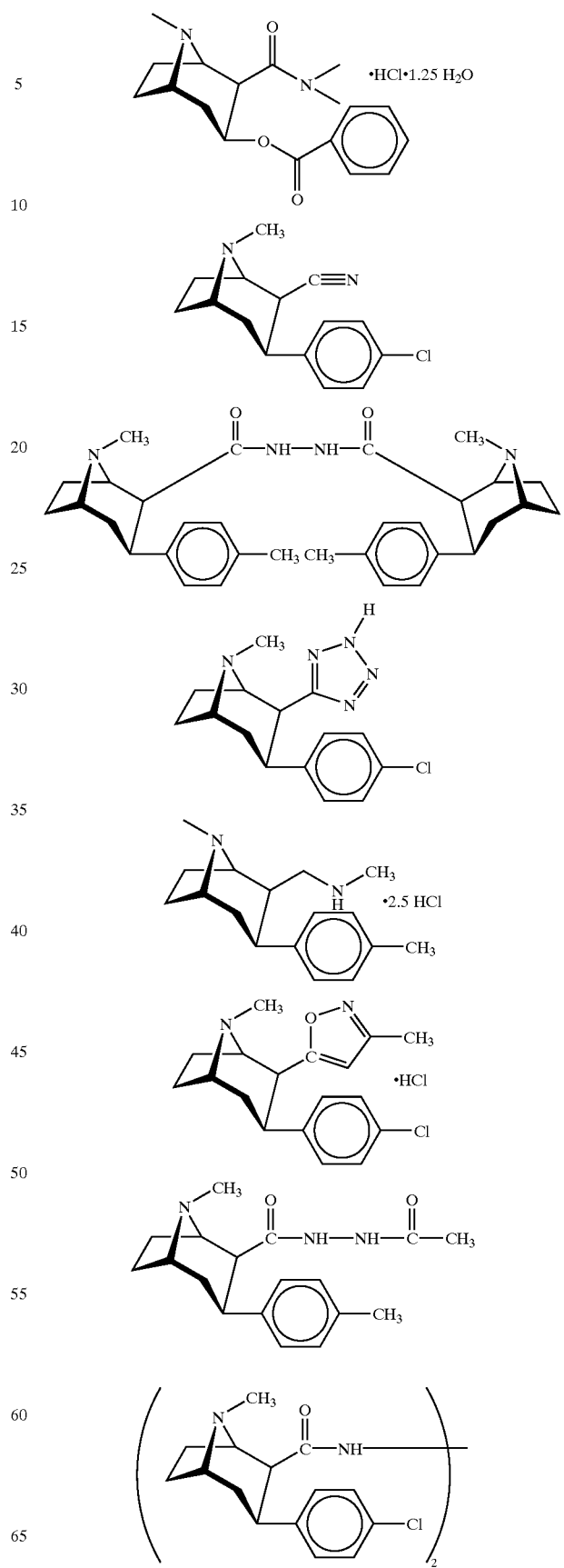

-continued
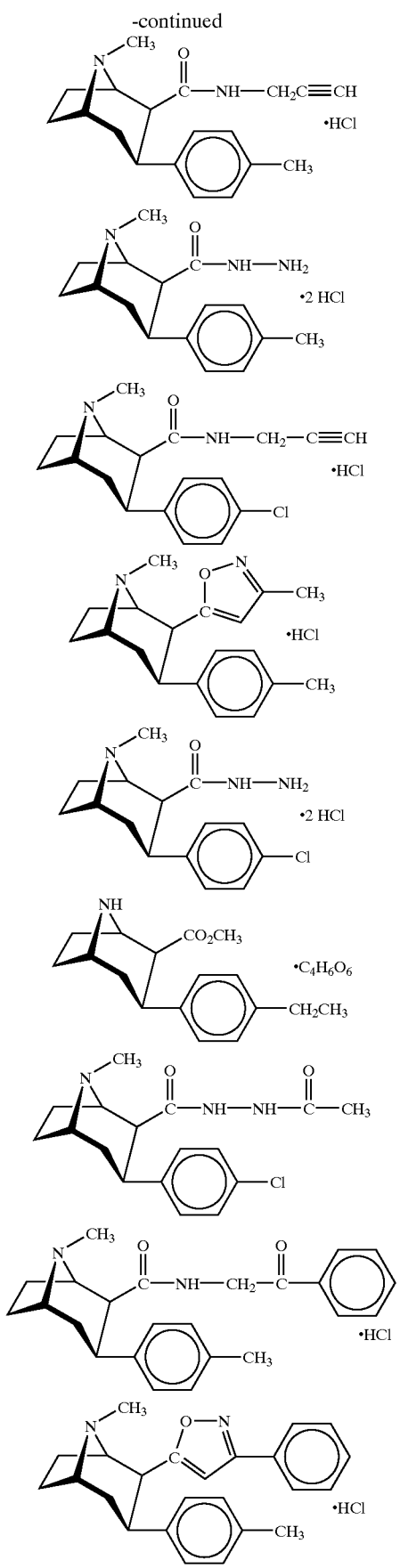
-continued
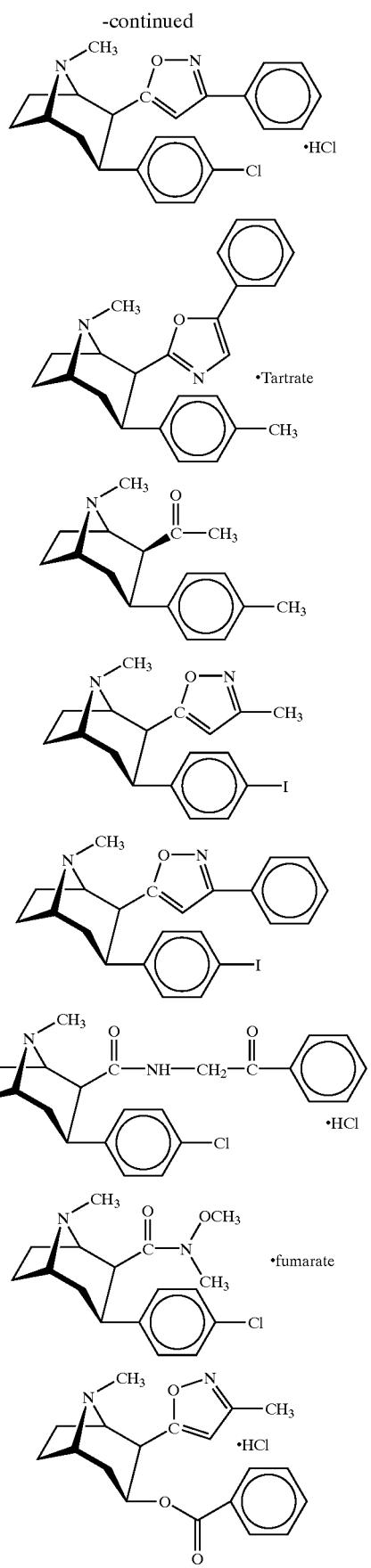

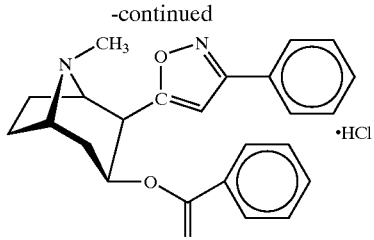 •HCl
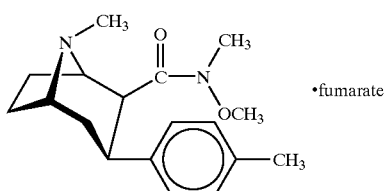 •fumarate
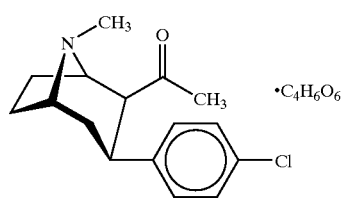 •C₄H₆O₆
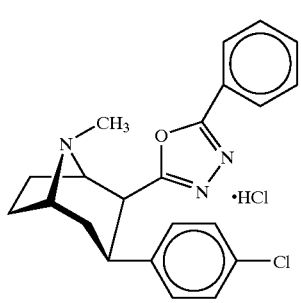 •HCl
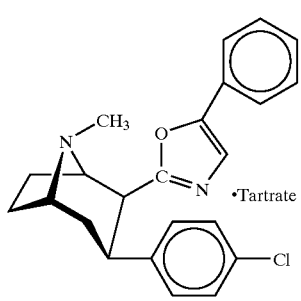 •Tartrate
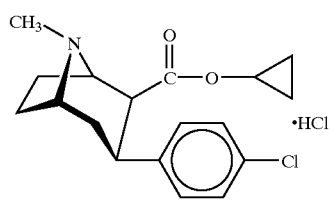 •HCl
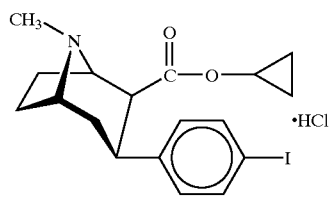 •HCl
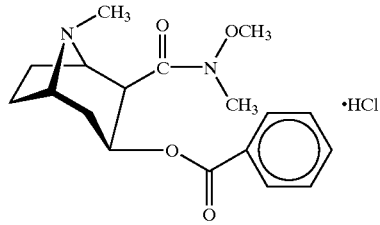 •HCl
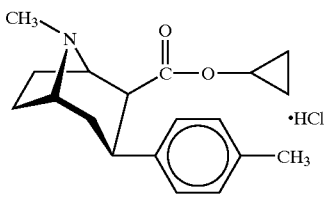 •HCl
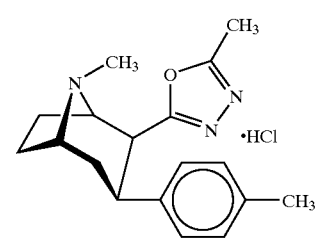 •HCl
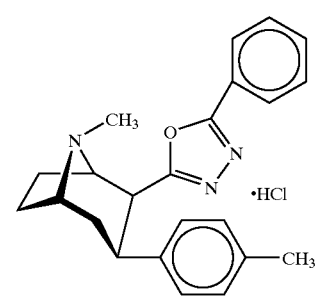 •HCl
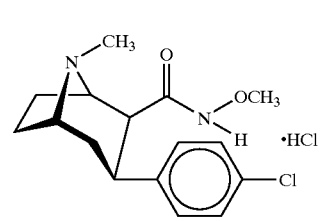 •HCl
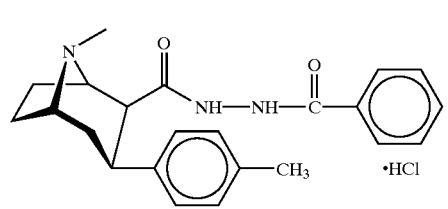 •HCl
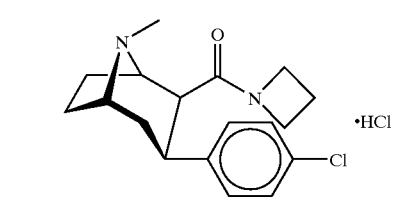 •HCl

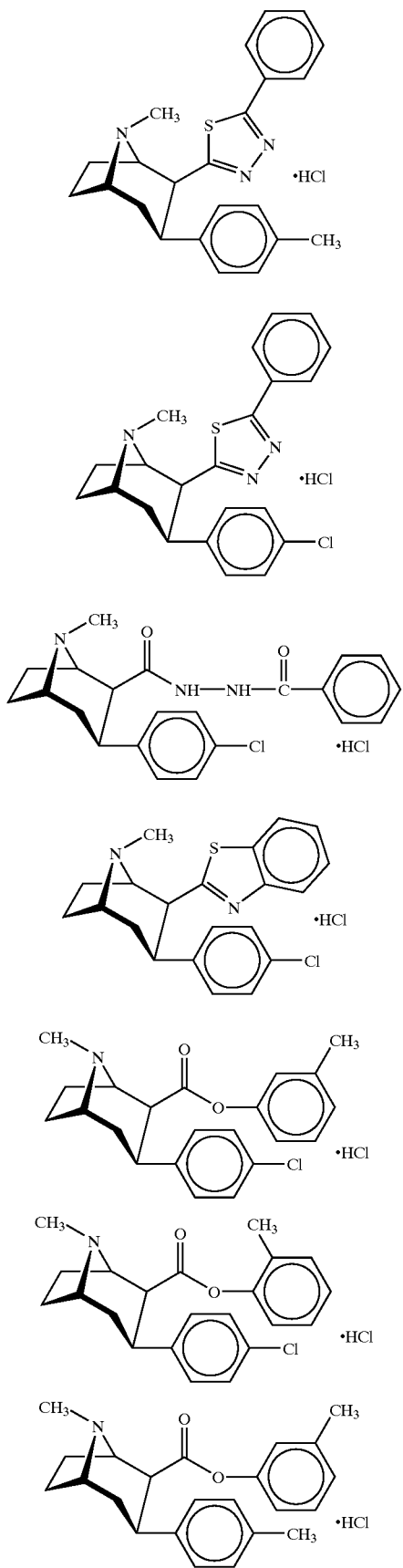
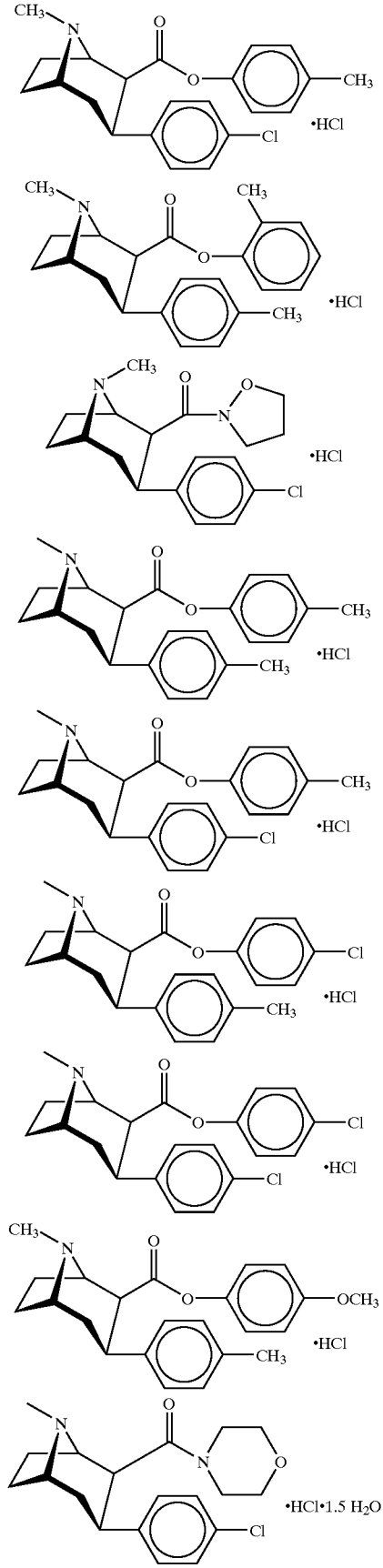

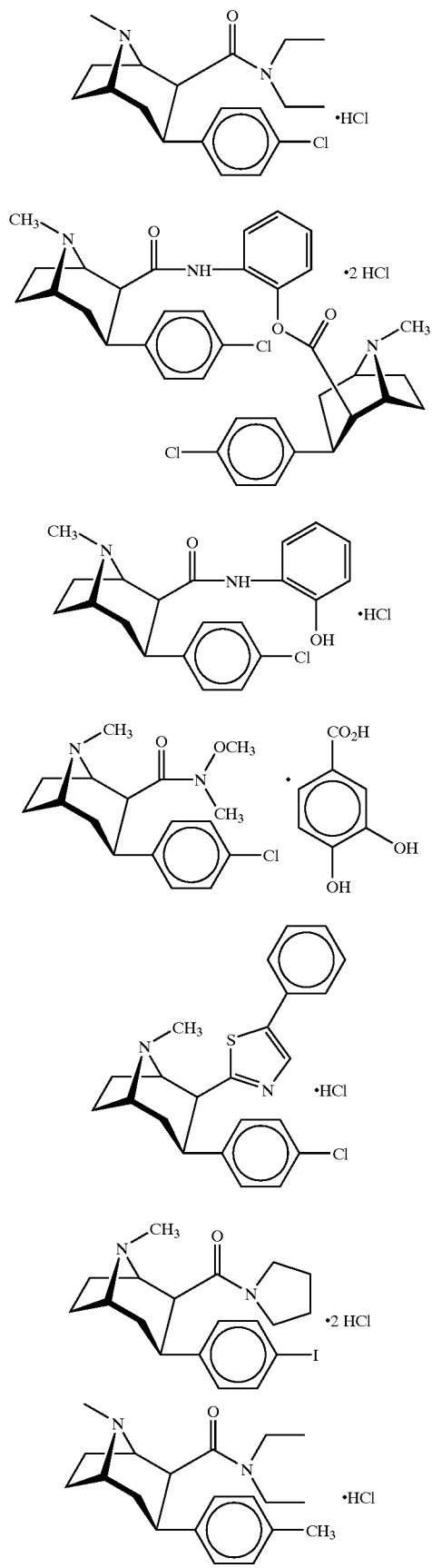
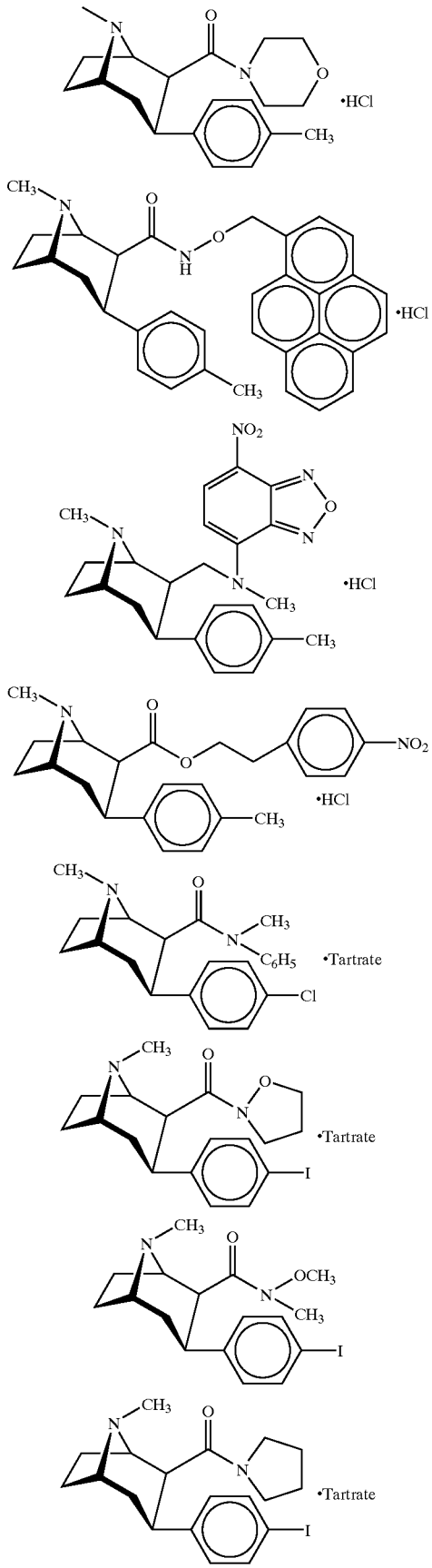

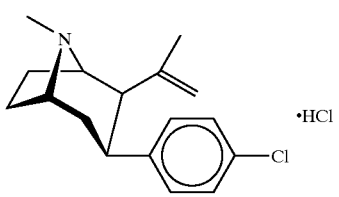
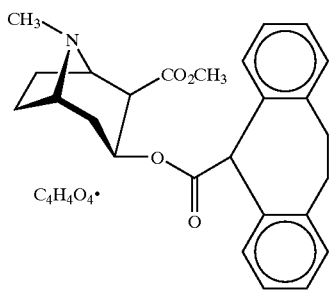
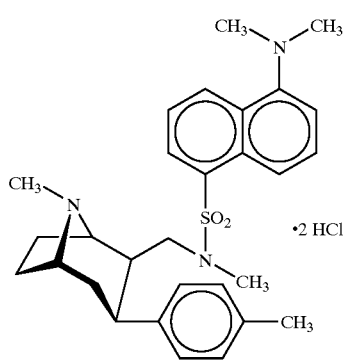
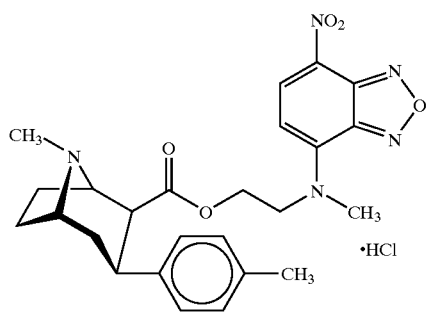
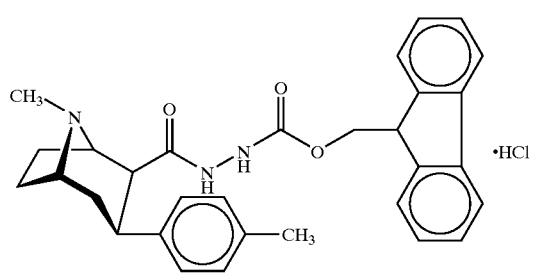
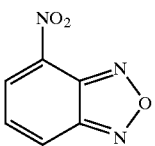
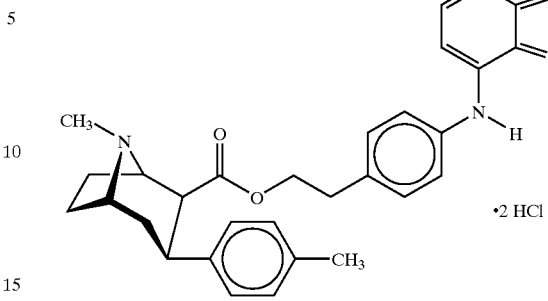
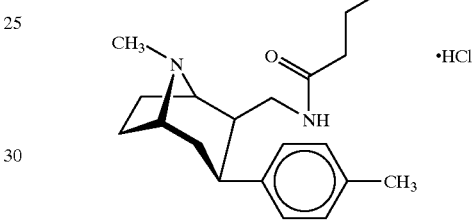
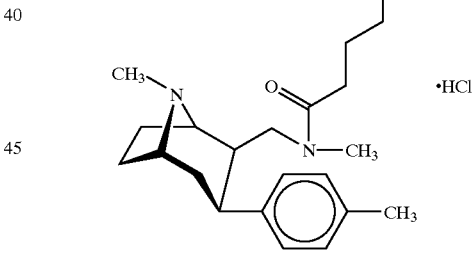
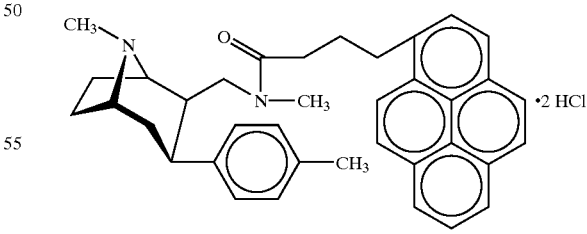
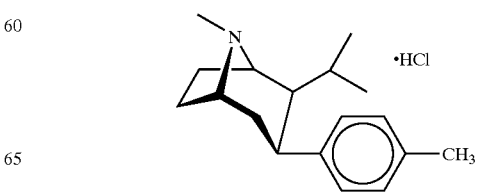

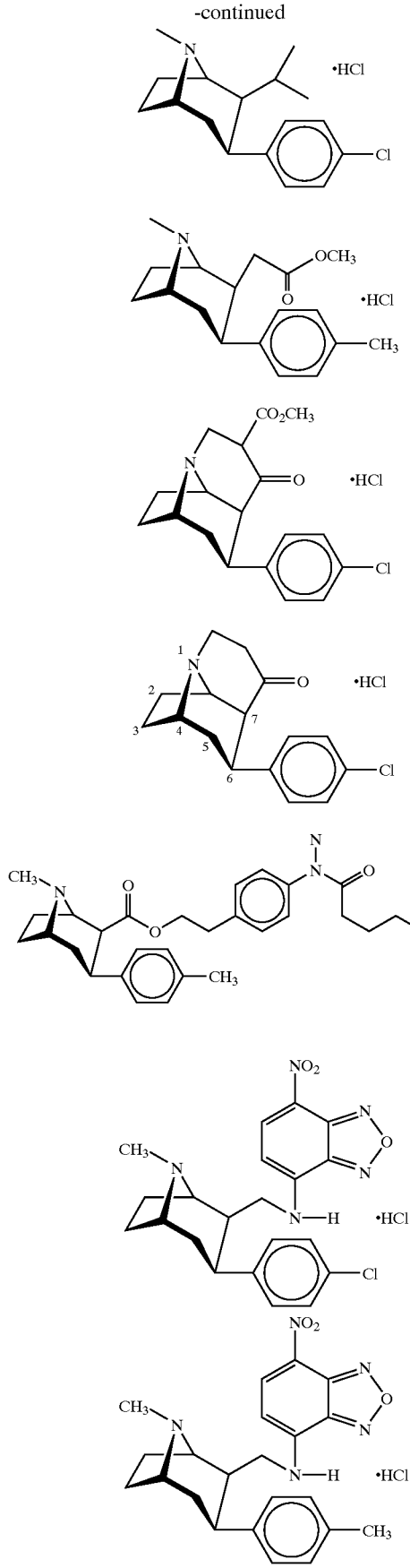
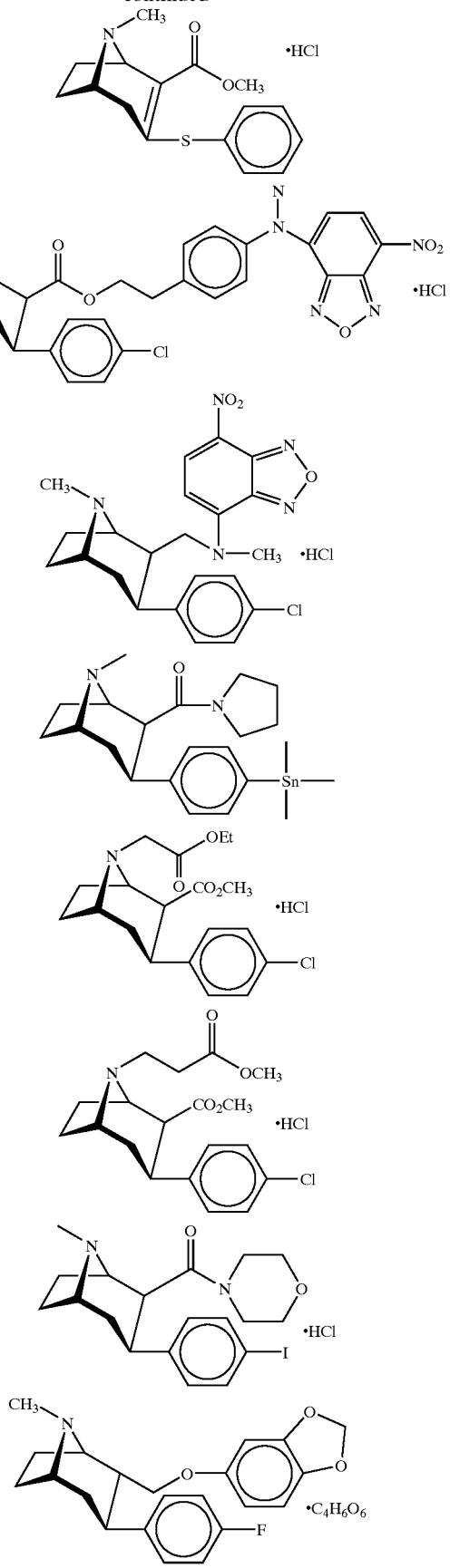

-continued
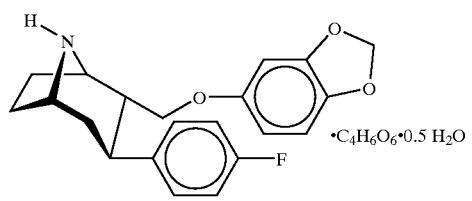
·C₄H₆O₆·0.5 H₂O
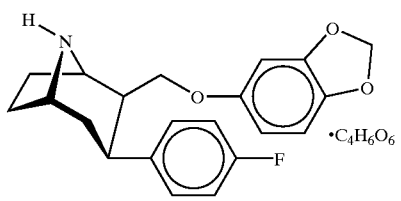
·C₄H₆O₆
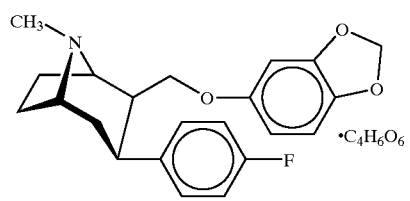
·C₄H₆O₆
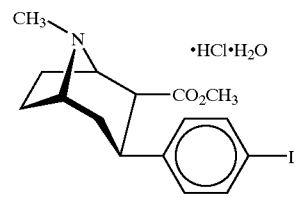
·HCl·H₂O
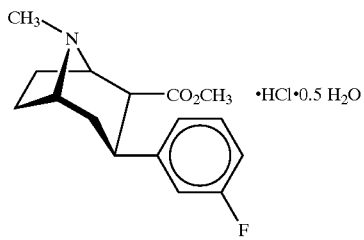
·HCl·0.5 H₂O
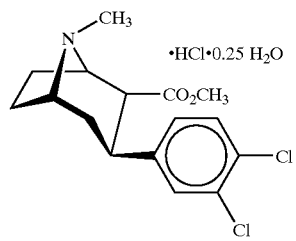
·HCl·0.25 H₂O
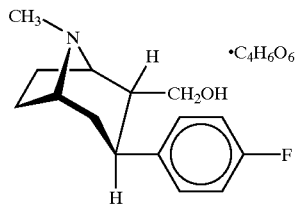
·C₄H₆O₆
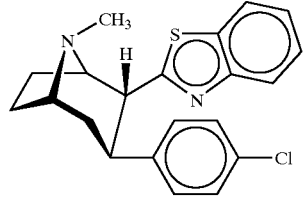
-continued
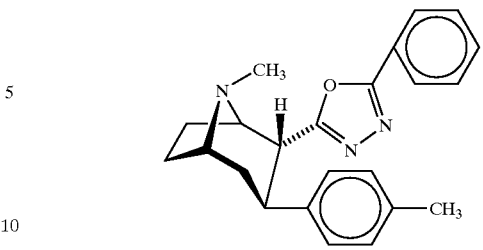
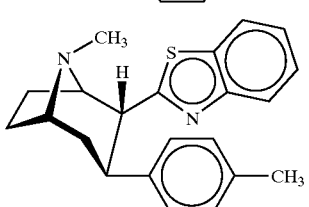
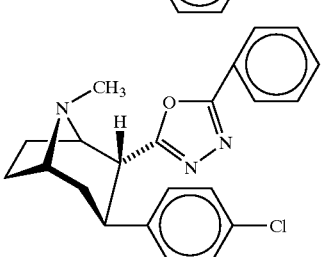
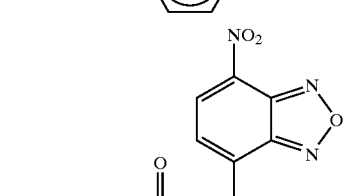
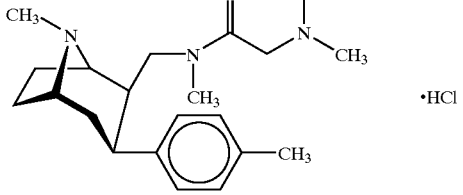
·HCl
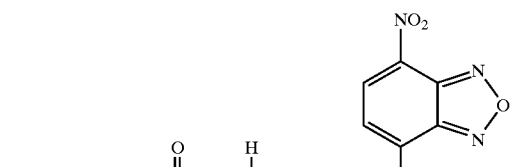
·HCl
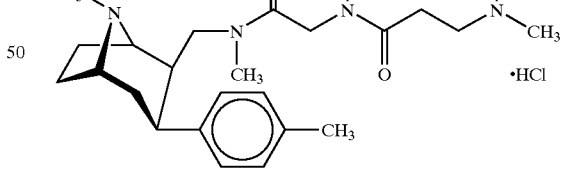
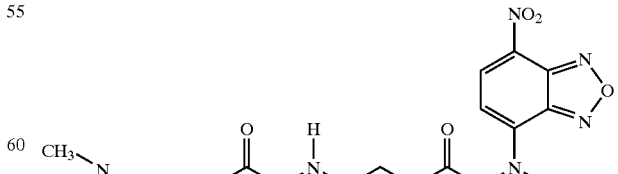
·HCl

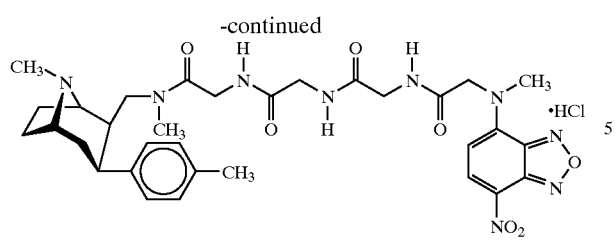
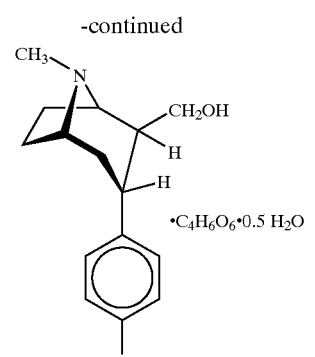
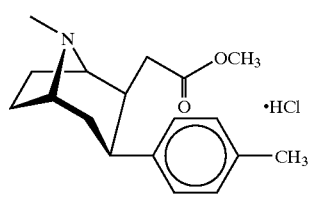
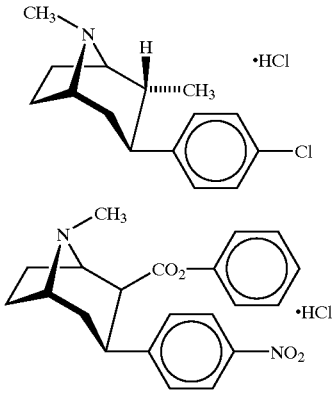
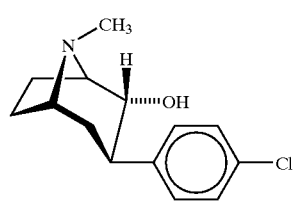
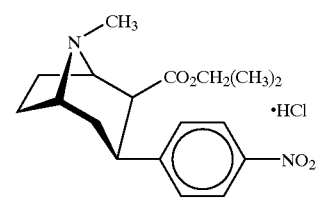
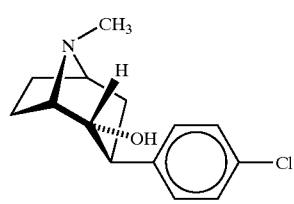
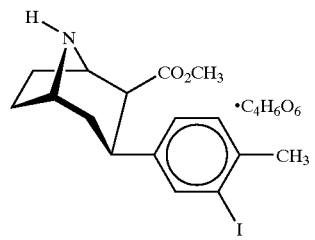
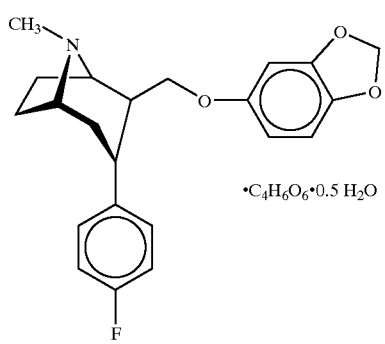
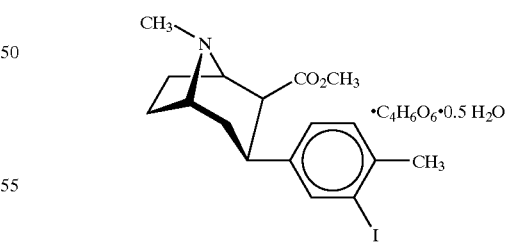
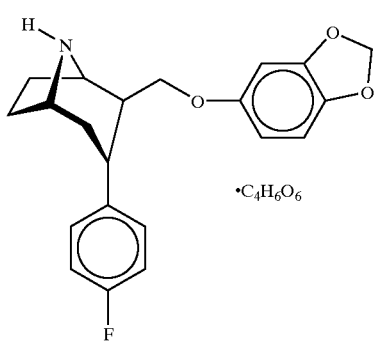
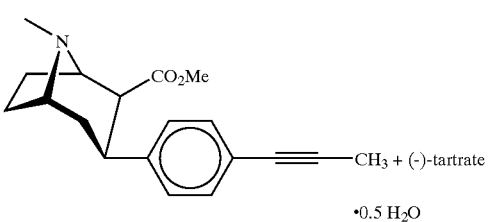

-continued
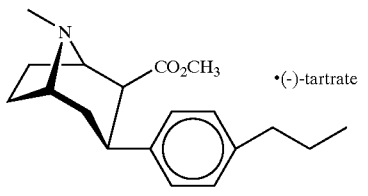 •(−)-tartrate
+ H$_2$O
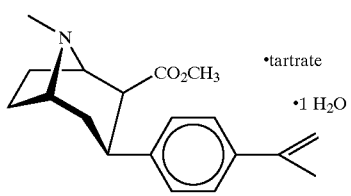 •tartrate
•1 H$_2$O
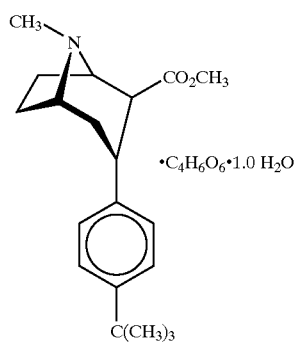 •C$_4$H$_6$O$_6$•1.0 H$_2$O
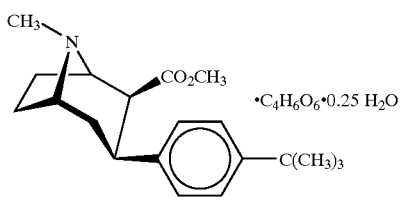 •C$_4$H$_6$O$_6$•0.25 H$_2$O
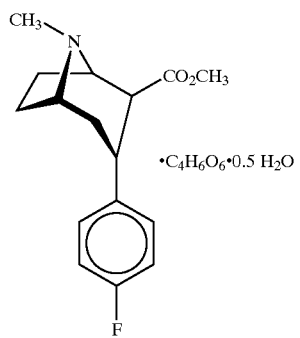 •C$_4$H$_6$O$_6$•0.5 H$_2$O
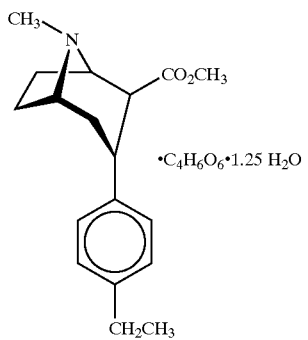 •C$_4$H$_6$O$_6$•1.25 H$_2$O
-continued
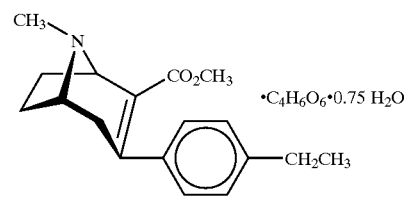 •C$_4$H$_6$O$_6$•0.75 H$_2$O
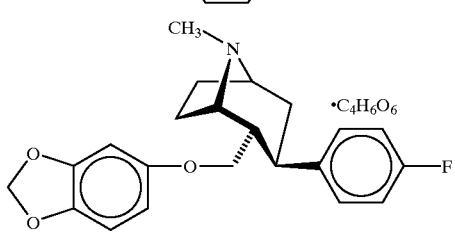 •C$_4$H$_6$O$_6$
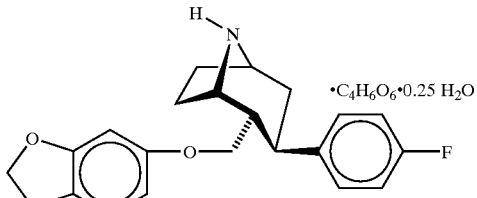 •C$_4$H$_6$O$_6$•0.25 H$_2$O
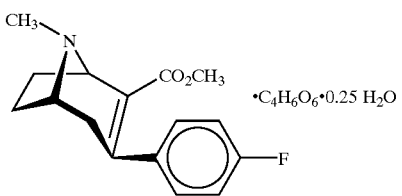 •C$_4$H$_6$O$_6$•0.25 H$_2$O
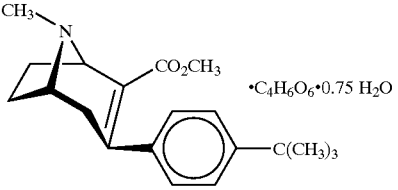 •C$_4$H$_6$O$_6$•0.75 H$_2$O
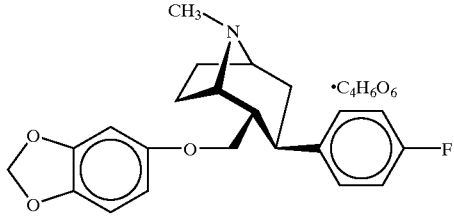 •C$_4$H$_6$O$_6$
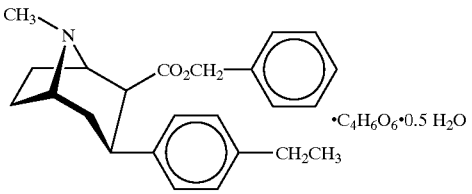 •C$_4$H$_6$O$_6$•0.5 H$_2$O
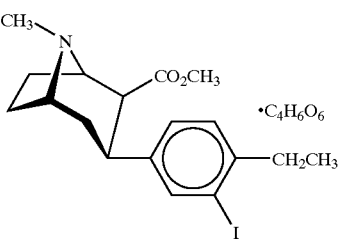 •C$_4$H$_6$O$_6$

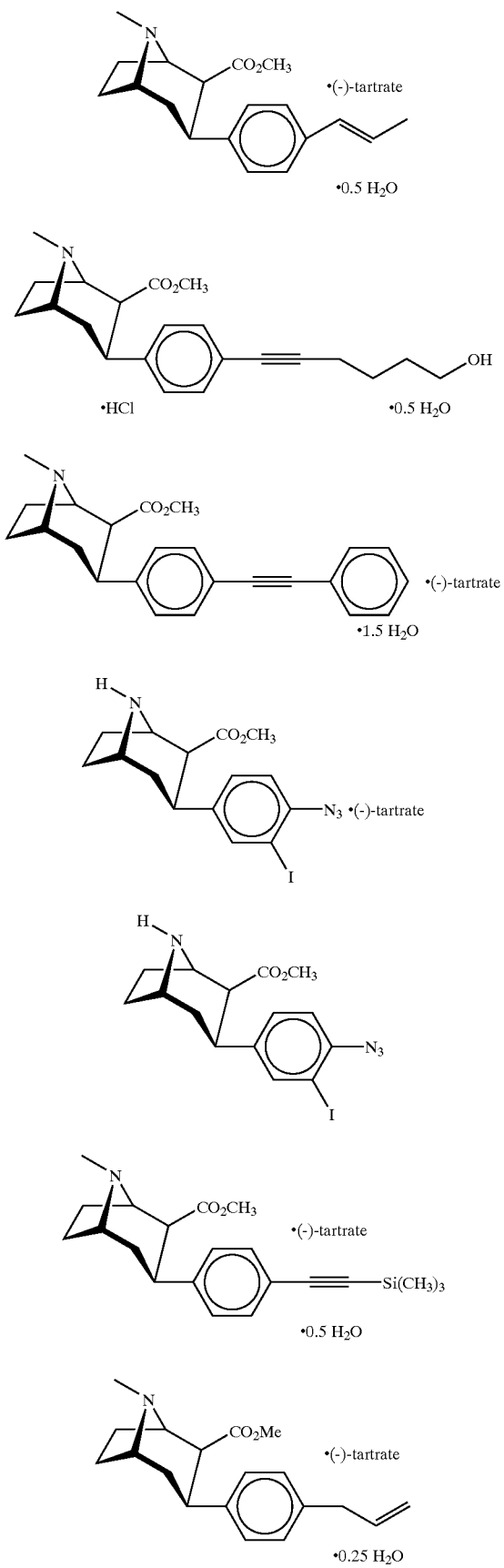
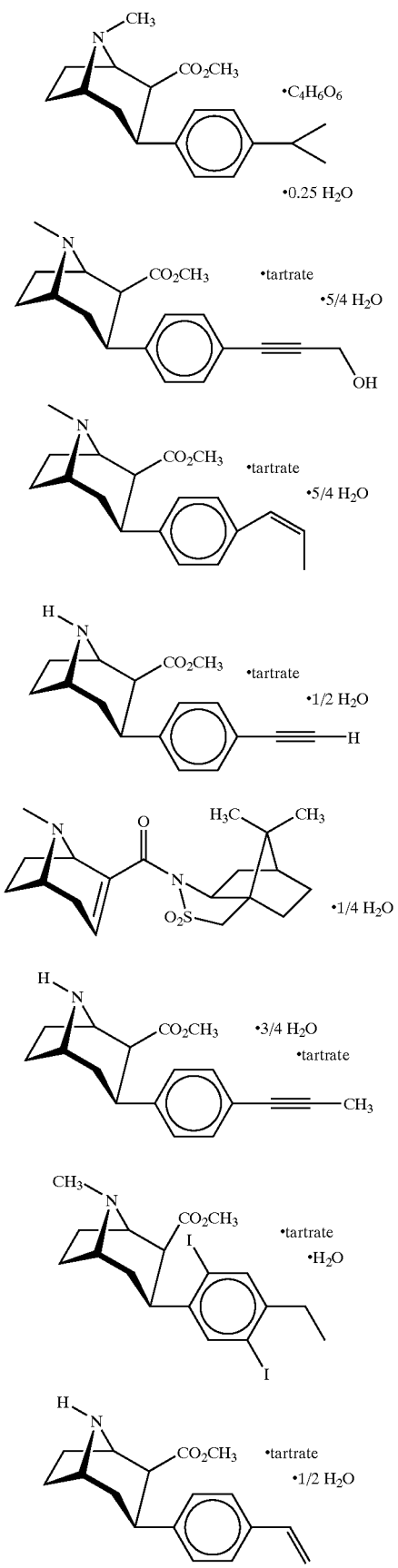

-continued
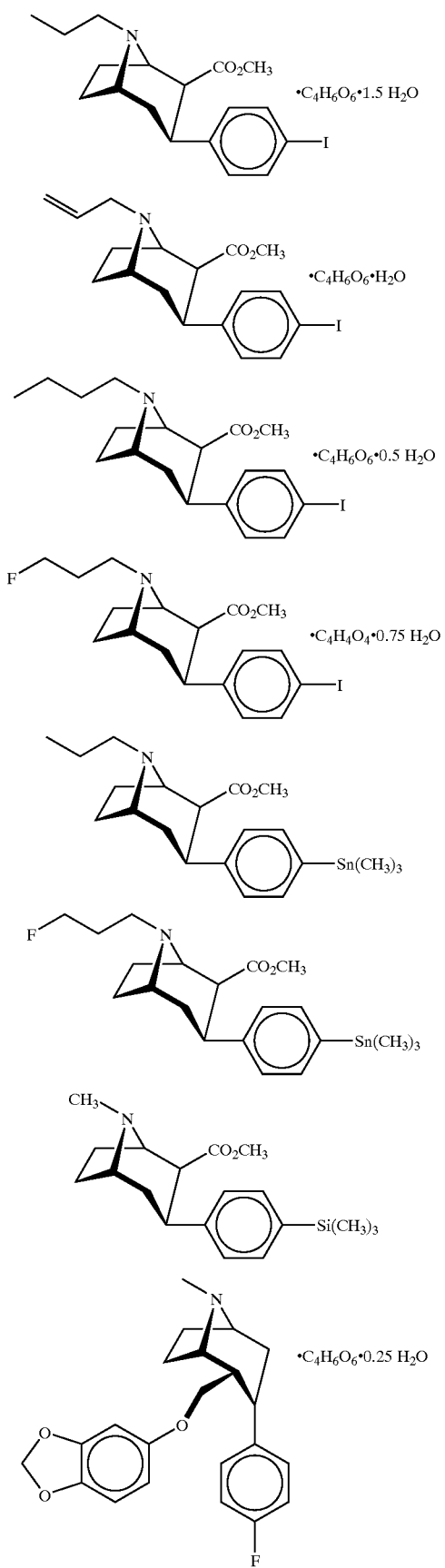
-continued
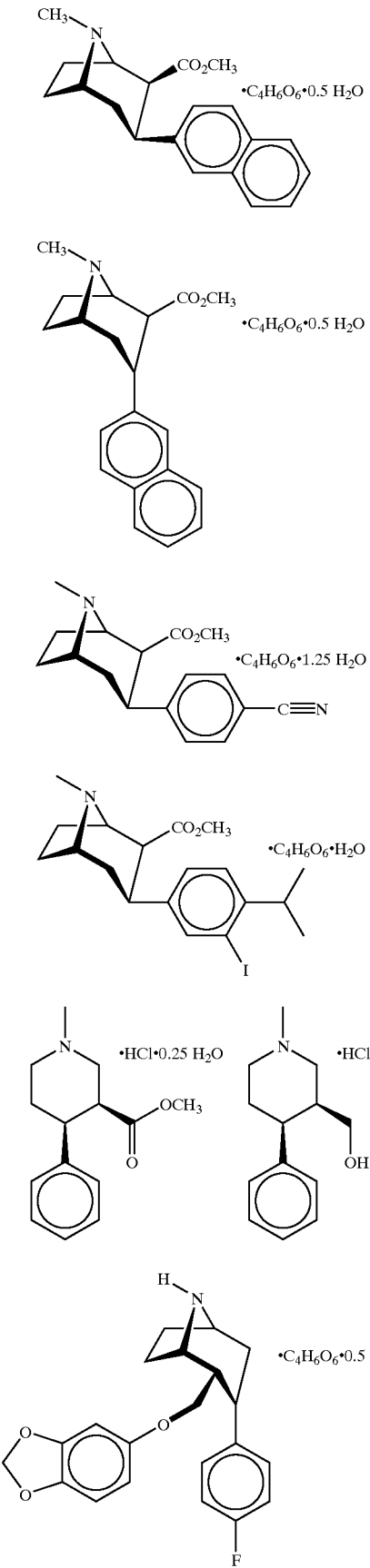

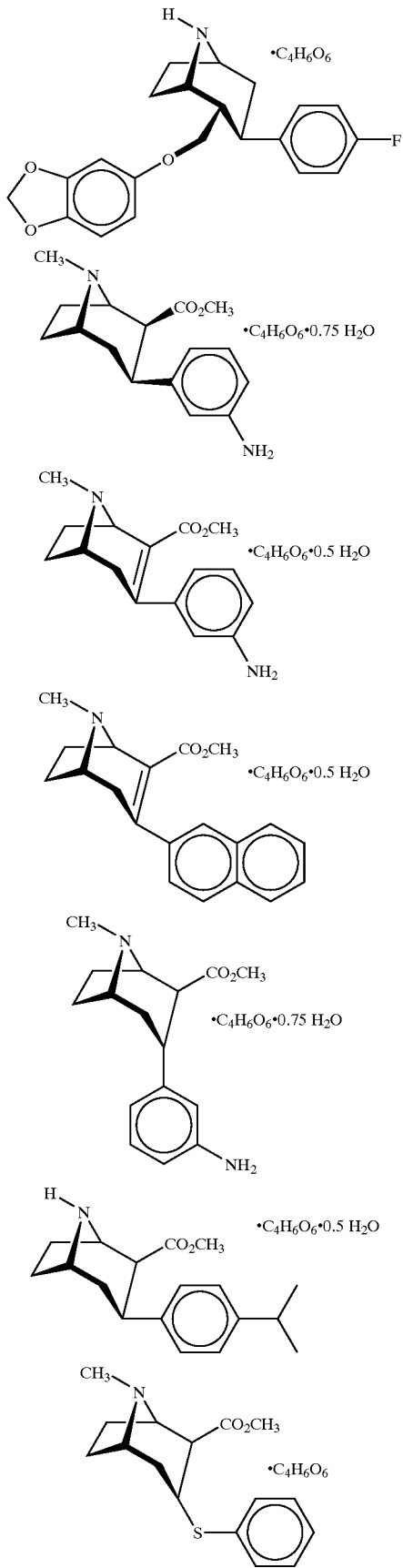
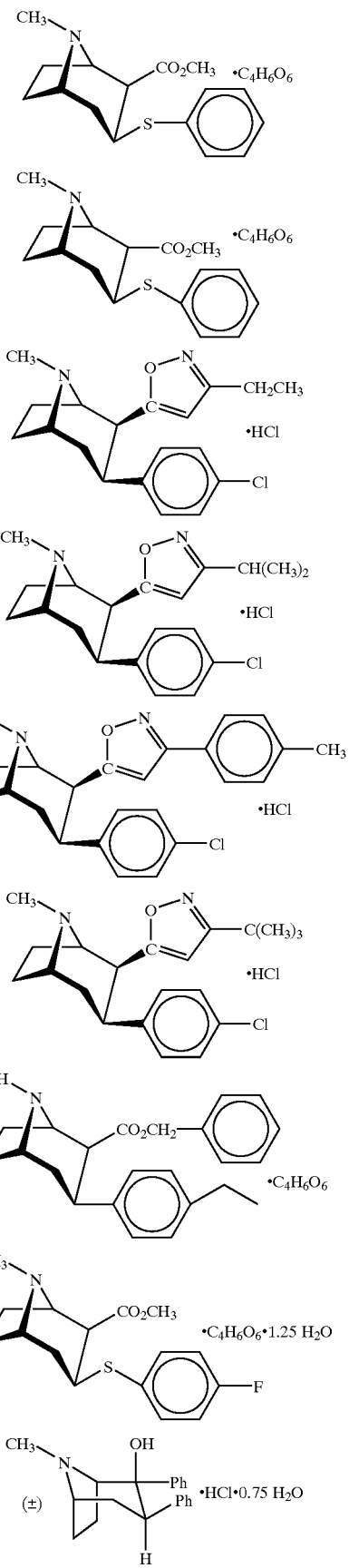

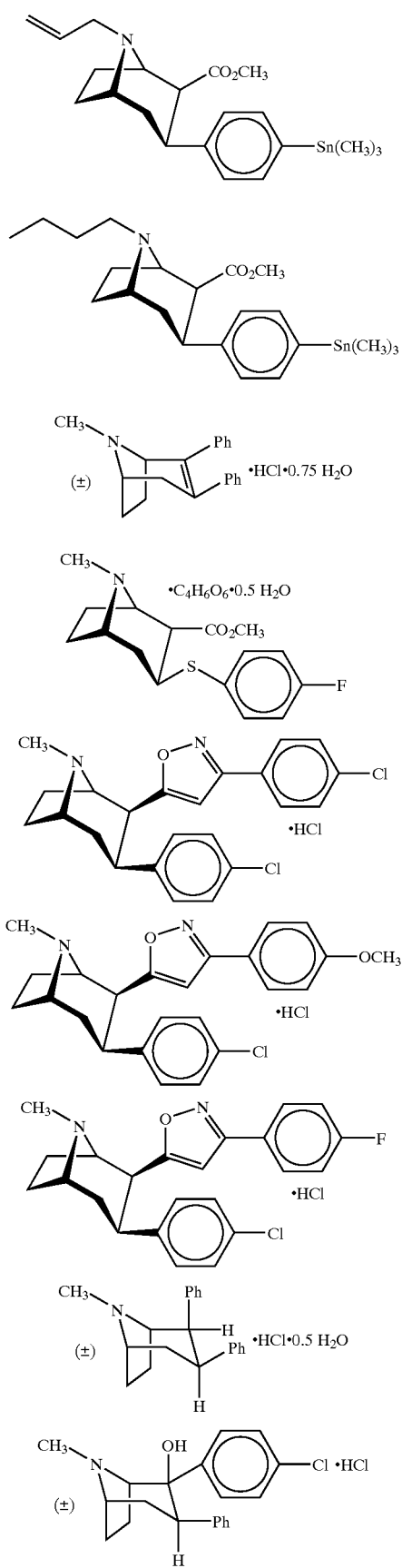
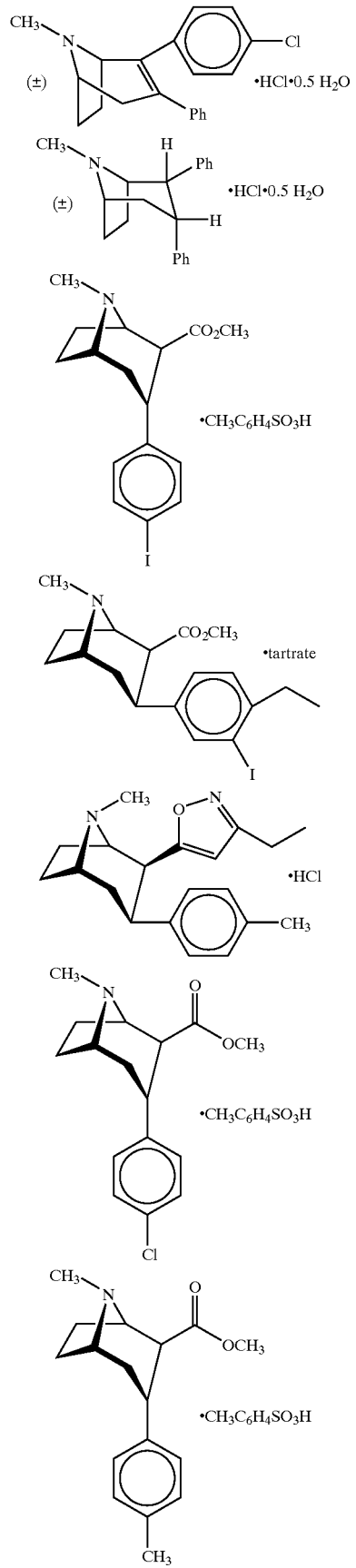

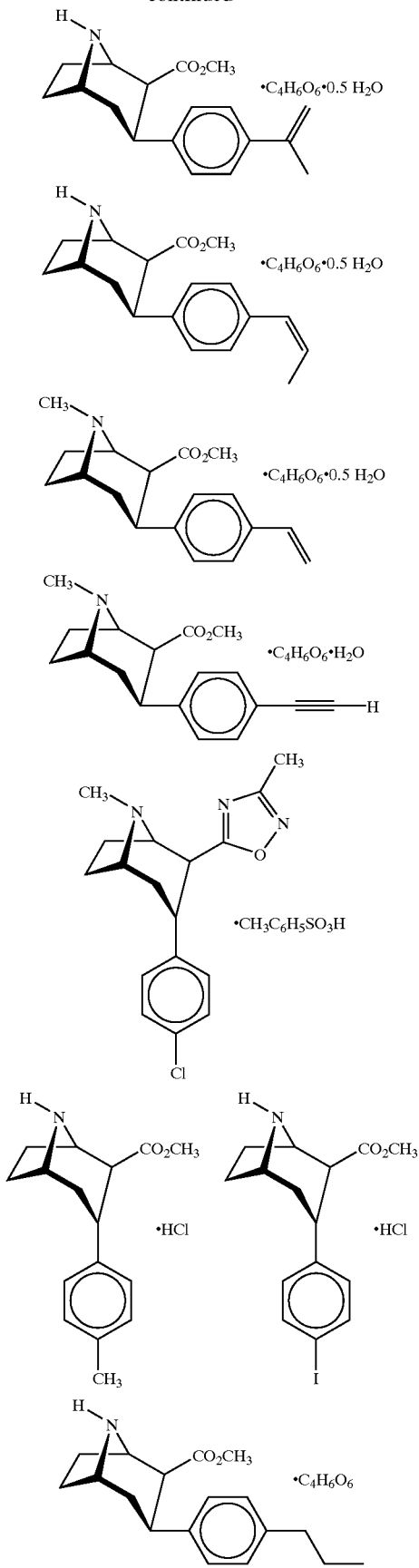
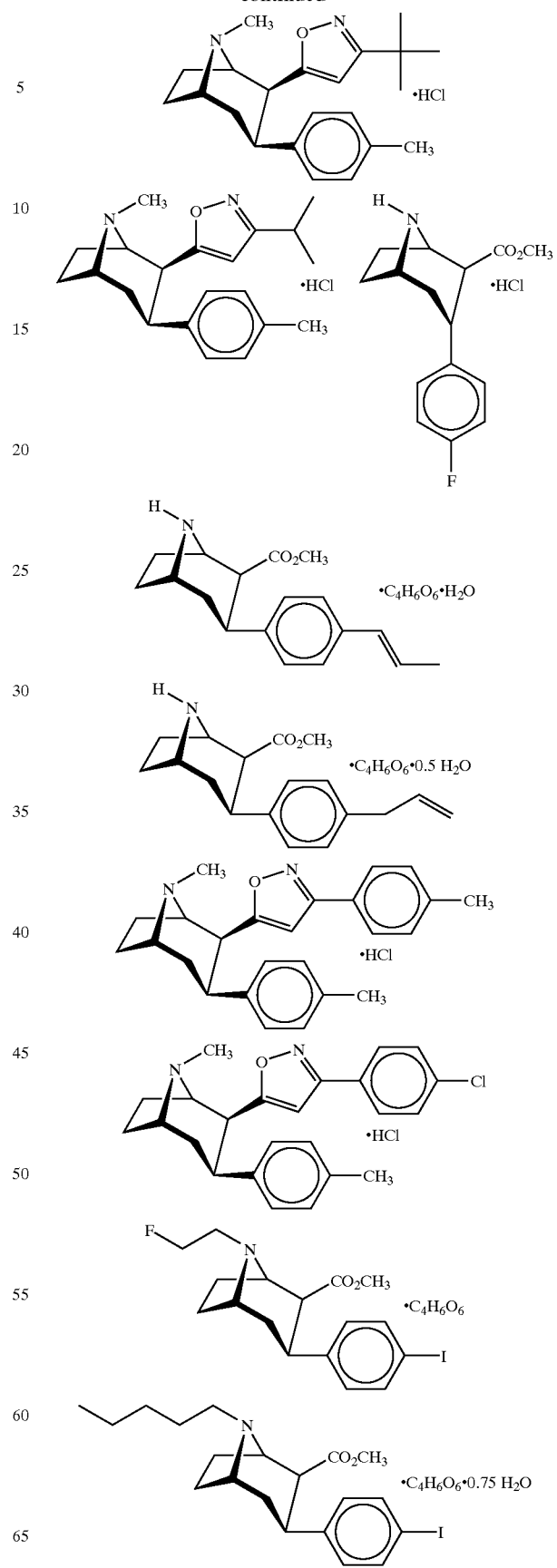

-continued
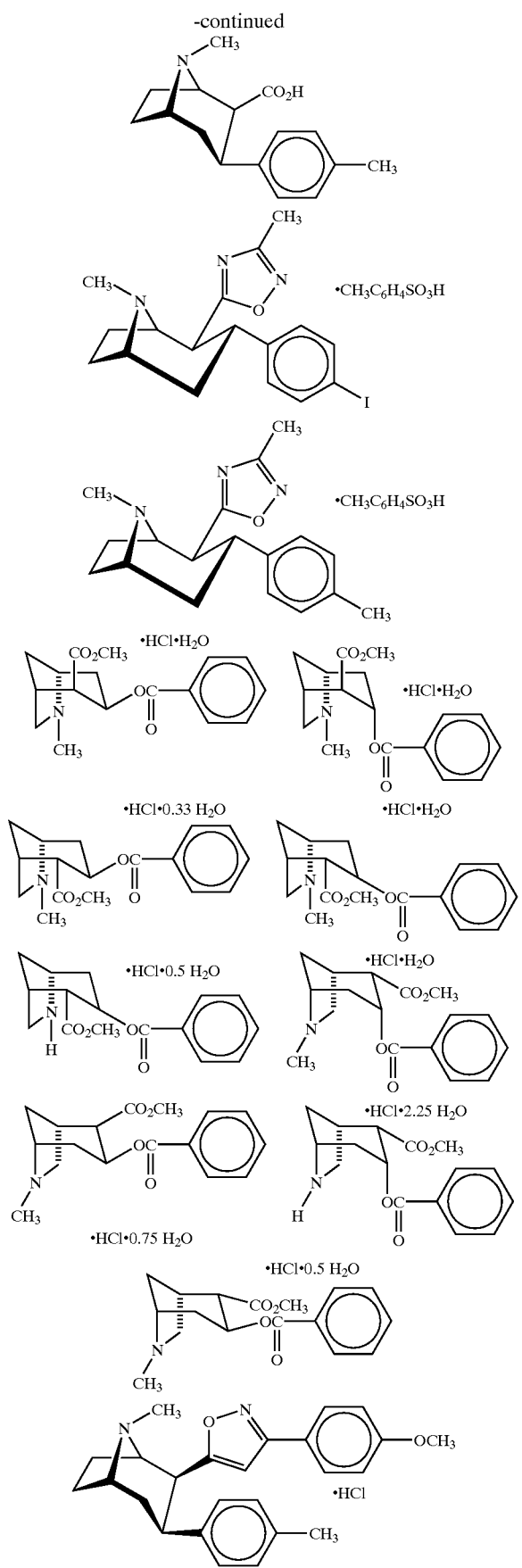
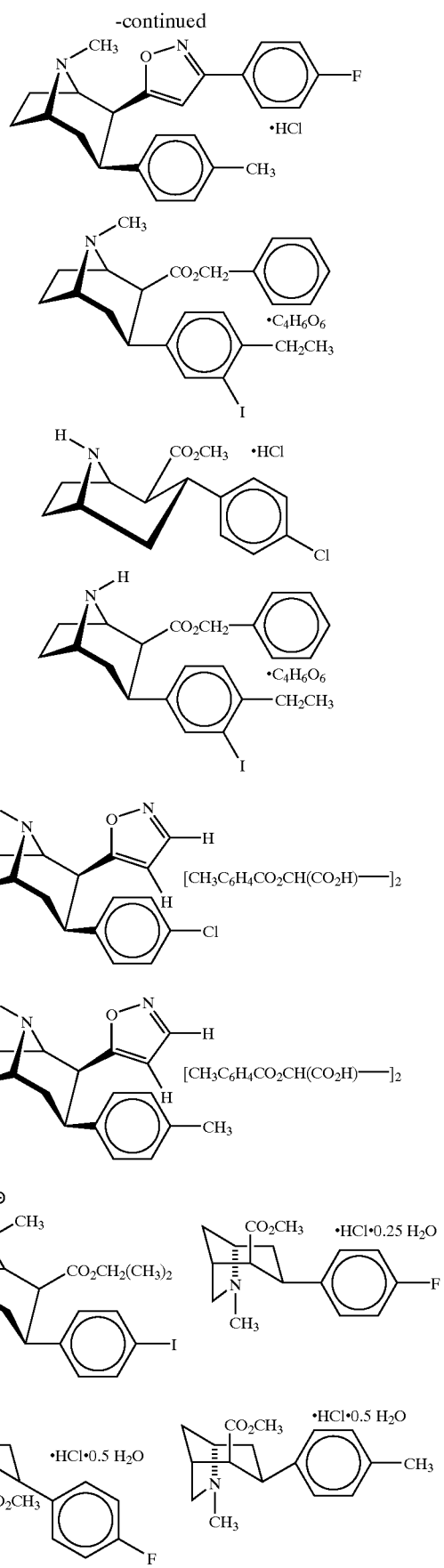

-continued

-continued
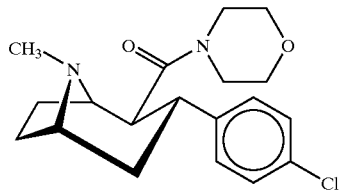
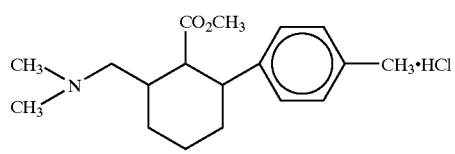
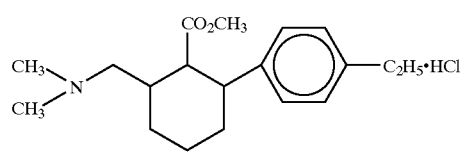
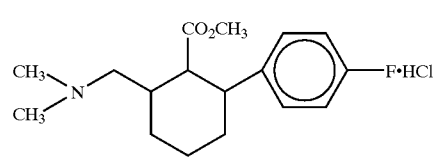
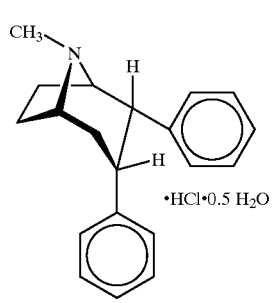
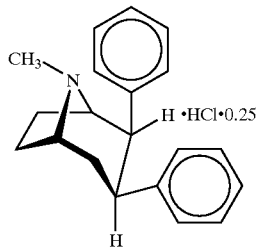
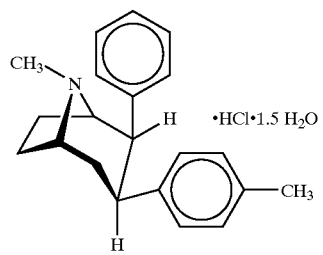
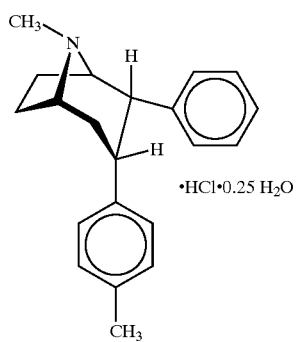
-continued
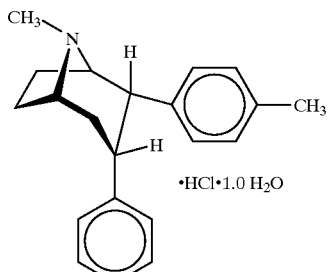
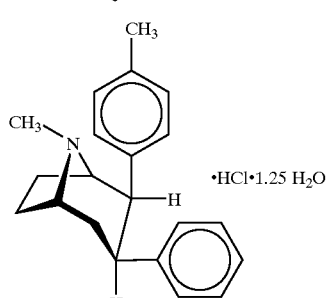
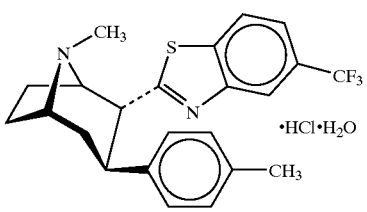
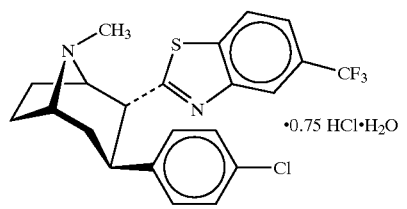
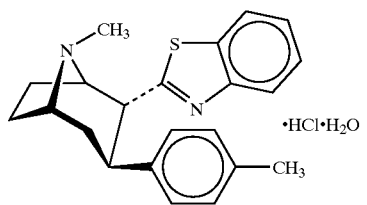
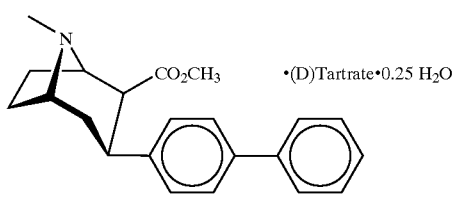
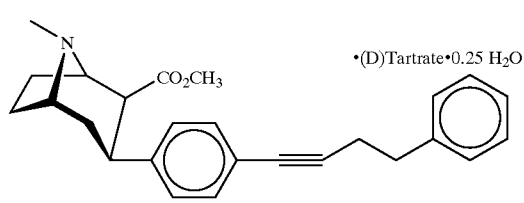

-continued
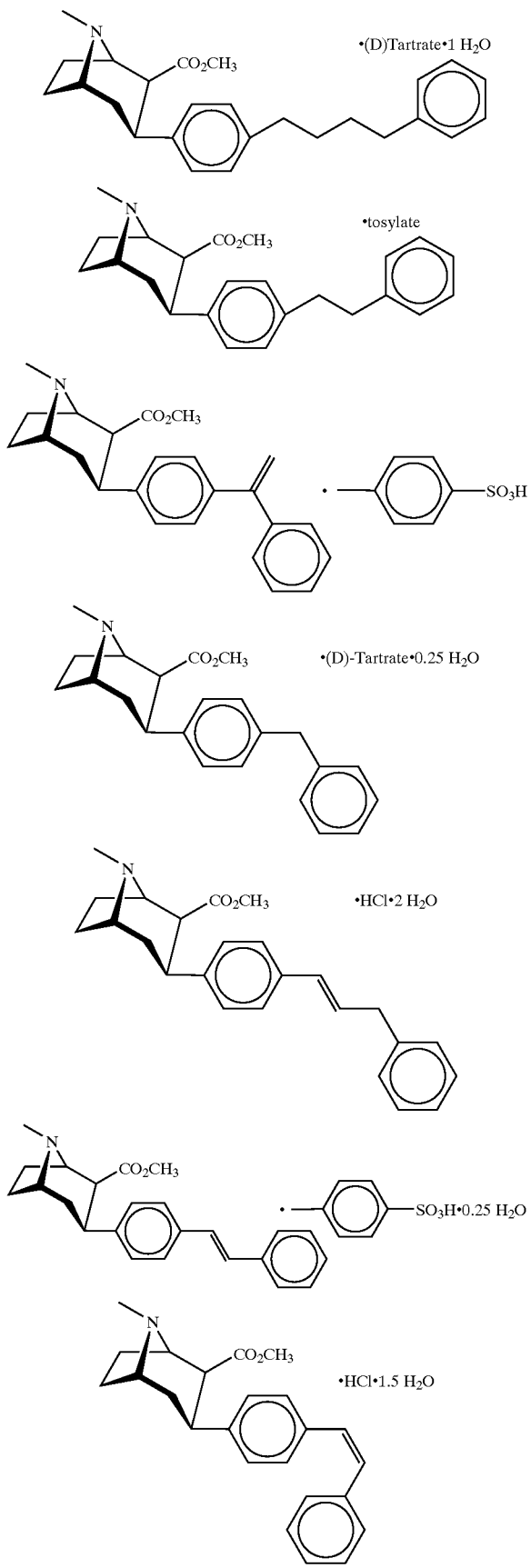
-continued
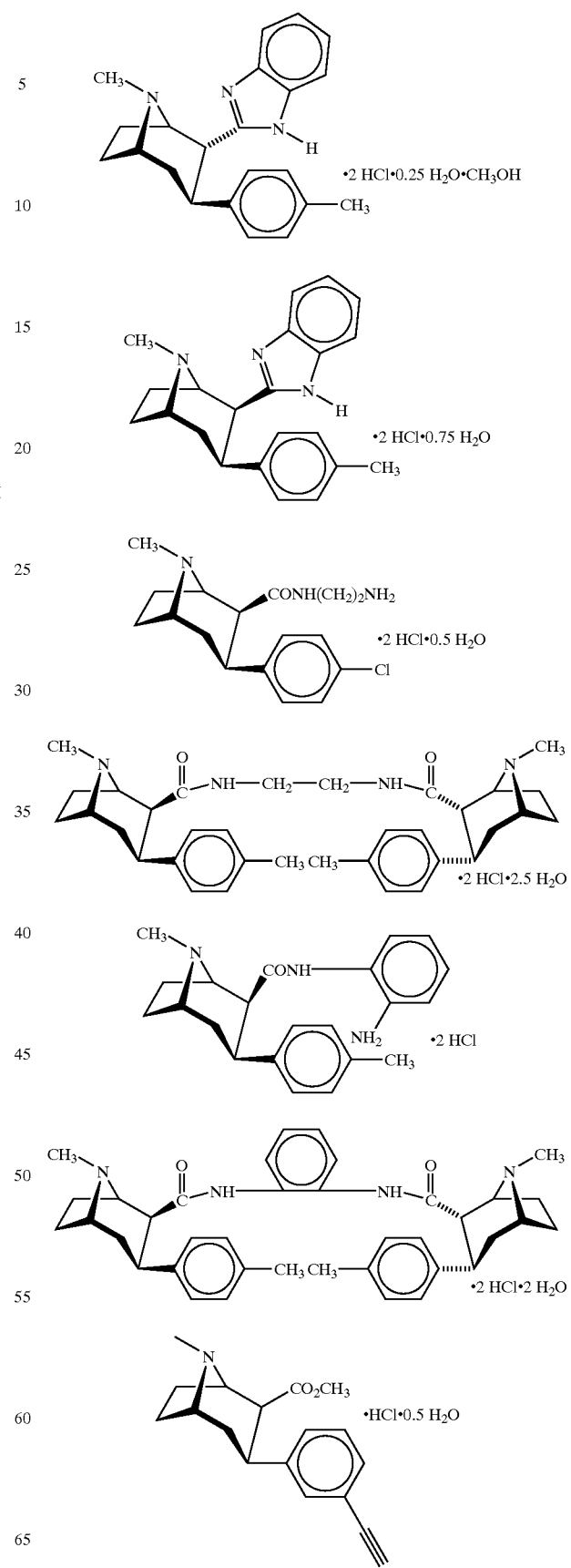

-continued
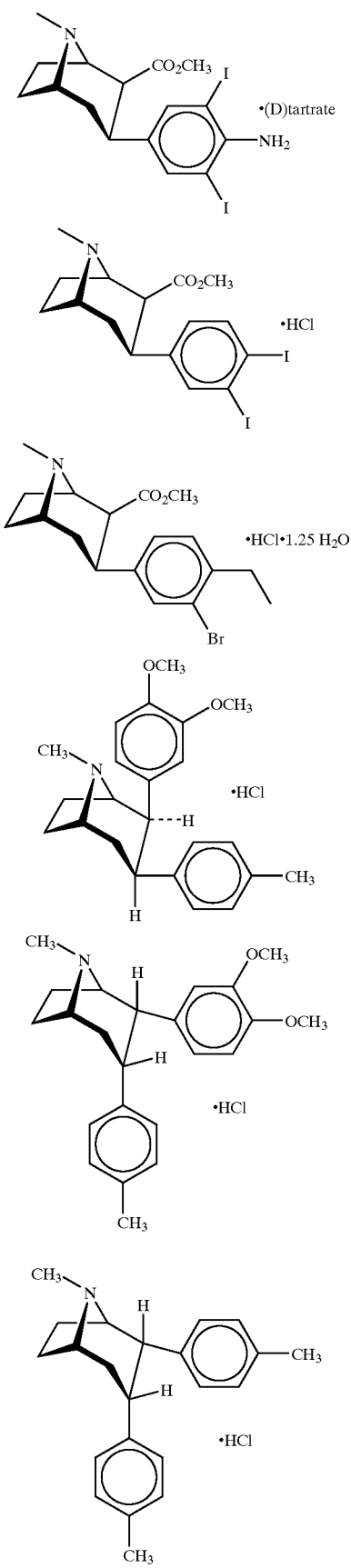
-continued
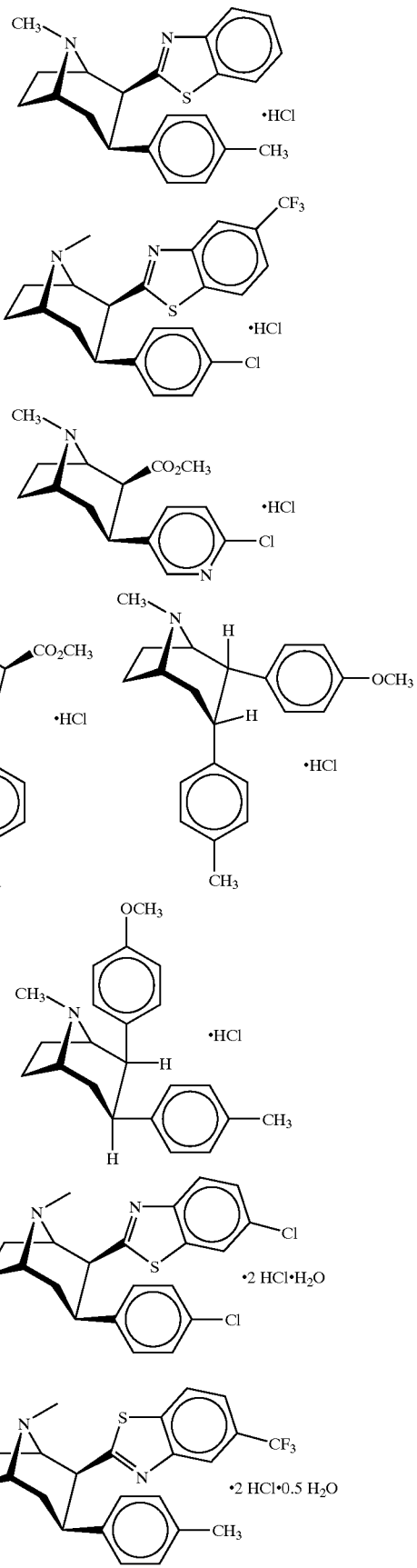

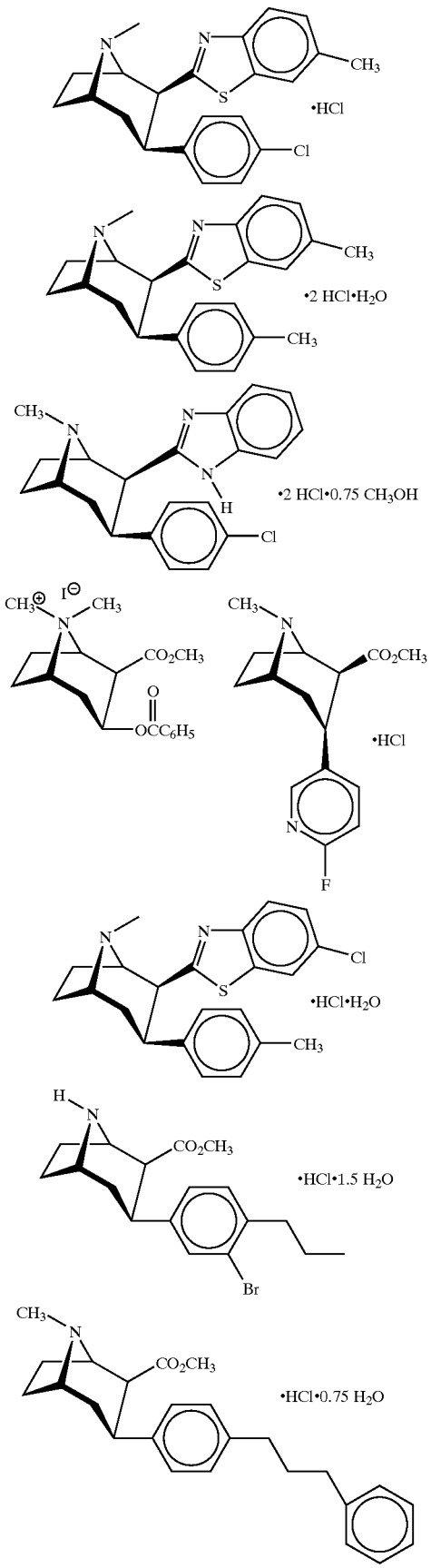
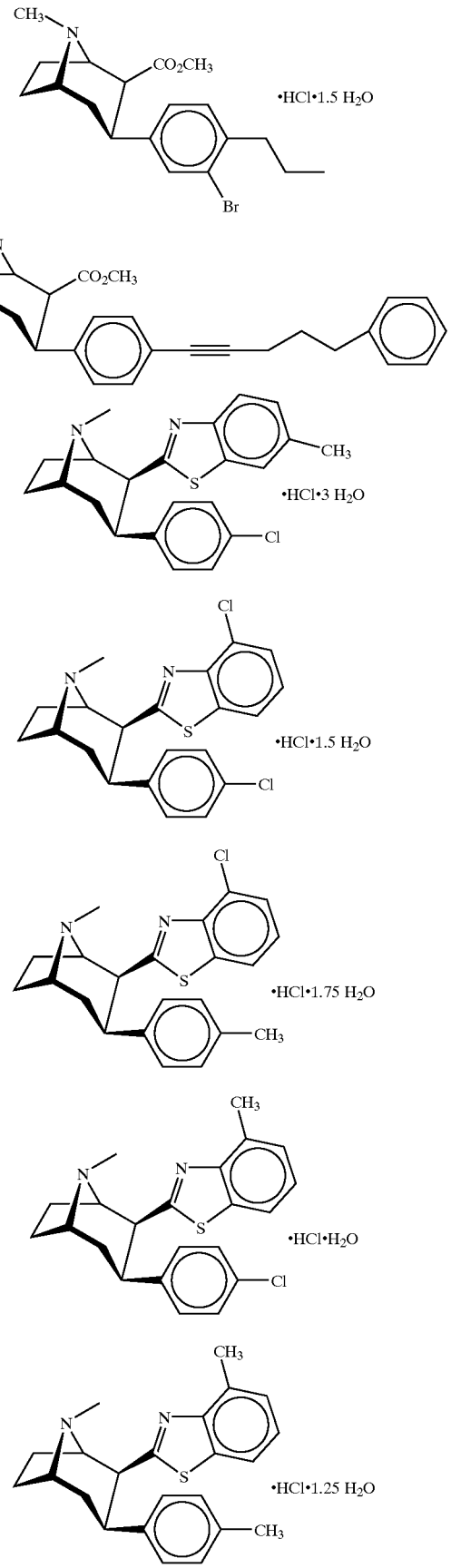

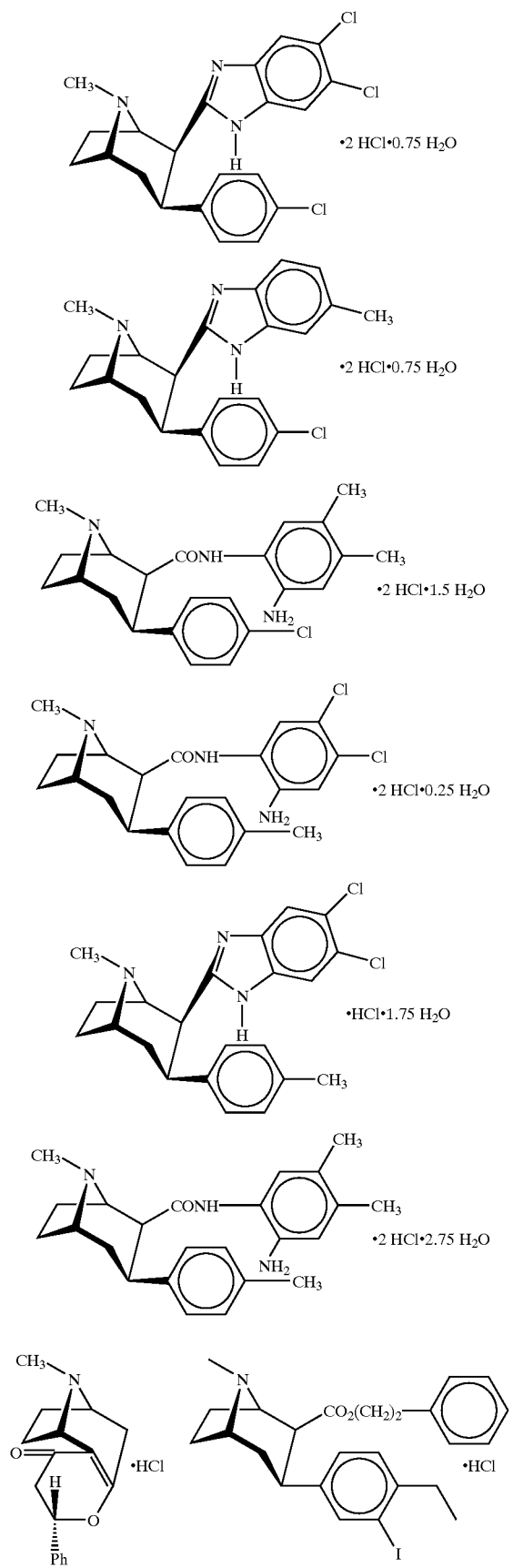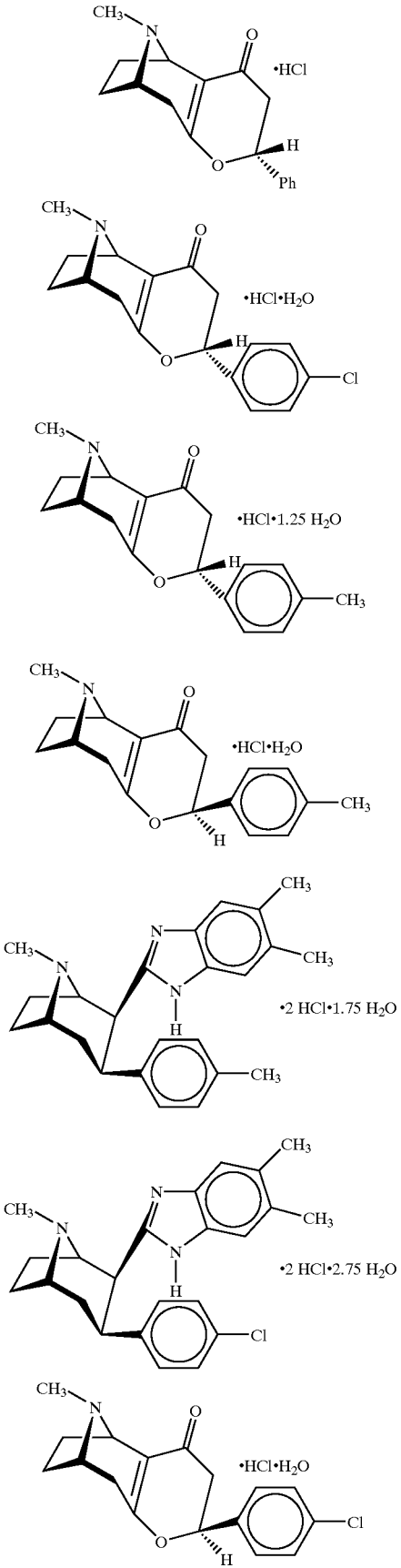

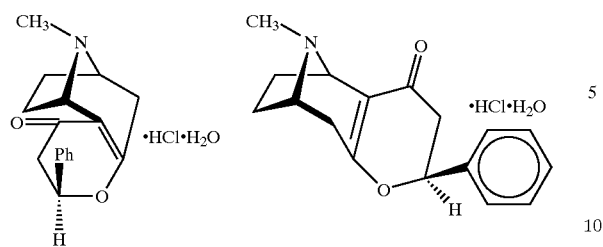
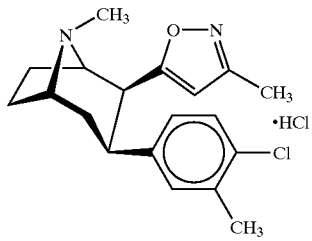
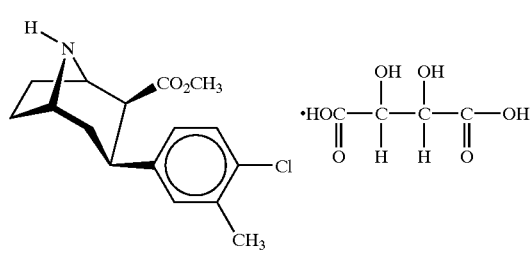
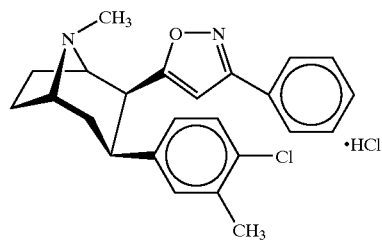
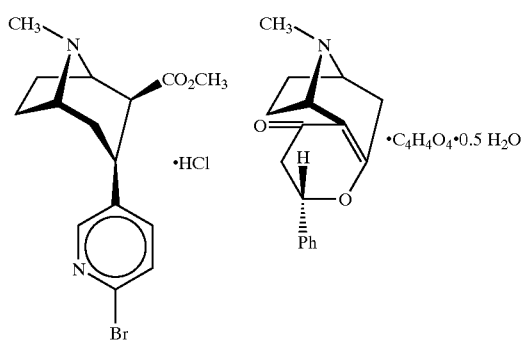
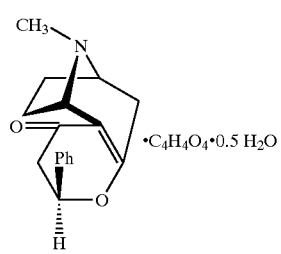
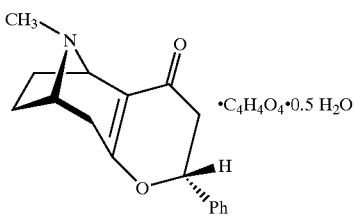
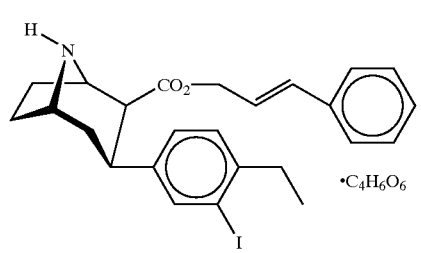

-continued
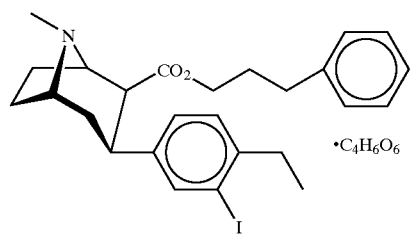
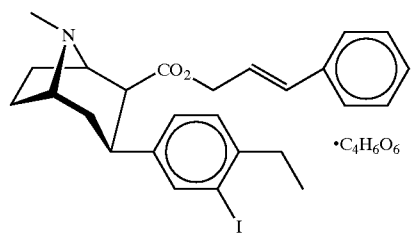
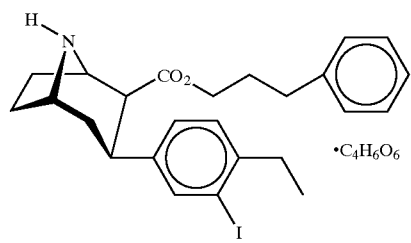
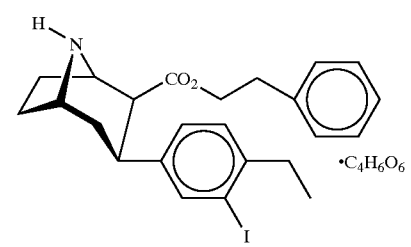
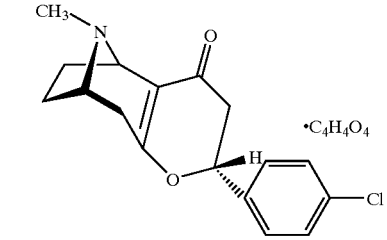
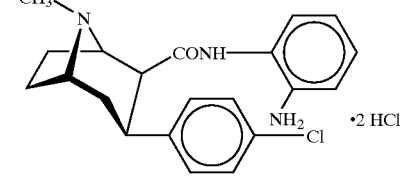
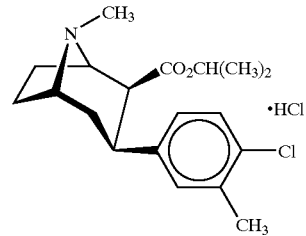
-continued
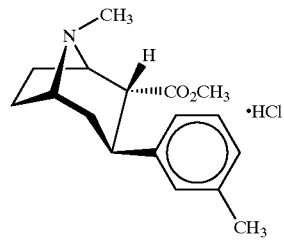
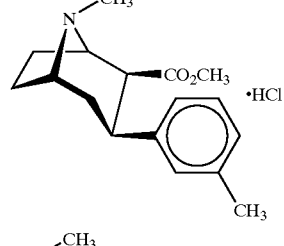
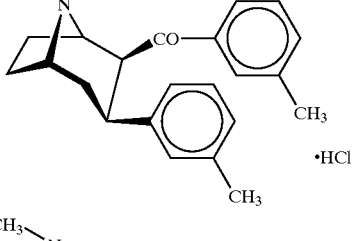
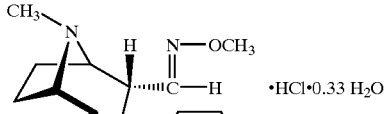
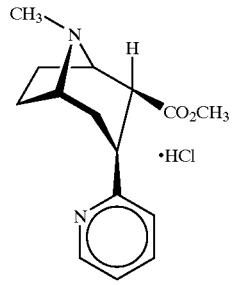
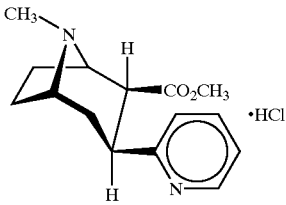
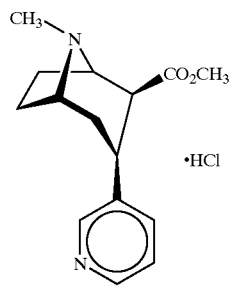
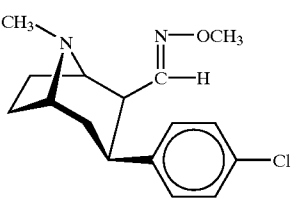

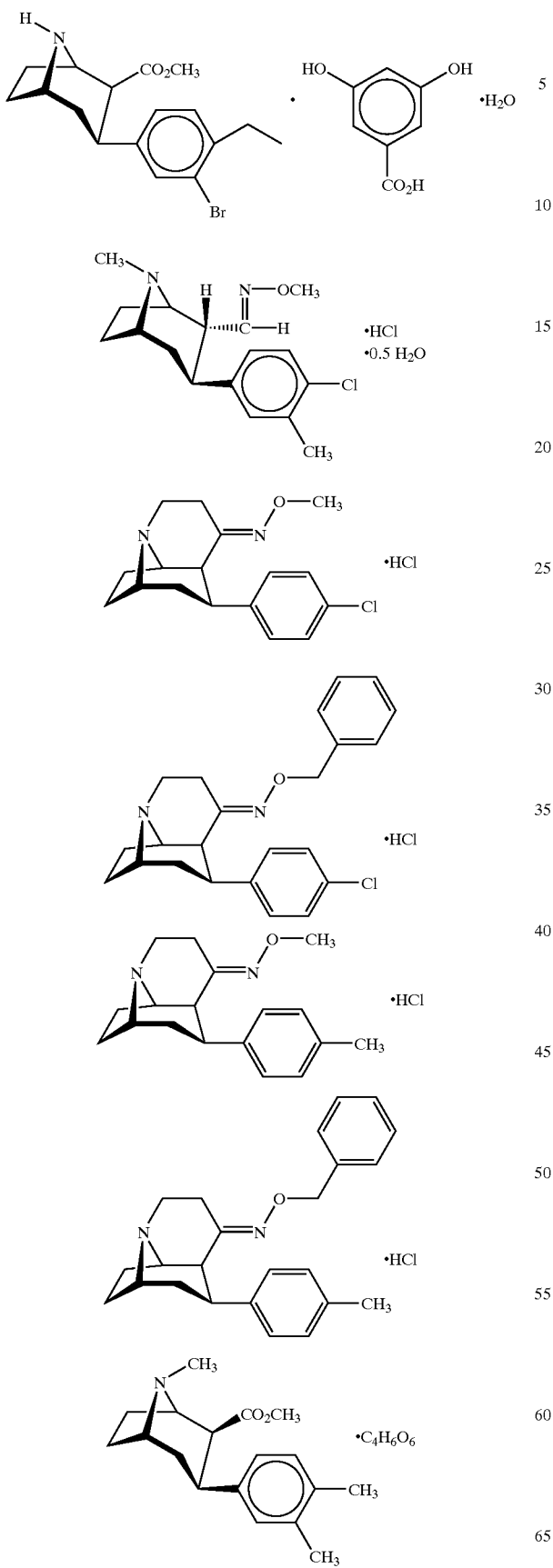
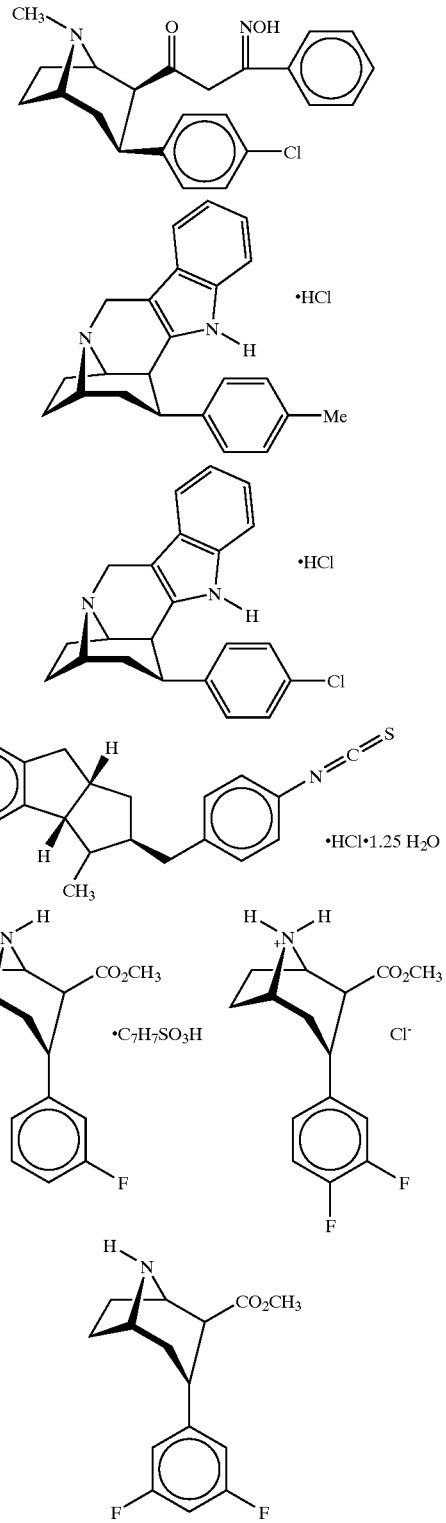
Administration of the Tropane Compounds
A variety of administration techniques may be utilized, among them oral, transdermal or parenteral techniques such as subcutaneous, intravenous, intraperitoneal, intracerebral and intracerebroventricular injections, catheterizations and the like. Such methods of administration are well-known to those skilled in the art. For a general discussion of drug delivery systems, see Kirk-Othmer *Encyclopedia of Chemical Technology*, Fourth Edition, Volume 8, pp. 445–475.

Average quantities of the compounds may vary in accordance with the binding properties of the compound (i.e., affinity, onset and duration of binding) and in particular should be based upon the recommendations and prescription of a qualified physician.

The therapeutic compositions useful in practicing the therapeutic methods of this invention may include, in admixture, a pharmaceutically acceptable excipient (carrier) and one or more of the compounds of the invention, as described herein as an active ingredient.

The preparation of therapeutic compositions which contain such neuroactive compounds as active ingredients is well understood in the art. Such compositions may be prepared for oral administration, or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, and pH buffering agents which enhance the effectiveness of the active ingredient. The compounds of the invention can be formulated into the therapeutic composition as neutralized pharmaceutically acceptable salt forms.

The therapeutic compositions are conventionally administered orally, by unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, the presence of other agonists and antagonists in the subject's system, and degree of binding or inhibition of binding desired. Precise amounts of active ingredient required to be administered depend on the judgment of the practitioner and are peculiar to each individual. However, suitable dosages may range from about 0.01 to about 1,000, preferably about 0.25 to about 500, and more preferably 10 to 50 milligrams of active ingredient per kilogram body weight of individual per day and depend on the route of administration. For oral administration, 1 to 100 milligrams of active ingredient per kilogram body weight of individual per day is a preferred dose. However, the exact dosage must be determined by factoring in rate of degradation in the stomach, absorption from the stomach, other medications administered, etc. Suitable regimes for administration are also variable, but are typified by an initial administration followed by repeated doses at one or more hour intervals by a subsequent injection or other administration. Alternatively, continuous intravenous infusion sufficient to maintain appropriate concentrations in the blood are contemplated.

The present invention is directed to a method of treating smoking addiction. This may be accomplished by administering to a patient in need of terminating a smoking addiction a phenyltropane compound. While not wishing to bound by any particular theory, it is believed that by smoking addiction may be successfully treated by blocking some of the pharmacological effects of nicotine, such as, but not limited to reinforcement, antinociception, hypothermia, drug discrimination and motor impairment, while also dissociating some of the reinforcing affects of smoking. Within the context of the present invention, a patient in need of terminating a smoking addiction is a person who smokes on a regular basis and is either unable or unwilling to terminate smoking on a regular basis. The method of treating a smoking addiction may be practiced, by administering a phenyltropane compound as described, preferably concurrent with or in advance of the act of smoking. In this fashion, the patient addicted to smoking will also be subject to the effects of the phenyltropane compounds while smoking, which can act to dissociate the reinforcing effects of smoking, from the act of smoking itself. The amount of phenyltropane compound administered to be effective to dissociate the reinforcing effects of smoking from the act of smoking may vary depending on the patient and the nature of the patients addiction to smoking, however, determination of effective dosages and treatment schedules is within the level of skill of those of ordinary skill in the art, without undue experimentation.

The present invention is also directed to a method of preventing an addiction to smoking, by administering a phenyltropane compound. A person (patient) in need of preventing an addiction to smoking may be a non-smoker or an occasional smoker, who is concerned about developing an addiction to smoking. The method of preventing a smoking addiction may be practiced, by administering phenyltropane compounds as described, preferably in advance of the act of smoking. In this fashion, subject to the effects of the phenyltropane compounds, the patient will not develop a strong association of the act of smoking with the reinforcing effects of smoking. The amount of phenyltropane compound administered to be effective to prevent the association of the reinforcing effects of smoking from the act of smoking may vary depending on the patient and the nature of the patient. However, determination of effective dosages and treatment schedules is within the level of skill of those of ordinary skill in the art, without undue experimentation.

The present invention is also directed to a method of treating nicotine addiction. This may be accomplished administering to a patient in need thereof, a phenyltropane compound. Within the context of the present invention, a patient in need of terminating a nicotine addiction is a person who consumes nicotine on a regular basis and is either unable or unwilling to terminate nicotine consumption on a regular basis. The method of treating a nicotine addiction may be practiced, by administering phenyltropane compounds as described, preferably concurrent with or in advance of the act of nicotine consumption. In this fashion, the patient addicted to nicotine will also be subject to the effects of the phenyltropane compounds, which can act to dissociate the physiological effects of nicotine consumption from the act of consuming nicotine. The amount of phenyltropane compound administered to be effective to dissociate the physiological effects of nicotine from the act of nicotine consumption may vary depending on the patient and the nature of the patients addiction to nicotine. However, determination of effective dosages and treatment schedules is within the level of skill of those of ordinary skill in the art, without undue experimentation.

The method of the present invention may be practiced with compounds which exhibit a noncompetative nicotinic antagonist activity. Damaj et al. *The Journal of Pharmacology and Experimental Therapeutics vol.* 289, no.3 (1999) 1229–1236, provides a pharmacological characterization of nicotine's interaction with cocaine and cocaine analogs, the entire contents of which are hereby incorporated by reference. The effectiveness of the present method is appreciated in the ability to block some but not all of the pharmacological effects of nicotine. In a preferred embodiment the present method blocks the pharmacological effects of antinociception, seizures, and motor impairment, while not effecting body temperature or drug discrimination.

According to another embodiment of the present invention, it is possible to prevent the development of an addiction to smoking, by administering to a human in need of preventing an addiction to smoking, a phenyltropane compound. In this embodiment, the compound can be administered prophylactically in order to prevent a subject from becoming addicted to smoking in the first place. Alternatively, the compound can be administered to a subject who is in the process of smoking cessation in order to prevent a relapse.

EXAMPLES

Having generally described this invention, a further understanding can be obtained by reference to certain specific examples which are provided herein for purposes of illustration only and are not intended to be limiting unless otherwise specified.

Materials and Methods

Animals

Male ICR mice (20–25 g) and male Sprague-Dawley rats (175–225 g) obtained from Harlan Laboratories (Indianapolis, IN) were used throughout the study. The mice were housed in groups of six and had free access to food and water. The rats were housed individually and had restricted access to food as described later.

Drugs (−)-Nicotine was obtained from Aldrich Chemical Company, Inc. (Milwaukee, Wis.) and converted to the ditartrate salt as described by Aceto et al. (1979). Dihydro-β-erythroidine, fluoxetine, nomifensine, GBR 12909, lidocaine, amphetamine, caffeine, and nisoxetine were purchased from Research Biochemicals Inc. (Natick, Mass). Mocamylamine hydrochloride was a gift from Merck, Sharp and Dohme & Co. (West Point, Pa.). Procaine was purchased from Sigma Chemical Co. (St. Louis, Mo.). Cocaine HCl, cocaine methiodide methamphetamine, and methylphenidate were supplied by the National Institute on Drug Abuse (Washington, DC). The cocaine analogs used in the present study were various carboxylic acid esters of substituted phenyltropanes (Carroll et al., 1991, 1992; Lewin et al., 1992). All drugs were dissolved in physiological saline (0.9% sodium chloride) and given in a total volume of 0.2 ml/100 g b.wt. in rats and 1 ml/100 g b.wt. in mice for a.c. and i.p. injections. Cocaine HCl and cocaine methiodide were administered i.p. to animals. All doses are expressed as the free base of the drug.

Behavioral and Pharmacological Assays in Mice

Locomotor Activity. Mice were placed into individual Omnitech photocell activity cages (28×16.5 cm) 10 min after i.p. administration of either 0.9% saline or cocaine. Interruptions of the photocell beams (two banks of eight cells each) were then recorded for the next 30 min. Data were expressed as number of photocell interruptions. For antagonism studies, the mice were pretreated s.c. with either saline, dihydro-β-erythroidine, or mecamylamine 10 min before cocaine.

Anitinociception. The tail-flick method of D'Amour and Smith (1941) as modified by Dewey et al. (1970) was used. A control response (2–4 s) was determined for each animal before treatment, and a test latency was determined after drug administration. To minimize tissue damage, a maximum latency of 10 s was imposed. Antinociceptive response was calculated as percent maximum possible effect (% MPE), where % MPE=[((test-control)/(10-control))×100], Groups of 8 to 12 animals were used for each dose and for each treatment. Mice were tested 5 min after nicotine administration for the dose-response evaluation. Antagonism studies were carried out by pretreating the mice s.c. with either saline or various drugs at different times before nicotine. The animals were tested 5 min after administration of nicotine.

Body Temperature. Rectal temperature was measured by a thermistor probe (inserted 24 mm) and digital thermometer (Yellow Springs Instrument Co., Yellow Springs, Ohio). Readings were taken just before and at 30 min after the s.c. injection of nicotine. For antagonism studies, mice were pretreated with either saline or various drugs 10 min before nicotine. The difference in rectal temperature before and after treatment was calculated for each mouse. The ambient temperature of the laboratory varied from 21 to 24° C. from day to day.

Motor Coordination. To measure motor coordination, a wooden rod 6 cm in diameter was partitioned into three compartments by circular metal discs (28 cm in diameter) at 18-cm intervals. The rod was attached to a motor and rotated at a rate of 4 rpm. Naive mice were trained until they could remain on the rotarod for 3 min. Animals that failed to meet this criterion within 5 trials were discarded. This training took place no longer than 15 min before the s.c. administration of nicotine. Twenty minutes after the injection, mice were placed on the rotarod for 5 min. The amount of time the animals remained on the rotarod was recorded and percent impairment was calculated as % Impairment=[(]-(test time in s/300))×100]. An impairment value of 0% corresponds to the subjects that remained on the rotarod for 5 min (300 s), whereas 100% impairment corresponds to subjects, that fell off the rotarod immediately.

Seizure Activity. Following s.c. injection of nicotine at a dose of 9 mg/kg, each animal was placed in a 30 cm×30 cm Plexiglass cage and observed for 5 min. Whether a clonic seizure occurred within a 5-min time period was noted for each animal after s.c. administration of different drugs. This amount of time was chosen because seizures occur very quickly after nicotine administration. Results are expressed as percentage seizure. Antagonism studies were carried out by pretreating the mice i.p. with either saline or cocaine 6 min before nicotine.

Nicotine Drug Discrimination in Rats

Rats were individually housed in a temperature-controlled environment and were maintained on a diet (Agway Rodent Chow) that restricted their body weight to approximately 85% of their free feeding weight. Water was available ad libitum in the home cages. A two-lever operant drug nation paradigm (VI 15) was carried out in eight operant chambers (4 Lafayette model 80001 and 4 BRS/LVIE model s 002). Reinforcement was a Bioserv 45-mg precision dustless pellet. Data were collected automatically by two Commodore 64 microcomputers.

Rats were trained to respond on one lever after a s.c. injection of -(−)-nicotine (0.4 mg/kg) and another lever after a s.c. injection of saline. Rats were placed in an operant chamber 5 min after injections. The specific procedure for training rats to discriminate between nicotine and saline has been described previously (Rosecrans, 1989). Animals were required to meet a criterion of three successive days of 80% or greater correct-lever responding before testing was initiated. Injections were given 5 min before placing the animal in the operant chamber. The schedule of injections, was determined using a Latin Square design. Dose-response curves were determined for nicotine 5 min after s.c. injections. For antagonism testing, animals were assessed for the behavioral effects of cocaine in conjunction with the training dose of nicotine. Cocaine war, administered 10 min before the injection of (–)-nicotine.

Oocyte Expression Studies

Oocyte Preparation. Oocyte preparation was performed according to the method of Mirshahi and Woodward (1995) with minor modifications. Briefly, oocytes were isolated from female adult oocyte-positive Xenopus laevis frogs. Frogs were anesthetized in a 0.2% 3-aminobenzoic acid ethyl ester solution (Sigma Chemical Co.) for 30 min and a fraction of the ovarian lobes were removed. The eggs were rinsed in $Ca^{2+}$-free ND96 solution, treated with collagenase type IA (Sigma Chemical Co.) for 1 h to remove the follicle layer, and then rinsed again. Healthy stage V–VI oocytes were selected and maintained for up to 14 days after surgery in 0.5×L-15 media.

mRNA Preparation and Microinjection. $\alpha_4$, $\alpha_3$ and $\beta_2$ rat subunit cDNA contained within a pcDNAIneo vector were kindly supplied by Dr. James Patrick (Baylor College of Medicine, Houston, Tex.). The template was linearized downstream of the coding sequence and mRNA was synthetized using an in vitro transcription kit from Ambion (Austin, Tex.). The quantity and quality of message were determined via optical density (spectrophotometer; Beckman Instruments Inc., Schaumburg, Ill.) and denaturing formaldehyde gel analysis. Oocytes were injected with either 51 ng (41 nl) of $\alpha_4$ and $\beta_2$ and $\alpha_3$ and $\beta_2$ mRNA mixed in a 1-1 ratio using a Variable Nanoject (Drummond Scientific Co., Broomall, Pa.). Oocytes were incubated in 0.5×L-15 media IA (Sigma Chemical Co.) supplemented with penicillin, streptomycin, and gentimycin for 4 to 6 days at 19° C. before recording.

Electrophysiological Recordings. Oocytes were placed within a Plexiglas chamber (total volume 0.2 ml) and continually perfumed (10 ml/min) with buffer consisting of 116 mM NaCl, 1.8 mM $CaCl_2$, 2.5 mM KCl, 1.0 $\mu$M atropine, and 10.0 mM HEPES at pH 7.2. Oocytes were impaled with two microelectrodes containing 3 M KCl (0.3–3 M$\Omega$) and voltage-clamped at –70 rm using an Axon Geneclamp amplifier (Axon Instruments Inc., Foster City, Calif.). Oocytes were stimulated for 10 s with various concentrations of acetylcholine and nicotine using a six-port injection valve. Except where noted, applications were separated by 5-min periods of washout. Currents were filtered at 10 Hz and collected by a Macintosh Centris 650 computer with a 16-bit analog digital interface board, and data were analyzed using Pulse Control voltage-clamp software running under the Igor Pro graphic platform (Wavemetrics, Lake Oswego, Oreg.). Drugs were applied at different concentrations and concentration-response curves were normalized to the current induced by 1 $\mu$M ($\alpha_4\beta_2$ receptors) or 10 $\mu$M ($\alpha_3\beta_2$ receptors) of acetylcholine. The normalizing concentration of acetylcholine war, applied before and after drug application to each oocyte to check for desensitization. Data were rejected if responses to the normalizing dose fell below 75% of the original responses.

Statistical Analysis

Data were analyzed statistically by an analysis of variance followed by the Fisher's P least-significant difference multiple comparison test. The null hypothesis was rejected at the 0.06 level. $ED_{50}$, $EC_{50}$, and $AD_{50}$ (antagonist dose 50%) values with 95% CLs were calculated by unweighted least-squares linear regression as described by Tallarida and Murray (1987).

Results

Effect of cocaine Analogs on Nicotine-induced Antinociception in Mice. Cocaine and its derivatives, the structures of which are described in Table 1, were evaluated for their ability to antagonize a 2.5 mg/kg dose of nicotine in the tail-flick procedure. Cocaine as well as all of its analogs, with the exception of RTI-70, produced dose dependent inhibition of nicotine's antinociceptive effect. Their antagonistic potencies are presented in Table 2, and dose-response curves of cocaine and selected analogs are shown in FIG. 1. The letter demonstrates that the antinociceptive effects of nicotine can be completely blocked by these agents. By themselves, these analogs did not produce significant effects on tail-flick latencies at any of the doses tested.

In regard to the structure activity relationship of the 3-phenyltropane analogs, the effects of substitution on the aromatic ring, of changes in the 2$\beta$-substituent, and of removal of the N-methyl group were investigated. Because compounds RTI-29, -32, -51, -96, -111, and -112 differ only in their aromatic substituents, a comparison of the results from these compounds reveals the effect of these substituents. The 4-bromo analog (RTI-51) and the 3,4-dichloro analog (RTI-111) were approximately 3-fold and 2.5-fold, respectively, more potent than cocaine in blocking nicotine's antinociceptive effect. The 4-methyl analog (RTI-32) was slightly more potent than cocaine, the 3-methyl-4-chloro analog (RTI-112) had approximately the same activity as cocaine, and the 4-amino analog (RTI-29) was one-half as potent as cocaine. RTI-120, which differs from RTI-32 by having a phenyl ester substituent in the 2-position, is only one-half as potent as RTI-32. The 2$\beta$-phenyl ester (RTI-113), which also has a 4-chloro substituent, was even less potent. In contrast, RTI-121, which is a 2$\beta$-isopropyl ester possessing a 4-iodo substituent, was 10-fold more potent than cocaine, The 2$\beta$-pyrrolidlinoamide analog (RTI-147), which has a 4-chloro substituent, was about one-half as potent as cocaine, whereas the 2$\beta$-pyrrolidinoamide (RTI-229), which has a 4-iodo substituent, possessed about the same potency as cocaine. The nortropane analog (RTI-110) was 3-fold more potent than cocaine. The 2-carboxy analog (RTI-70) and the 2$\alpha$ analog (RTI-268) were both much less potent than cocaine. WIN 36,065-2, which differs structurally from cocaine by having the aromatic ring connected directly to the 3-position of the tropane ring, was. 2.5-times less potent than cocaine. However, the addition of substituents to the aromatic ring of WIN 35,065-2 led to compounds with increased potency. A comparison of the potency of WIN 35,065-2 to those of R77-29, -32, -51, -55, -111, and -112, which differ only in their aromatic substituents, reveals the effect of these substituents. The. 4-iodo analog (RTI-55), the 4-bromo analog (RTI-5 1), the 3,4-dichloro analog (RTI-111), and the 4-methyl analog (RTI-32) were approximately 9- to 4-fold more potent than the unsubstituted analog WIN 35,065-2 in blocking nicotine's antinociceptive effect. The 3-methyl-4-chloro analog (RTI-112) was approximately twice as potent as WIN 35,065-2, and the 4-amino analog (RTI-29) had approximately the same activity as WIN 35,065-2.

As mentioned above, cocaine dose-dependently blocked nicotine-induced antinociception with an $AD_{50}$ of 3.2 $\mu$mol/kg (1 mg/kg). In addition, the dose-response curve of nicotine-induced antinociception was shifted to the right by cocaine (6 mg/kg) (FIG. 1), and the $ED_{50}$ value of nicotine was increased from 1.5 mg/kg (0.8–2.6) to 7.4 mg/kg (4.7–12.0).

Figure 3:
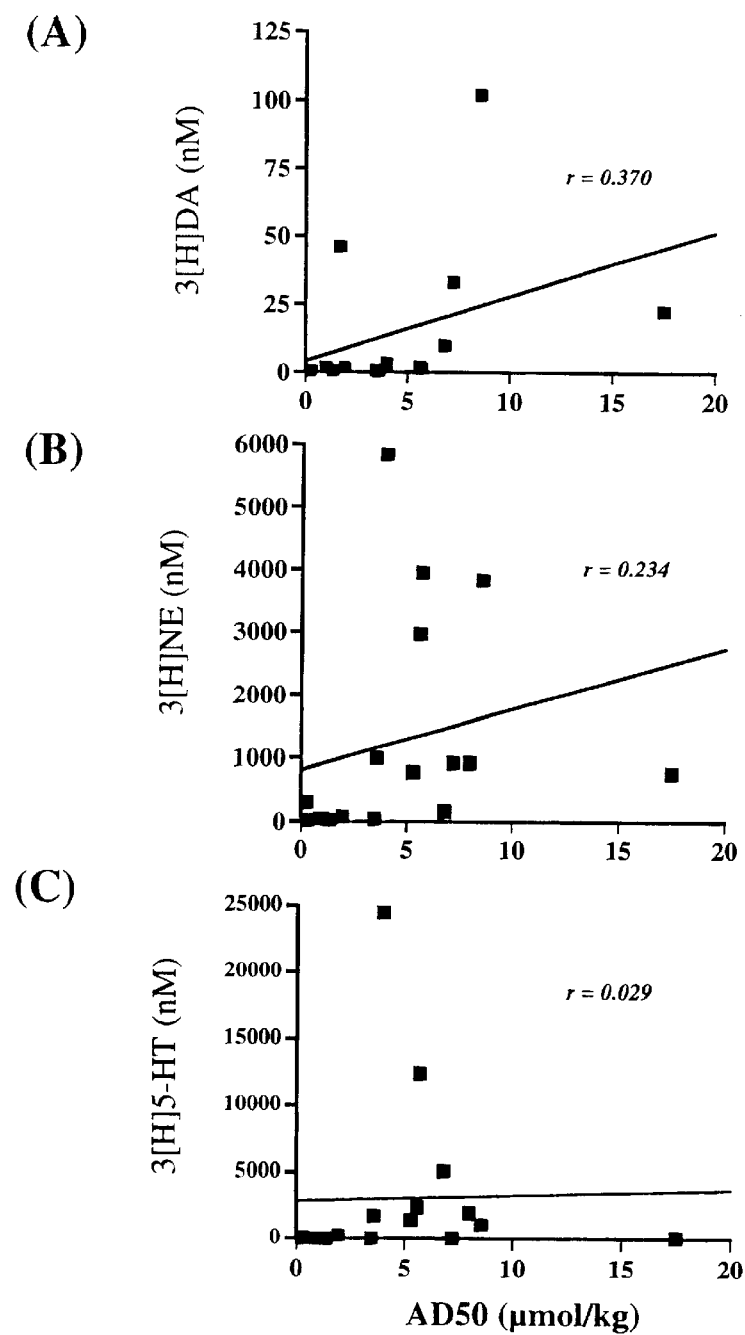
FIGS. 3(A–C): Correlation between dopamine (A), norepinephrine (B), and serotonin (C) transporter binding potencies ($IC_{50}$ expressed as nM) and nicotinic antagonistic potency ($AD_{50}$ values expressed as $\mu$mol/kg) for cocaine analogs in tail-flick test.

To determine whether these cocaine analogs could be blocking nicotine's effects through actions on neurotransporters, their potency to inhibit dopamine, norepinephrine, or serotonin transporters, was correlated with their antagonistic potency (FIG. 3). The rank-order analysis did not show any significant correlation between the potency of 3β-phenyltropane cocaine analogs in blocking nicotine's action and their affinity to the different transporters.

Figure 4:
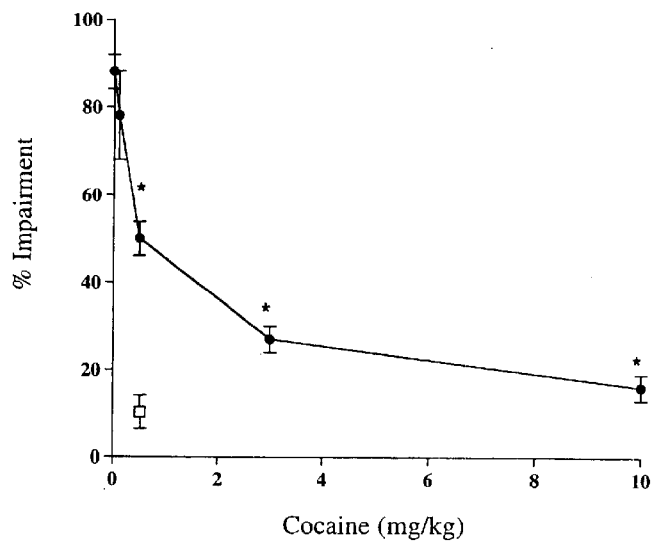
FIG. 4: Blockade of nicotine-induced motor impairment by cocaine. Cocaine was administered i.p. 10 min before nicotine and mice were tested 20 min after nicotine (2.5 mg/kg) injection. Effect of vehicle (-□-) is also represented in graph. Each point represents mean ±S.E. of 8 to 12 mice. Statistically different from nicotine (alone) at P<0.05.

Pharmacological Interaction of Nicotine and Cocaine. To further characterize cocaine/nicotine interactions, additional experiments were conducted to determine whether cocaine would attenuate several of nicotine's effects in a dose-responsive manner. Pretreatment with cocaine blocked the effect of a dose of 2.5 mg/kg of nicotine on the rotarod test in a dose-dependent manner (FIG. 4) with an $AD_{50}$ of 2 A$\mu$mol/kg (0.7 mg/kg). By itself, cocaine did not significantly alter performance on the rotarod test. Cocaine was moderately effective in antagonizing nicotine-induced seizures in mice with an estimated $AD_{50}$ of 50 $\mu$mol/kg (Table 2, Seizure activity). However, cocaine failed to significantly block the discriminative stimulus effect of nicotine in rats (Table 2, Drug discrimination). Cocaine and a selected number of analogs were also evaluated for potential blockade of nicotine-induced hypothermia. Cocaine produced little antagonism of nicotine's hypothermic effects at doses that were 10-fold greater than those effective for antinociceptive blockade (Table 2, Body temperature). Among the cocaine analogs tested, RTI-31, -32, -55, -112, -121, and WIN 35,065-2 significantly blocked nicotine-induced hypothermia in mice, with RTI-31 being the most potent blocker ($AD_{50}$ of 1.1 $\mu$mol/kg) (Table 1). Interestingly, RTI-31 was 6.5-fold more potent in blocking nicotine hypothermia than antinociception, whereas RTI-32 and RTI-121 were 15-fold and more than a 100-fold less potent, respectively.

To assess a bidirectional cross-reactivity between cocaine and nicotine, dihydro-β-erythroidine (DHβE) and mecamylamine were evaluated for their ability to influence cocaine-induced hyperactivity in mice. Indeed, pretreatment with DHβE and mecamylamine at 1 mg/kg administered s.c. 10 min before the injection of cocaine (15 mg/kg, i.p.) did not significantly reduced the hypermotility induced by cocaine (FIG. 5). Higher doses of DHβE and mecamylamine could not be tested because they significantly decreased mouse spontaneous activity.

Figure 6:
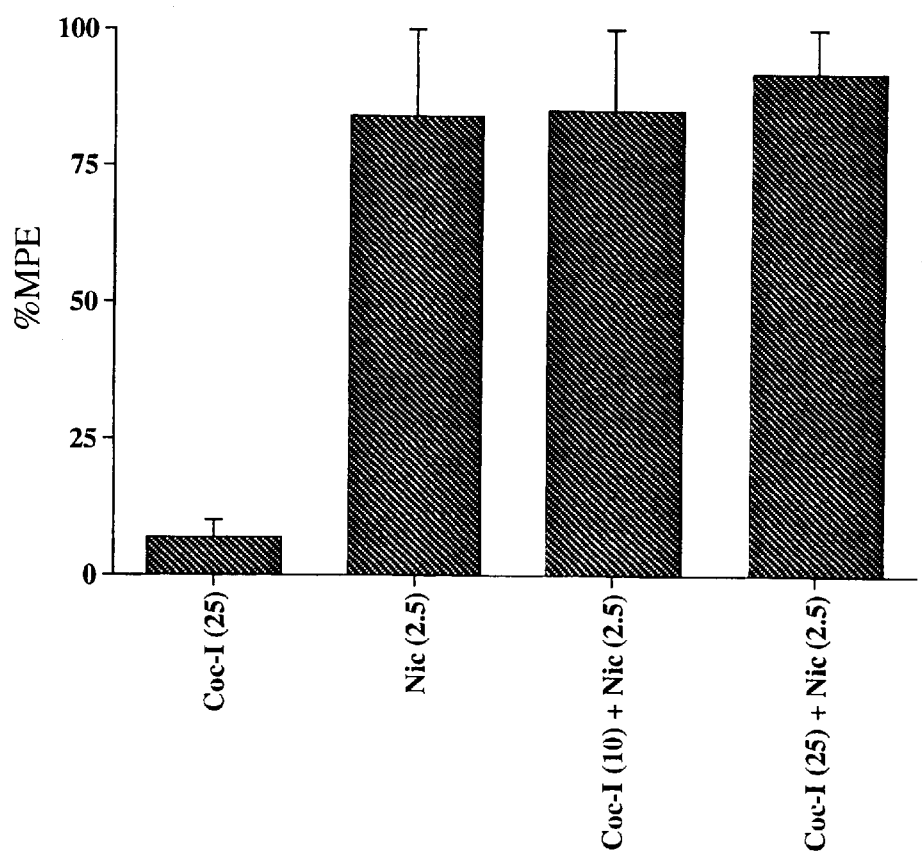
FIG. 6: Lack of blockade of nicotine-induced antinociception by cocaine-methiodide after i.p. administration in mice using tail-flick test. Cocaine-methiodide (at 10 and 25 mg/kg) injection. Each point represents mean ±S.E. of 8 to 12 mice. Coc-I, cocaine-methiodide; Nic, nicotine.

Mechanisms of Antagonistic Effect of Cocaine in Tail-Flick Test. To ascertain that the cocaine/nicotine interaction was taking place centrally, cocaine methiodide was evaluated as a potential nicotinic antagonist. As seen in FIG. 6 cocaine methiodide given at doses 10 and 25 times higher than the $AD_{50}$ dose of cocaine (1.1 mg/kg) failed to significantly block nicotine-induced antinociception in mice.

The most prominent central nervous system effects of cocaine are thought to be mediated through blockade of neurotransmitter transporters. Nomifensine, GBR 12909, and bupropion, which are monoamine uptake inhibitors with different affinity and selectivity to the different transporters, dose-dependently blocked nicotine's antinociceptive effect in mice (Table 3). However, their potency of blockade did not correlate well with dopamine uptake inhibition. Although nomifensine and GBR 12909 inhibit dopamine uptake with similar affinity, nomifensine was five times more potent than GBR 12909 as a blocker. In addition, bupropion, a nonselective weak dopamine uptake inhibitor (micromolar range) was as potent as GBR 12909 in blocking nicotine's action. In contrast, methylphenidate, a nonselective monoamine uptake inhibitor, failed to block nicotine's effect. Furthermore, dopaminergic and nondopaminergic central stimulants, such as amphetamine and caffeine, blocked nicotine-induced antinociception (Table 4).

Fluoxetine, a selective serotonin uptake inhibitor, failed to significantly block (Table 4) or enhance the effects of nicotine in the tail-flick test. However, nisoxetine, a selective inhibitor of the norepinephrine transporter, antagonized nicotine-induced antinociception in a dose-related manner, with an $AD_{50}$ value of 7.4 $\mu$mol/kg (2.3 mg/kg).

Finally, because cocaine is known to possess local anesthetic properties, lidocaine and procaine, two local anesthetics, were evaluated as nicotinic antagonist. However, they failed to significantly block (Table 3) or enhance the effects of nicotine, when injected at high doses (up to 75 $\mu$mol/kg) into mice.

Figure 7:
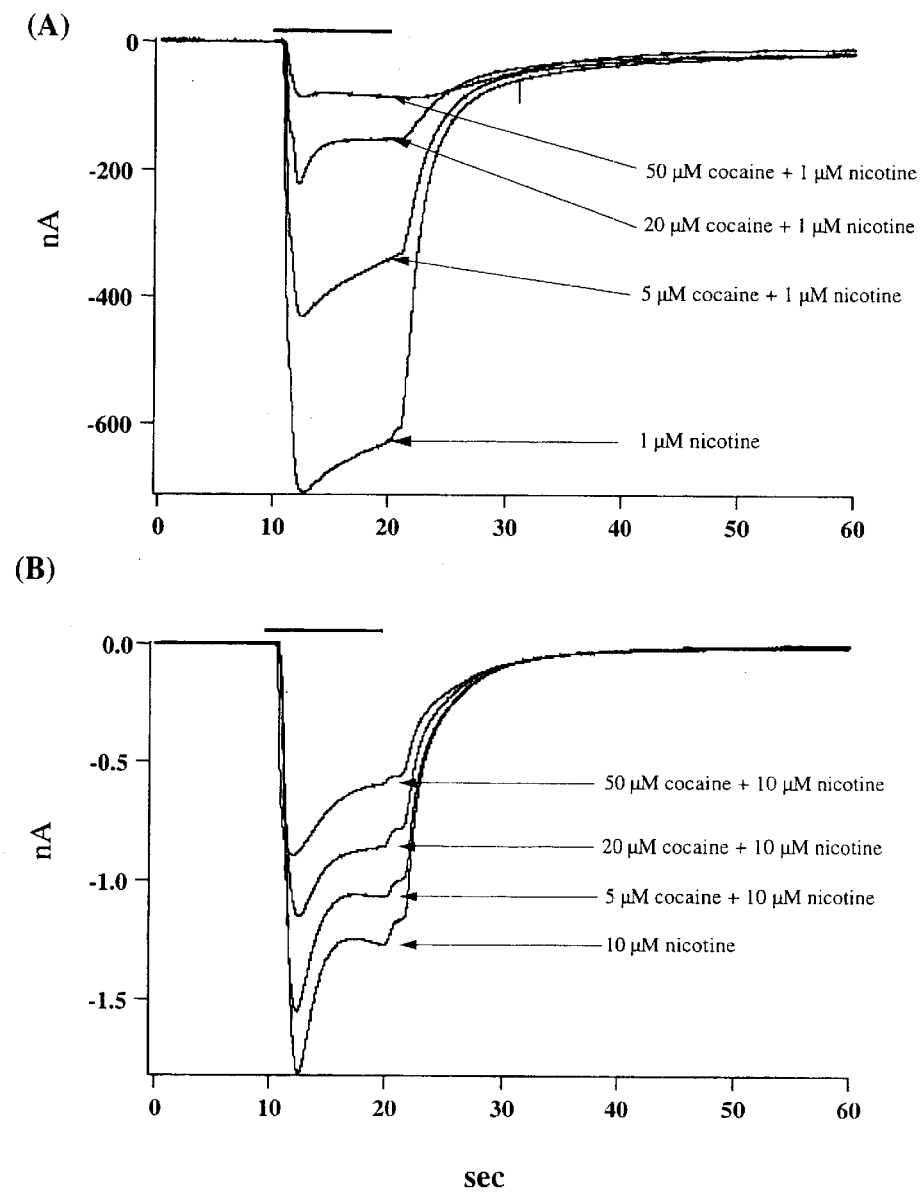
FIGS. 7(A–B): Effect of different concentrations of cocaine on current activated by 1 $\mu$M nicotine (A) applied in $\alpha_3\beta_2$-expressing oocytes and 10 $\mu$M nicotine (B) applied in $\alpha_3\beta_2$-expressing oocytes. Nicotine or cocaine was applied as a 10-s pulse and changes in current from baseline values was measured for a total of 1 min. Oocytes were held at –70 mV.

$\alpha_4\beta_2$ and $\alpha_3\beta_2$ Expressed Receptor in Oocytes. Cocaine at 100 $\mu$M elicited little current when applied for 10 s to oocytes expressing the $\alpha_4\beta_2$ and $\alpha_3\beta_2$ subunit combination. Although it did not activate $\alpha_4\beta_2$ and $\alpha_3\beta_2$-expressed receptors, cocaine antagonized the effects of nicotine in a concentration-related manner. Indeed, the current induced by nicotine was blocked by coapplication of cocaine at different concentrations (FIG. 7). The concentration of cocaine that blocked 50% of the nicotinic current was determined to be 5.5 AM (range, 4.4–6.9) and 30.5 AM (range, 22–42.3) for $\alpha_4\beta_2$ and $\alpha_3\beta_2$ receptors, respectively.

TABLE 1

Structure of cocaine analogs tested as nicotinic antagonists

| RTI # | $R_1$ | $R_2$ | X | Y |
|---|---|---|---|---|
| Cocaine | $CO_2CH_3$ | $CH_3$ | H | H |
| WIN 33,065-2 | | | | |
| 29 | $CO_2CH_3$ | $CH_3$ | $NH_2$ | H |
| 31 | $CO_2CH_3$ | $CH_3$ | Cl | H |
| 32 | $CO_2CH_3$ | $CH_3$ | $CH_3$ | H |
| 51 | $CO_2CH_3$ | $CH_3$ | Br | H |
| 55 | $CO_2CH_3$ | $CH_3$ | I | H |
| 70 | $CO_2H$ | $CH_3$ | Cl | H |
| 110 | $CO_2CH_3$ | H | Cl | H |
| 111 | $CO_2CH_3$ | $CH_3$ | Cl | Cl |
| 112 | $CO_2CH_3$ | $CH_3$ | Cl | $CH_3$ |
| 113 | $CO_2C_6H_5$ | $CH_3$ | Cl | H |
| 114 | $CO_2CH(CH_3)_2$ | $CH_3$ | Cl | H |
| 120 | $CO_2C_6H_5$ | $CH_3$ | $CH_3$ | H |
| 121 | $CO_2CH(CH_3)_2$ | $CH_3$ | I | H |
| 147 | CON⟨⟩ | $CH_3$ | Cl | H |
| 229 | CON⟨⟩ | $CH_3$ | I | H |
| 258 | $CO_2CH_3$[a] | $CH_3$ | I | H |

[a] The $CO_2CH_3$ group has a 2α orientation.

TABLE 2

Comparison of pharmacological potencies of tropane analogs in blocking nicotine-induced antinociception (tail-flick test) and hypothermis after systemic administration to their binding affinities to [$^3$H]monoamine transporters in brain

| Analog | AD$_{50}$ Tail-Flick μmol/hg | AD$_{50}$ Hypothermia μmol/hg | Dopamine [$^3$H]WIN 35,428 IC$_{50}$ nM | Serotonin [$^3$H]Paroxetine IC$_{50}$ nM | Norepinephrine [$^3$H]Nisoxetime IC$_{50}$ nM |
|---|---|---|---|---|---|
| Cocaine | 3.2 | 20% @ 32 | 102 | 1060 | 3830 |
| RTI-29 | 6.8 | NT[b] | 9.8 | 5110 | 151 |
| RTI-31 | 7.2 | 1.1 | 1.12 | 44.5 | 37 |
| RTI-32 | 2.0 | 31.7 | 1.7 | 240 | 60 |
| RTI-51 | 1.0 | NT[a] | 1.69 | 10.6 | 37.4 |
| RTI-55 | 0.9 | 1.2 | 1.26 | 4.2 | 63 |
| RTI-70 | 0% @ 90 | 40% @ 90 | 2070 | 59,500 | >200,000 |
| RTI-110 | 1.0 | NT[b] | 0.62 | 4.1 | 5.45 |
| RTI-111 | 1.3 | NT[b] | 0.79 | 3.1 | 17.9 |
| RTI-112 | 3.5 | 1.5 | 0.8 | 10.5 | 36.2 |
| RTI-113 | 5.6 | NTb | 1.98 | 2340 | 2926 |
| RTI-114 | 5.3 | 9 | 1.4 | 1404 | 778 |
| RTI-120 | 4.0 | NT[b] | 3.26 | 24,500 | 5830 |
| RTI-121 | 0.3 | 49 | 0.4 | 66.8 | 285 |
| RTI-147 | 5.7 | NT[b] | 1.38 | 12,400 | 3950 |
| RTI-229 | 3.6 | NT[b] | 0.37 | 1790 | 990 |
| RTI-258 | 19.1 | NT[b] | 22.7 | 66.3 | 760 |
| WIN 35,065-2 | 8.0 | 6.7 | 23 | 1962 | 920 |

[a](Carroll et al., 1991, 1992, 1995; Lewin et al., 1992).
[b]NT, not tested.

TABLE 3

Effect of cocaine pretreatment on different pharmacological actions of nicotine after a.c. administration mice and rats

| Pretreatment Dose[a] | Challenge Dose[a] | Response[b] |
|---|---|---|
| | Body temperature[b] | t° C. (Mean ± SE) |
| Saline | Saline | −0.3 ± 0.2 |
| Saline | Nicotine (3) | −5.2 ± 0.2 |
| Cocaine (10) | Saline | 0.5 ± 0.1 |
| Cocaine (10) | Nicotine (3) | −4.1 ± 0.6 |
| | Seizure activity | % Seizures (Mean) |
| Saline | Nicotine (9) | 100 |
| Saline | Cocaine (20) | 0 |
| Cocaine (10) | Nicotine (9) | 83.3 |
| Cocaine (20) | Nicotine (9) | 50[c] |
| Cocaine (30) | Nicotine (9) | 16[c] |
| | Drug discrimination | % Test (Mean ± SE) |
| Saline | Nicotine (0.4) | 87 ± 8 |
| Saline | Cocaine (10) | 17 ± 7 |
| Cocaine (10) | Nicotine (0.4) | 69 ± 8 |

[a]Doses are expressed in mg/kg in parenthesis.
[b]Mice were challenged with nicotine 10 min after i.p. administration of cocaine.
[c]P < .05 from saline/nicotine (9).

TABLE 4

Effect of various neurotransmitter uptake inhibitors, stimulants, and NA$^+$ channel blockers on nicotine-induced antinociception in tail-flick test after s.c. administration

| Drug | AD$_{50}$ μmol/hg |
|---|---|
| Bupropion | 8 |
| GBR 12909 | 8.4 |
| Nomifensine | 1.7 |
| Amphetamine | 36.9 |
| Methylphenidate | 5% @ 74 |
| Caffeine | 32.4 |
| Nisoxetine | 7.4 |
| Fluoxetine | 15% @ 86.7 |

TABLE 4-continued

Effect of various neurotransmitter uptake inhibitors, stimulants, and NA$^+$ channel blockers on nicotine-induced antinociception in tail-flick test after s.c. administration

| Drug | AD$_{50}$ μmol/hg |
|---|---|
| Lidocaine | 7% @ 75 |
| Procaine | 5% @ 75 |

Obviously, numerous modifications and variations of the present invention are possible in light of the above teachings. It is therefore to be understood that within the scope of the appended claims, the invention may be practiced otherwise than as specifically described herein.

REFERENCES

Aceto M D, Martin B R, Uwaydab, I M, May E L., Harris L S, Izazola-Conde C, Dewey W L and Vincek W C (1979) Optically pure (+)-nicotine from (±)-nicotine and biological comparisons with (−)-nicotine, *J. Med. Chem.*, 22:174–177.

Ascher J A, Cole J O, Colin J-N, Feigher, J P, Farris R M, Fibiger J C, Golden R N, Martin P, Potter W Z, Richelson E and Sulser F (1995) Bupropion: A review of its mechanism of antidepressant activity *J. Clin. Psych.* 56:395–401.

Assaro A J, Ziance R J and Rutledge C O (1974). The importance of neuronal uptake of amines for amphetamine-induced release of 3H-norepinephrine from isolated brain tissue *J. Pharmacol. Exp. Ther.* 189:110–116.

Carroll F I, Abraham P, Lewin A H, Parham K A, Boja J W and Kuhar M J (1992) Isopropyl and phenyl esters of 3β-(4-substituted phenyl)tropan-2β-carboxylic acids. Potent and selective compounds for the dopamine transporter. *J Med. Chem.* 35:2497–2500.

Carroll, F I, Gao Y, Abdur Rahman M, Abraham P, Parham K A, Lewin A H, Boja J W and Kuhar M J (1991). Synthesis, ligand binding, QSAR, and CoMFA study of 3β-(p-substituted phenyl)tropan-3β-carboxylic acid methyl esters. *J. Med. Chem.* 34:2719–1725.

Court J A, Piggott M A, Perry E K, Barlow R B and Perry R H (1992) Age associated decline in high affinity nicotine binding in human brain frontal cortex does not correlate with the changes in choline acetyltransferase activity. *Neurosci. Res. Commun.* 10:125–138.

D'Amour F E and Smith D L (1941) A method for determining loss of pain sensation. *J Pharmacol. Exp. Ther.* 72:74–79.

Damaj M I and Martin B R (1993) Is the dopaminergic system involved in the central effects of nicotine in mice. *Psychopharmacology* 111: 106–108.

Damaj M I, Fei-Yin M, Dukat M, Glassco W, Glennon R A and Martin B R (1998) Antinociceptice responses to nicotinic acetylcholine receptor ligands after systemic and intrathecal administration in mice. *J. Pharmacol. Ex. Ther.* 294:1058–1065.

Damaj M I, Welch S P and Martin B R (1995) In vivo pharmacological effects of dihydro-β-erythroidine, and nicotinic antagonist in mice. *Psychopharmacology* 117:67–78.

Dewey W L, Harris L S, Howes J S and Nuite J A (1970) The effect of various neurohormonal modulations on the activity of morphine and the narcotic antagonists in tail-flick and phenylquinone test. *J. Pharmacol. Exp. Ther.* 175:435–442.

Donnelly-Roberts D, Americ S and Sullivan J P (1995) Functional modulation of human "ganglionic-like" neuronal nicotinic acetylcholine receptors (nAChRs) by L-type calcium channel antagonists. *Biochem. Biophys. Res. Commun.* 213:657–662.

Fleckenstein A E, Kopajtic T A, Boja J W, Carroll F I and Kuhar M J (1995) Highly potent cocaine analogs cause long-lasting increase in locomotor activity. *Eur. J. Pharmacol.* 311:109–114.

Grady S, Marks M J, Wonnacott S and Collins A C (1992) Characterization of nicotinic receptor-mediated [$^3$H] dopamine release from synaptosomes prepared from mouse striatum. *J. Neurochem.* 59:848–856.

Higgins S T, Budney A J, Hughes J R, Bickel W K, Lynn M and Mortensen A (1994) Influence of cocaine use on cigarette smoking. *J. Am. Med. Assoc.* 272:1724–1724.

Horger B A, Giles M K and Schenk S (1992) Preexposure to amphetamine and nicotine predisposes rate to self-administer a low dose of cocaine. *Psychopharmacology* 107:271–276.

Hurt R D, Sachs D P L, Glover E D, Offord K P, Johnston J A, Dale L C, Khayrallah M A, Schroeder D R, Glover P N, Sullivan C R, Croghan I T and Sullivan P M (1997). A comparison of sustained-release bupropion and placebo for smoking cessation. *N Eng. J. Med.* 337:1195–1202.

Isenwasser S and Koretsky C (1988) Potentiation of morphine analgesis by d-amphetamine is mediated by norepinephrine and not dopamine. *Pain* 33:363–368.

Ke L and Lukas R J (1996) Effects of steroid exposure on ligand binding and functional activities of diverse nicotinic acetylcholine receptor subtypes. *J. Meurochem.* 67:1100–1111.

Kuhar M J, Ritz M C and Boja J W (1991) The dopamine hypothesis of the reinforcing effect of cocaine, *Trends Neurosci.* 14:299–302.

Leonard R J, Charnet P, Labarca C, Vogelaar N, Czyzyk L, Gouinn A, Davidson N and Lester H A (1995) Reverse pharmacology of the nicotinic acetylcholine receptor. *Ann NY Acad. Sci.* 586–599.

Lerner-Mamarosh N, Carroll F I and Abood L G (1995) Antagonism of nicotine's action by cocaine analogs. *Life Sci.* 56:67–70.

Lewin A H, Gao Y, Abraham P, Boja J W, Kuhar M J and Carroll F I (1992) 2β-Substituted analogues of cocaine, Synthesis and inhibition of binding to the cocaine receptor. *J. Med. Chem.* 35:135–140.

Lu W Y and Bieger D (1996) Inhibition of nicotinic cholinoceptor mediated current in vagal motor neurons by local anesthetics. *Can. J Physiol. Pharmacol.* 74:1265–1269.

Lukas R J and Eisenhour C M (1996) Interactions between tachykinine and diverse human nicotinic acetylcholine receptor subtypes. *Neurochem. Res.* 91:1245–1257.

Marks M J and Collins A C (1982) Characterization of nicotine binding in mouse brain and comparison with the binding of alpha-bungarotoxin and quinuelidinyl benzilate. *Mol. Pharmacol.* 22:554–564.

Miner L L and Collins A C (1989) Strain comparison of nicotine-induced seizure sensitivity and nicotinic receptors. *Pharmacol. Biochem. Behav.* 33:469–475.

Miner L L, Marks M J and Collins A C (1985) Relationship between nicotine-induced seizures and hippocampal nicotinic receptors. *Life Sci.* 37:75–83.

Mirahahi T and Woodward J J (1995) Ethanol sensitivity of heteromeric NMDA receptors. Effects of subunit assembly, glycine and NMDAR1 Mg++insensitive mutants. *Neuropharmacology* 34:347–355.

Richelson E and Pfenning M (1984) Blockade by antidepressants and related compounds of biogenic amine uptake into rat brain synaptosomes: Most antidepressnats selectively block norepinephrine uptake. *Eur. J. Pharmacol.* 104:277–286.

Rosecrans J A (1989) Nicotine as a discriminative stimulus: A neurobiobehavioral approach to studying central cholinergic mechanisms. *J. Subst. Abuse* 1:287–300.

Swanson K L and Albuquerque E X (1987) Nicotinic acetylcholine receptor ion channel blockage by cocaine: The mechanism of synaptic action. *J. Pharmacol. Exp. Ther.* 243:1202–1210.

Tallaride R J and Murray R B (1987) *Manual of Pharmacological Calculations with Computer Programs*, Springer-Verlag, New York.

Wong T T and Bymaster F T (1976) Effect of nisoxetine on uptake of catacholamines in synaptosomes isolated from discrete regions of rat brain. *Biochem. Pharmacol.* 25:1979–1983.

Zernig G, O'Laughun I A and Fibiger H C (1997) Nicotine and heroin agument cocaine-induced dopamine overflow in nucleus accumbens. *Eur. J. Pharmacol.* 337:1–10.

What is claimed is:

1. A method of training a smoker to cease smoking, comprising administering to the smoker an effective amount of a tropane compound represented by the formula:

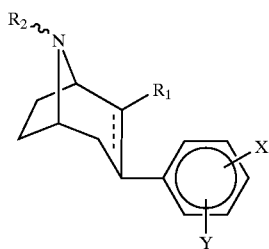

wherein $R_1$ is $CO_2R_3$, $CONR_4R_5$, $R_6$, $CH_2R_6$,

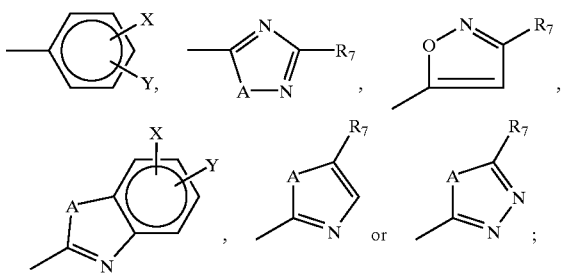

$R_3$ is H, $C_{1-6}$alkyl, $C_{3-8}$cycloalkyl or

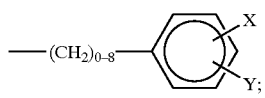

$R_4$ and $R_5$ are each independently, H, $C_{1-6}$alkyl, $C_{2-6}$alkene, $C_{2-6}$alkyne, $CH_2$—CO-phenyl, phenyl, phenyl substituted with 1–3 of $C_{1-6}$alkyl, $C_{2-6}$alkene, $C_{2-6}$alkyne or $C_{1-6}$alkoxy, hydroxy, $CH_2OH$, $C_{1-6}$alkoxy, phenoxy, amino, amino substituted with 1 or 2 $C_{1-6}$alkyl, $C_{2-6}$alkene, $C_{2-6}$alkyne, $C_{1-6}$alkoxy, $C_{1-8}$acyl, phenyl, or phenoxy, or $R_4$ and $R_5$ may combine to form, together with the nitrogen atom to which they are bonded, a cyclic structure selected from the group consisting of a pyrrolidinyl group, morpholinyl group, piperidinyl group and a group represented by the formula

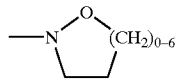

$R_6$ is OH, H, $C_{1-6}$alkyl, $C_{3-8}$cycloalkyl, $C_{1-6}$alkoxy, Cl, Br, I, CN, $NH_2$, $NHC_{1-6}$alkyl, $N(C_{1-6}alkyl)_2$, OCO—$C_{1-6}$alkyl, OCO—$C_{13}$alkylaryl, $CO_2$—$C_{1-6}$alkyl, $CO_2$—$C_{1-3}$alkyl, or substituted phenoxy;

$R_7$ is H, $C_{1-6}$alkyl, $C_{3-8}$cycloalkyl, $C_{1-6}$alkoxy, $C_{2-6}$alkynyl, halogen, amino or;

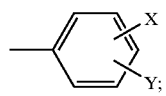

A is S, O or NH;

$R_2$ is H, $C_{1-5}$alkyl, halogenated $C_{1-6}$alkyl, $C_{2-6}$alkenyl or $(CH_2)_nCO_2R_t$ where n is an integer of 1 to 8 and $R_x$ is $C_{1-6}$alkyl;

each X is, independently, H, $C_{1-6}$alkyl, $C_{3-8}$cycloalkyl, $C_{1-6}$alkoxy, $C_{2-6}$alkynyl, phenyl, $C_{1-6}$-phenyl, halogen, amino, or acylamido, $CR_z=CR_zR_z$, $CR_zR_z$—CH=$CR_zR_z$, C≡$CR_z$, C(=$R_zR_z$)$R_z$;

each $R_z$ is, independently, H, $C_{1-6}$alkyl, phenyl, substituted phenyl, $CH_2OH$, $C_{1-6}$-phenyl;

each Y is, independently, H, I, Br, Cl, F, CN, $CF_3$, $NO_2$, $N_3$, $OR_8$, $CO_2NH_2$, $CO_2R_8$, $C_{1-6}$alkyl, $NR_9R_{10}$, $NHCOR_{11}$ or $NHCO_2R_{12}$;

$R_8$ is H or $C_{1-6}$alkyl; and $R_9$, $R_{10}$, $R_{11}$, and $R_{12}$ are each, independently, H or $C_{1-6}$alkyl, or X and Y, taken together with the phenyl group to which they are bonded, form a 2-naphthyl group, the dotted line between $C_2$ and $C_3$ represents an optional double bond, or a pharmaceutically acceptable salt thereof.

2. The method of claim 1, wherein $R_2$ is H.

3. The method of claim 1, wherein $R_1$ is $CO_2R_3$ or $CONHR_4R_5$;

$R_2$ is H or $C_{1-5}$alkyl;

X is H, $C_{1-6}$alkyl, halogen or amino; and

Y is H, $C_{1-6}$alkyl or halogen.

4. The method of claim 3, wherein $R_3$ is H, $C_{1-6}$alkyl, $C_{3-8}$cycloalkyl or phenyl;

$R_4$ and $R_5$ are each, independently, H or $C_{1-6}$alkyl, or combine to form a cyclic structure selected from the group consisting of pyrrolidinyl, morpholinyl and piperidinyl moieties; and said halogen is I, Br or Cl.

5. The method of claim 4, wherein $R_3$ is H, $C_{1-6}$alkyl or phenyl; and $R_4$ and $R_5$ combine to form a cyclic structure selected from the group consisting of pyrrolidinyl, morpholinyl and piperidinyl moieties.

6. The method of claim 1, wherein said tropane compound is administered transdermally or orally to said smoker.

7. The method of claim 1, wherein $R_1$ and the $C_3$ phenyl group are cis oriented.

8. The method of claim 1, wherein said tropane compound is enriched in the (+) entantiomer.

9. The method of claim 1, wherein said tropane compound is enriched in the (−) entantiomer.

10. The method of claim 1, wherein said tropane compound is administered concurrent with an act of smoking.

11. The method of claim 1, wherein said tropane compound is administered prior to smoking.

12. A method of preventing an addiction to smoking in an occasional smoker, comprising:

administering to the occasional smoker an effective amount of a tropane compound represented by the formula:

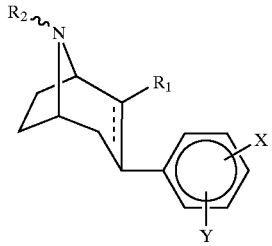

wherein $R_1$ is $CO_2R_3$, $CONR_4R_5$, $R_6$, $CH_2R_6$,

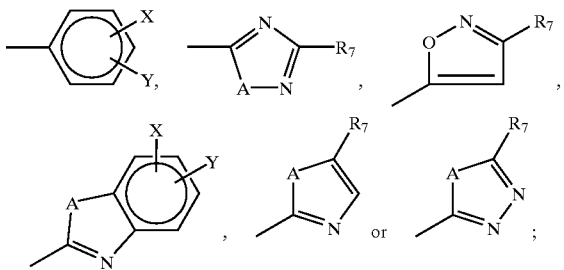

$R_3$ is H, $C_{1-6}$alkyl, $C_{3-8}$cycloalkyl or

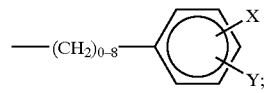

$R_4$ and $R_5$ are each independently, H, $C_{1-6}$alkyl, $C_{2-6}$alkene, $C_{2-6}$alkyne, $CH_2$—CO-phenyl, phenyl, phenyl substituted with 1–3 of $C_{1-6}$alkyl, $C_{2-6}$alkene, $C_{2-6}$alkyne or $C_{1-6}$alkoxy, hydroxy, $CH_2OH$, $C_{1-6}$alkoxy, phenoxy, amino, amino substituted with 1 or 2 $C_{1-6}$alkyl, $C_{2-6}$alkene, $C_{2-6}$alkyne, $C_{1-6}$alkoxy, $C_{1-8}$acyl, phenyl, or phenoxy, or $R_4$ and $R_5$ may combine to form, together with the nitrogen atom to which they are bonded, a cyclic structure selected from the group consisting of a pyrrolidinyl group, morpholinyl group, piperidinyl group and a group represented by the formula

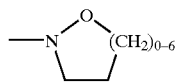

$R_6$ is OH, H, $C_{1-6}$alkyl, $C_{3-8}$cycloalkyl, $C_{1-6}$alkoxy, Cl, Br, I, CN, $NH_2$, $NHC_{1-6}$alkyl, $N(C_{1-6}$alkyl$)_2$, OCO—$C_{1-6}$alkyl, OCO—$C_{1-3}$alkylaryl, $CO_2$—$C_{1-6}$alkyl, $CO_2$—$C_{1-3}$ alkylaryl, or substituted phenoxy;

$R_7$ is H, $C_{1-6}$alkyl, $C_{3-8}$cycloalkyl, $C_{1-6}$alkoxy, $C_{2-6}$alkynyl, halogen, amino or;

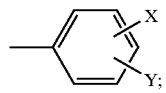

A is S, O or NH;

$R_2$ is H, $C_{1-5}$alkyl, halogenated $C_{1-6}$alkyl, $C_{2-6}$alkenyl or $(CH_2)_nCO_2R_x$, where n is an integer of 1 to 8 and $R_x$ is $C_{1-6}$alkyl;

each X is, independently, H, $C_{1-6}$alkyl, $C_{3-8}$cycloalkyl, $C_{1-6}$alkoxy, $C_{2-6}$alkynyl, phenyl, $C_{1-6}$-phenyl, halogen, amino, or acylamido, $CR_z=CR_zR_z$, $CR_zR_z$—$CH=CR_zR_z$, $C\equiv CR_z$, $C(=R_zR_z)R_z$;

each $R_z$ is, independently, H, $C_{1-6}$alkyl, phenyl, substituted phenyl, $CH_2OH$, $C_{1-6}$-phenyl;

each Y is, independently, H, I, Br, Cl, F, CN, $CF_3$, $NO_2$, $N_3$, $OR_8$, $CO_2NH_2$, $CO_2R_8$, $C_{1-6}$alkyl, $NR_9R_{10}$, $NHCOR_{11}$ or $NHCO_2R_{12}$;

$R_8$ is H or $C_{1-6}$alkyl; and $R_9$, $R_{10}$, $R_{11}$, and $R_{12}$ are each, independently, H or $C_{1-6}$alkyl, or X and Y, taken together with the phenyl group to which they are bonded, form a 2-naphthyl group, the dotted line between $C_2$ and $C_3$ represents an optional double bond, or a pharmaceutically acceptable salt thereof.

13. The method of claim 12, wherein said tropane compound is administered prior to smoking.

14. A method of treating nicotine addiction, comprising administering to a patient in need thereof an effective amount of a tropane compound represented by the formula:

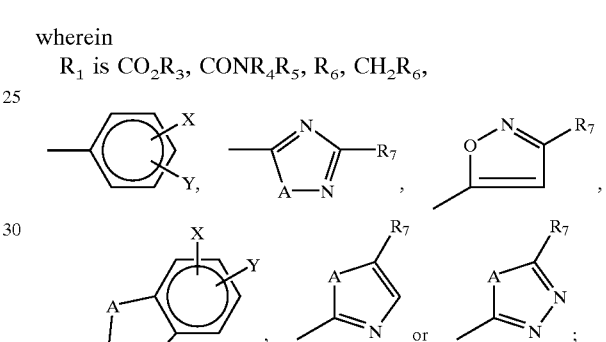

wherein $R_1$ is $CO_2R_3$, $CONR_4R_5$, $R_6$, $CH_2R_6$,

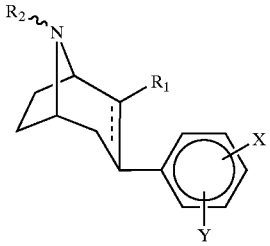

$R_3$ is H, $C_{1-6}$alkyl, $C_{3-8}$cycloalkyl or

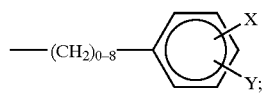

$R_4$ and $R_5$ are each independently, H, $C_{1-6}$alkyl, $C_{2-6}$alkene, $C_{2-6}$alkyne, $CH_2$—CO-phenyl, phenyl, phenyl substituted with 1–3 of $C_{1-6}$alkyl, $C_{2-6}$alkene, $C_{2-6}$alkyne or $C_{1-6}$alkoxy, hydroxy, $CH_2OH$, $C_{1-6}$alkoxy, phenoxy, amino, amino substituted with 1 or 2 $C_{1-6}$ alkyl, $C_{2-6}$alkene, $C_{2-6}$alkyne, $C_{1-6}$alkoxy, $C_{1-8}$acyl, phenyl, or phenoxy, or $R_4$ and $R_5$ may combine to form, together with the nitrogen atom to which they are bonded, a cyclic structure selected from the group consisting of a pyrrolidinyl group, morpholinyl group, piperidinyl group and a group represented by the formula

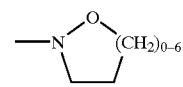

$R_6$ is OH, H, $C_{1-6}$alkyl, $C_{3-8}$cycloalkyl, $C_{1-6}$alkoxy, Cl, Br, I, CN, $NH_2$, $NHC_{1-6}$alkyl, $N(C_{1-6}$alkyl$)_2$, OCO—$C_{1-6}$alkyl, OCO—$C_{1-3}$alkylaryl, $CO_2$—$C_{1-6}$alkyl, $CO_2$—$C_{1-3}$alkylaryl, or substituted phenoxy;

$R_7$ is H, $C_{1-6}$alkyl, $C_{3-8}$cycloalkyl, $C_{1-6}$alkoxy, $C_{2-6}$alkynyl, halogen, amino or;

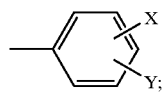

A is S, O or NH;

$R_2$ is H, $C_{1-5}$alkyl, halogenated $C_{1-6}$alkyl, $C_{2-6}$alkenyl or $(CH_2)_nCO_2R_x$, where n is an integer of 1 to 8 and $R_x$ is $C_{1-6}$alkyl;

each X is, independently, H, $C_{1-6}$alkyl, $C_{3-8}$cycloalkyl, $C_{1-6}$alkoxy, $C_{2-6}$alkynyl, phenyl, $C_{1-6}$-phenyl, halogen, amino, or acylamido, $CR_z=CR_zR_z$, $CR_zR_z-CH=CR_zR_z$, $C\equiv CR_z$, $C(=R_zR_z)R_z$;

each $R_z$ is, independently, H, $C_{1-6}$alkyl, phenyl, substituted phenyl, $CH_2OH$, $C_{1-6}$-phenyl;

each Y is, independently, H, I, Br, Cl, F, CN, $CF_3$, $NO_2$, $N_3$, $OR_8$, $CO_2NH_2$, $CO_2R_8$, $C_{1-6}$alkyl, $NR_9R_{10}$, $NHCOR_{11}$ or $NHCO_2R_{12}$;

$R_8$ is H or $C_{1-6}$alkyl; and $R_9$, $R_{10}$, $R_{11}$ and $R_{12}$ are each, independently, H or $C_{1-6}$alkyl, or X and Y, taken together with the phenyl group to which they are bonded, form a 2-naphthyl group, the dotted line between $C_2$ and $C_3$ represents an optional double bond, or a pharmaceutically acceptable salt thereof.

15. A method of training a tobacco user to cease using tobacco, comprising administering to the tobacco user an effective amount of a tropane compound represented by the formula:

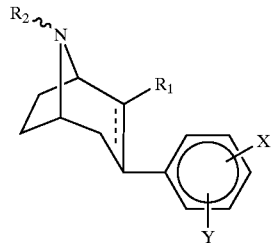

wherein $R_1$ is $CO_2R_3$, $CONR_4R_5$, $R_6$, $CH_2R_6$,

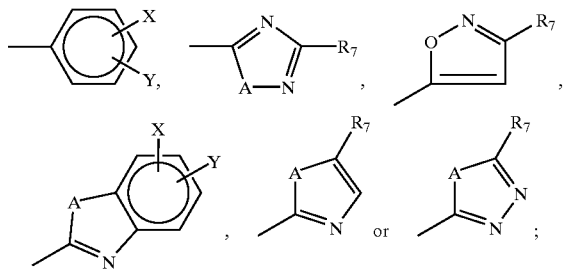

$R_3$ is H, $C_{1-6}$alkyl, $C_{3-8}$cycloalkyl or

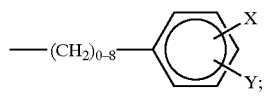

$R_4$ and $R_5$ are each independently, H, $C_{1-6}$alkyl, $C_{2-6}$alkene, $C_{2-6}$alkyne, $CH_2-CO$-phenyl, phenyl, phenyl substituted with 1–3 of $C_{1-6}$alkyl, $C_{2-6}$alkene, $C_{2-6}$alkyne or $C_{1-6}$alkoxy, hydroxy, $CH_2OH$, $C_{1-6}$alkoxy, phenoxy, amino, amino substituted with 1 or 2 $C_{1-6}$alkyl, $C_{2-6}$alkene, $C_{2-6}$alkyne, $C_{1-6}$alkoxy, $C_{1-8}$acyl, phenyl, or phenoxy, or $R_4$ and $R_5$ may combine to form, together with the nitrogen atom to which they are bonded, a cyclic structure selected from the group consisting of a pyrrolidinyl group, morpholinyl group, piperidinyl group and a group represented by the formula

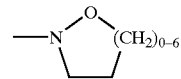

$R_6$ is OH, H, $C_{1-6}$alkyl, $C_{3-8}$cycloalkyl, $C_{1-6}$alkoxy, Cl, Br, I, CN, $NH_2$, $NHC_{1-6}$alkyl, $N(C_{1-6}$alkyl$)_2$, OCO—$C_{1-6}$alkyl, OCO—$C_{1-3}$alkylaryl, $CO_2$—$C_{1-6}$alkyl, $CO_2$—$C_{1-3}$alkylaryl, or substituted phenoxy;

$R_7$ is H, $C_{1-6}$alkyl, $C_{3-8}$cycloalkyl, $C_{1-6}$alkoxy, $C_{2-6}$alkynyl, halogen, amino or;

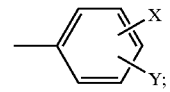

A is S, O or NH;

$R_2$ is H, $C_{1-5}$alkyl, halogenated $C_{1-6}$alkyl, $C_{2-6}$alkenyl or $(CH_2)_nCO_2R_x$, where n is an integer of 1 to 8 and $R_x$ is $C_{1-6}$alkyl;

each X is, independently, H, $C_{1-6}$alkyl, $C_{3-8}$cycloalkyl, $C_{1-6}$alkoxy, $C_{2-6}$alkynyl, phenyl, $C_{1-6}$-phenyl, halogen, amino, or acylamido, $CR_z=CR_zR_z$, $CR_zR_z-CH=CR_zR_z$, $C\equiv CR_z$, $C(=R_zR_z)R_z$;

each $R_z$ is, independently, H, $C_{1-6}$alkyl, phenyl, substituted phenyl, $CH_2OH$, $C_{1-6}$-phenyl;

each Y is, independently, H, I, Br, Cl, F, CN, $CF_3$, $NO_2$, $N_3$, $OR_8$, $CO_2NH_2$, $CO_2R_8$, $C_{1-6}$alkyl, $NR_9R_{10}$, $NHCOR_{11}$ or $NHCO_2R_{12}$;

$R_8$ is H or $C_{1-6}$alkyl; and $R_9$, $R_{10}$, $R_{11}$ and $R_{12}$ are each, independently, H or $C_{1-6}$alkyl, or X and Y, taken together with the phenyl group to which they are bonded, form a 2-naphthyl group, the dotted line between $C_2$ and $C_3$ represents an optional double bond, or a pharmaceutically acceptable salt thereof.

16. The method of claim 15, wherein said tobacco user is a smokeless tobacco user.

17. The method of claim 1, wherein $R^1$ is $CO_2CH_3$;

$R^2$ is $CH_3$;

X is chloro;

Y is methyl; and the dotted line between $C_2$ and $C_3$ represents an optional double bond.

18. The method of claim 17, wherein the compound is represented by the formula:

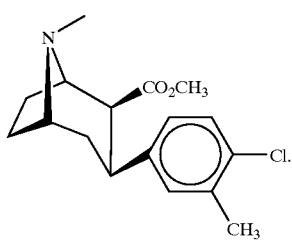

19. The method of claim 12, wherein $R^1$ is $CO_2CH_3$;

$R^2$ is $CH_3$;

X is chloro;

Y is methyl; and the dotted line between $C_2$ and $C_3$ represents an optional double bond.

20. The method of claim 19, wherein the compound is represented by the formula:

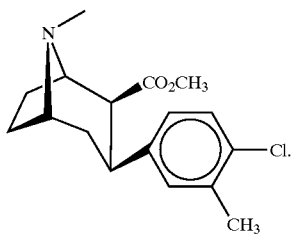

21. The method of claim 14, wherein $R^1$ is $CO_2CH_3$;

$R^2$ is $CH_3$;

X is chloro;

Y is methyl; and the dotted line between $C_2$ and $C_3$ represents an optional double bond.

22. The method of claim 21, wherein the compound is represented by the formula:

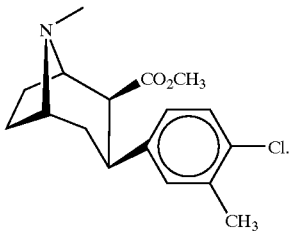

23. The method of claim 15, wherein $R^1$ is $CO_2CH_3$;

$R^2$ is $CH_3$;

X is chloro;

Y is methyl; and the dotted line between $C_2$ and $C_3$ represents an optional double bond.

24. The method of claim 23, wherein the compound is represented by the formula:

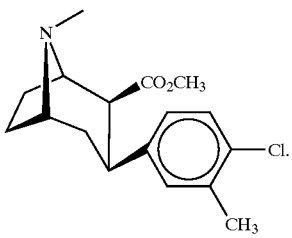

* * * * *

UNITED STATES PATENT AND TRADEMARK OFFICE
CERTIFICATE OF CORRECTION

PATENT NO. : 6,479,509 B1
DATED : November 12, 2002
INVENTOR(S) : F. Ivy Carroll It is certified that error appears in the above-identified patent and that said Letters Patent is hereby corrected as shown below:

Column 1,
Line 39, "nictone" should read -- nicotine --.

Column 5,
Line 8, "recognized that the that the $\alpha_4\beta2$" should read -- recognized that the $\alpha_4\beta2$ --.

Column 6,
Line 30, "and R is" should read -- and $R_x$ is --;
Line 58, "H $C_{1-6}$alkyl $C_{3-8}$" should read -- H,$C_{1-6}$alkyl, $C_{3-8}$ --;
Line 66, "stereochmeistry" should read -- stereochemistry --.

Column 7,
Line 5, "stereochmeistry" should read -- stereochemistry --.

Column 40,
Line 10, "N" should read -- H --.

Column 54,
Line 25, "$CH_3$" should read -- H --.

Column 76,
Line 33, "/" should read -- N --.

Column 81,
Lines 9 and 60, "war," should read -- was --.

UNITED STATES PATENT AND TRADEMARK OFFICE
CERTIFICATE OF CORRECTION

PATENT NO. : 6,479,509 B1
DATED : November 12, 2002
INVENTOR(S) : F. Ivy Carroll It is certified that error appears in the above-identified patent and that said Letters Patent is hereby corrected as shown below:

Column 82,
Line 37, "pyrrolidlinoamide" should read -- pyrrolidinoamide --;
Line 46, "was." should read -- was --;
Line 53, "RTI-5 1" should read -- RTI-51 --.

Column 84,
Line 44, move "CO$_2$CH$_3$  CH$_3$  H  H" to line 45 beside "WIN 33,065-2".

Column 85,
Table 2, line 11, "NTb" should read -- Nt$^b$ --.

Column 86,
Table 2, delete and replace with the following:

--

TABLE 2

Comparison of pharmacological potencies of tropane analogs in blocking nicotine-induced antinociception (tail-flick test and hypothermis after systemic administration to their binding affinities to [3H]monoamine transporters in brain

| Analog | AD50 Tail-Flick μmol/hg | AD50 Hypothermia μmol/hg | Dopamine [3H]WIN 35,428 IC50 nM | Serotonin [3H]Paroxetine IC50 nM | Norepinephrine [³H]Nixoxetine IC$_{50}$ nM |
|---|---|---|---|---|---|
| Cocaine | 3.2 | 20% @ 32 | 102 | 1060 | 3830 |
| RTI-29 | 6.8 | NT$^b$ | 9.8 | 5110 | 151 |
| RTI-31 | 7.2 | 1.1 | 1.12 | 44.5 | 37 |
| RTI-32 | 2.0 | 31.7 | 1.7 | 240 | 60 |
| RTF-51 | 1.0 | NT | 1.69 | 10.6 | 37.4 |
| RTI-55 | 0.9 | 1.2 | 1.26 | 4.2 | 63 |
| RTI-70 | 0% @ 90 | 40% @ 90 | 2070 | 59,500 | >200,000 |
| RTI-110 | 1.0 | NT$^b$ | 0.62 | 4.1 | 5.45 |
| RTI-111 | 1.3 | NT$^b$ | 0.79 | 3.1 | 17.9 |
| RTI-112 | 3.5 | 1.5 | 0.8 | 10.5 | 36.2 |
| RTC-113 | 5.6 | NT$^b$ | 1.98 | 2340 | 2926 |
| RTI-114 | 5.3 | 9 | 1.4 | 1404 | 778 |
| RTI-120 | 4.0 | NT$^b$ | 3.26 | 24,500 | 5830 |
| RTI-121 | 0.3 | 49 | 0.4 | 66.8 | 285 |
| RTI-147 | 5.7 | NT$^b$ | 1.38 | 12,400 | 3950 |
| RTI-229 | 3.6 | NT$^b$ | 0.37 | 1790 | 990 |
| RTI-258 | 19.1 | NT$^b$ | 22.7 | 66.3 | 760 |
| WIN 35,0652 | 8.0 | 6.7 | 23 | 1962 | 920 |

$^a$(Carroll et al., 1991, 1992, 1995; Lewin et al., 1992).
$^b$NT, not tested.

--

UNITED STATES PATENT AND TRADEMARK OFFICE
CERTIFICATE OF CORRECTION

PATENT NO. : 6,479,509 B1
DATED : November 12, 2002
INVENTOR(S) : F. Ivy Carroll It is certified that error appears in the above-identified patent and that said Letters Patent is hereby corrected as shown below:

Column 87,
Line 29, "Americ" should read -- Arneric --;
Line 60, "*Meurochem*" should read -- *Neurochem* --.

Column 88,
Line 40, "antidepressnats" should read -- antidepressants --;
Line 61, "agument" should read -- augment --.

Column 89,
Line 55, "alkyl," should read -- alkylnyl, --;
Line 66, "$(CH2)_nCO_2R_t$" should read -- $(CH2)_nCO_2R_x$ --.

Signed and Sealed this

Thirtieth Day of September, 2003

JAMES E. ROGAN
*Director of the United States Patent and Trademark Office*